US010828377B2

(12) United States Patent
Mano et al.

(10) Patent No.: US 10,828,377 B2
(45) Date of Patent: Nov. 10, 2020

(54) METHOD FOR DETERMINING PRESENCE OR ABSENCE OF SUFFERING FROM MALIGNANT LYMPHOMA OR LEUKEMIA, AND AGENT FOR TREATMENT AND/OR PREVENTION OF LEUKEMIA

(71) Applicants: THE UNIVERSITY OF TOKYO, Tokyo (JP); NATIONAL UNIVERSITY CORPORATION NAGOYA UNIVERSITY, Aichi (JP); AICHI PREFECTURE, Aichi (JP); NATIONAL HOSPITAL ORGANIZATION, Tokyo (JP)

(72) Inventors: Hiroyuki Mano, Tokyo (JP); Toshihide Ueno, Tokyo (JP); Takahiko Yasuda, Tokyo (JP); Masahito Kawazu, Tokyo (JP); Fumihiko Hayakawa, Aichi (JP); Hitoshi Kiyoi, Aichi (JP); Shinobu Tsuzuki, Aichi (JP); Tomoki Naoe, Aichi (JP)

(73) Assignees: THE UNIVERSITY OF TOKYO, Tokyo (JP); NATIONAL UNIVERSITY CORPORATION NAGOYA UNIVERSITY, Aichi (JP); AICHI PREFECTURE, Aichi (JP); NATIONAL HOSPITAL ORGANIZATION, Tokyo (JP)

( * ) Notice: Subject to any disclaimer, the term of this patent is extended or adjusted under 35 U.S.C. 154(b) by 83 days.

(21) Appl. No.: 15/770,947

(22) PCT Filed: Oct. 26, 2016

(86) PCT No.: PCT/JP2016/081738
§ 371 (c)(1),
(2) Date: Apr. 25, 2018

(87) PCT Pub. No.: WO2017/073619
PCT Pub. Date: May 4, 2017

(65) Prior Publication Data
US 2018/0318448 A1 Nov. 8, 2018

(30) Foreign Application Priority Data
Oct. 26, 2015 (JP) .................. 2015-210226

(51) Int. Cl.
| | |
|---|---|
| *A61P 35/02* | (2006.01) |
| *A61K 48/00* | (2006.01) |
| *C07K 14/435* | (2006.01) |
| *C12N 15/113* | (2010.01) |
| *G01N 33/574* | (2006.01) |
| *A61K 31/713* | (2006.01) |
| *A61K 31/7105* | (2006.01) |
| *C07K 16/18* | (2006.01) |
| *C07K 19/00* | (2006.01) |

(Continued)

(52) U.S. Cl.
CPC ........ *A61K 48/0066* (2013.01); *A61K 31/713* (2013.01); *A61K 31/7105* (2013.01); *A61K 45/06* (2013.01); *A61K 48/0033* (2013.01); *A61K 48/0091* (2013.01); *A61P 35/02* (2018.01); *C07K 14/435* (2013.01); *C07K 16/18* (2013.01); *C07K 19/00* (2013.01); *C12N 15/113* (2013.01); *C12Q 1/6886* (2013.01); *G01N 33/57407* (2013.01); *G01N 33/57426* (2013.01); *G01N 33/57496* (2013.01); *A61K 2300/00* (2013.01); *C07K 2319/30* (2013.01); *C12N 2310/14* (2013.01); *C12N 2310/531* (2013.01); *C12Q 2600/156* (2013.01); *C12Q 2600/158* (2013.01)

(58) Field of Classification Search
CPC ........................... A61K 48/0066; A61P 35/02
USPC ....................................................... 424/138.1
See application file for complete search history.

(56) References Cited

U.S. PATENT DOCUMENTS

| | | |
|---|---|---|
| 2012/0225034 A1 | 9/2012 | Belayew et al. |
| 2014/0105873 A1 | 4/2014 | Belayew et al. |

FOREIGN PATENT DOCUMENTS

| | | |
|---|---|---|
| EP | 2426203 A2 | 3/2012 |
| WO | 2005082933 A1 | 9/2005 |

OTHER PUBLICATIONS

Italiano et al (Genes Chromosomes Cancer, 2012, 51(3): 207-218).*

(Continued)

*Primary Examiner* — Sean E Aeder
(74) *Attorney, Agent, or Firm* — Lucas & Mercanti, LLP

(57) ABSTRACT

An object of the present invention is to provide a method for determining whether a subject suffers from malignant lymphoma or leukemia and an agent for treating and/or preventing the disease. The present invention relates to a method for assisting in determining whether a subject suffers from, or is likely to suffer from malignant lymphoma or leukemia, comprising: a detection step of detecting at least one of a fusion mutation of a DUX4 gene, an overexpression of a DUX4 gene, and a fusion mutation of an MEF2D gene; and a determination step of determining that the subject suffers from or is likely to suffer from the disease when at least one of the fusion mutations or the overexpression is detected. Moreover, the present invention relates to a pharmaceutical composition comprising a DUX4 inhibitor as an active ingredient, for treating and/or preventing malignant lymphoma or leukemia in a subject having a fusion mutation of a DUX4 gene and an IGH or IGL gene and/or overexpression of a DUX4 gene.

7 Claims, 19 Drawing Sheets
Specification includes a Sequence Listing.

(51) Int. Cl.
A61K 45/06 (2006.01)
C12Q 1/6886 (2018.01)

(56) References Cited

OTHER PUBLICATIONS

Pulte, D. et al., "Improvement in survival in younger patients with acute lymphoblastic leukemia form the 1980s to the early 21st century", Blood, vol. 113, No. 7, 2009 (pp. 1408-1411).

Schafer, E.S. et al., "Optimal therapy for acute lymphoblastic leukemia in adolescents and young adults", Nature Reviews Clinical Oncology, vol. 8, 2011 (pp. 417-424).

Yuki, Y. et al., "Identification of novel fusion gene in a pre-B acute lymphoblastic leukemia with t(1 ; 19) (q23 ; p13)", Cancer Science, vol. 95, No. 6, 2004 (pp. 503-507).

Prima, V. et al., "Cooperative transformation by MEF2D/DAZAP1 and DAZAP1/MEF2D fusion proteins generated by the variant t(1;19) in acute lymphoblastic leukemia", Leukemia, vol. 21, 2007 (pp. 2470-2475).

Lilljebjorn, H. et al., "RNA-seq identifies clinically relevant fusion genes in leukemia including a novel MEF2D/CSF1R fusion responsive to imatinib", Leukemia, vol. 28, 2014 (pp. 977-979, Table 1).

Lilljebjorn, H. et al., "Identification of ETV6-RUNX1-like and DUX4-rearranged subtypes in paediatric B-cell precusor acute lymphoblastic leukaemia", Nature communications, vol. 7, 2016 (pp. 1-13).

Liu, Y-F. et al., "Genomic Profiling of Adult and Pediatric B-cell Acute Lymphoblastic Leukemia", EBioMedicine, vol. 8, 2016 (pp. 173-183).

Yasuda, T. et al., "Recurrent DUX4 fusions in B cell acute lymphoblastic leukemia of adolescents and young adults", Nature Genetics, vol. 48, No. 5, 2016 (pp. 569-574).

Suzuki, K. et al., "MEF2D-BCL9 fusion gene is associated with high-risk acute B-cell precursor lymphoblastic leukemia in adolescents", Journal of Clinical Oncology, vol. 34, No. 28, 2016 (pp. 3451-3459).

* cited by examiner

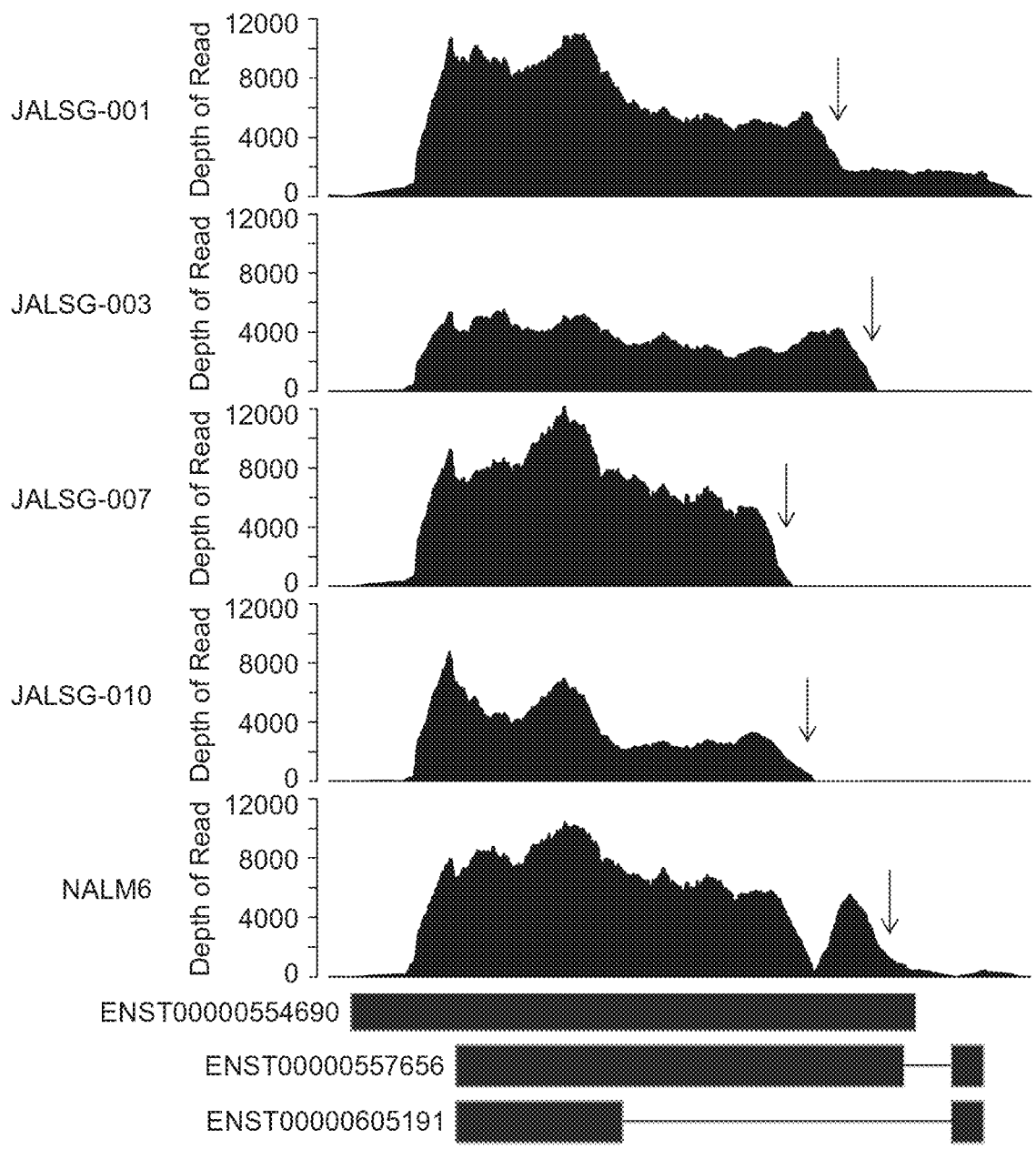

A

B

C

*P = 0.00047
**P = 0.0035
†No Significant Difference

SEQUENCE LISTING

<160> NUMBER OF SEQ ID NOS: 41

<210> SEQ ID NO 1
<211> LENGTH: 1272
<212> TYPE: DNA
<213> ORGANISM: Homo sapiens

<400> SEQUENCE: 1

```
atggccctcc cgacaccctc ggacagcacc ctccccgcgg aagcccgggg acgaggacgg    60
cgacggagac tcgtttggac cccgagccaa agcgaggccc tgcgagcctg ctttgagcgg   120
aacccgtacc cgggcatcgc caccagagaa cggctggccc aggccatcgg cattccggag   180
cccagggtcc agatttggtt tcagaatgag aggtcacgcc agctgaggca gcaccggcgg   240
gaatctcggc cctggcccgg gagacgcggc ccgccagaag gccggcgaaa gcggaccgcc   300
gtcaccggat cccagaccgc cctgctcctc cgagcctttg agaaggatcg ctttccaggc   360
atcgccgccc gggaggagct ggccagagag acgggcctcc ggagtccag gattcagatc   420
tggtttcaga atcgaagggc caggcacccg ggacagggtg gcagggcgcc cgcgcaggca   480
ggcggcctgt gcagcgcggc ccccggcggg ggtcaccctg ctccctcgtg ggtcgccttc   540
gcccacaccg gcgcgtgggg aacggggctt cccgcacccc acgtgccctg cgcgcctggg   600
gctctcccac agggggcttt cgtgagccag gcagcgaggg ccgccccgc gctgcagccc   660
agccaggccg cgccggcaga ggggatctcc caacctgccc cggcgcgcgg ggatttcgcc   720
tacgccgccc cggctcctcc ggacggggcg ctctcccacc ctcaggctcc tcggtggcct   780
ccgcacccgg gcaaaagccg ggaggaccgg acccgcagc gcgacggcct gccgggcccc   840
tgcgcggtgg cacagcctgg gcccgctcaa gcggggccgc agggccaagg ggtgcttgcg   900
ccacccacgt cccaggggag tccgtggtgg ggctggggcc ggggtcccca ggtcgccggg   960
gcggcgtggg aaccccaagc cggggcagct ccacctcccc agcccgcgcc cccggacgcc  1020
tccgcctccg cgcggcaggg gcagatgcaa ggcatcccgg cgccctccca ggcgctccag  1080
gagccggcgc cctggtctgc actcccctgc ggcctgctgc tggatgagct cctggcgagc  1140
ccggagtttc tgcagcaggc gcaacctctc ctagaaacgg aggccccggg ggagctggag  1200
gcctcggaag aggccgcctc gctggaagca cccctcagcg aggaagaata ccgggctctg  1260
ctggaggagc tt                                                      1272
```

<210> SEQ ID NO 2
<211> LENGTH: 424
<212> TYPE: PRT
<213> ORGANISM: Homo sapiens

<400> SEQUENCE: 2

```
Met Ala Leu Pro Thr Pro Ser Asp Ser Thr Leu Pro Ala Glu Ala Arg
  1               5                  10                  15

Gly Arg Gly Arg Arg Arg Arg Leu Val Trp Thr Pro Ser Gln Ser Glu
                 20                  25                  30

Ala Leu Arg Ala Cys Phe Glu Arg Asn Pro Tyr Pro Gly Ile Ala Thr
             35                  40                  45

Arg Glu Arg Leu Ala Gln Ala Ile Gly Ile Pro Glu Pro Arg Val Gln
         50                  55                  60

Ile Trp Phe Gln Asn Glu Arg Ser Arg Gln Leu Arg Gln His Arg Arg
 65                  70                  75                  80

Glu Ser Arg Pro Trp Pro Gly Arg Gly Pro Glu Gly Arg Arg
                 85                  90                  95

Lys Arg Thr Ala Val Thr Gly Ser Gln Thr Ala Leu Leu Leu Arg Ala
                100                 105                 110

Phe Glu Lys Asp Arg Phe Pro Gly Ile Ala Ala Arg Glu Glu Leu Ala
            115                 120                 125
```

```
Arg Glu Thr Gly Leu Pro Glu Ser Arg Ile Gln Ile Trp Phe Gln Asn
        130                 135                 140

Arg Arg Ala Arg His Pro Gly Gln Gly Gly Arg Ala Pro Ala Gln Ala
145                 150                 155                 160

Gly Gly Leu Cys Ser Ala Ala Pro Gly Gly His Pro Ala Pro Ser
                165                 170                 175

Trp Val Ala Phe Ala His Thr Gly Ala Trp Gly Thr Gly Leu Pro Ala
                180                 185                 190

Pro His Val Pro Cys Ala Pro Gly Ala Leu Pro Gln Gly Ala Phe Val
                195                 200                 205

Ser Gln Ala Ala Arg Ala Ala Pro Ala Leu Gln Pro Ser Gln Ala Ala
    210                 215                 220

Pro Ala Glu Gly Ile Ser Gln Pro Ala Pro Ala Arg Gly Asp Phe Ala
225                 230                 235                 240

Tyr Ala Ala Pro Ala Pro Pro Asp Gly Ala Leu Ser His Pro Gln Ala
                245                 250                 255

Pro Arg Trp Pro Pro His Pro Gly Lys Ser Arg Glu Asp Arg Asp Pro
                260                 265                 270

Gln Arg Asp Gly Leu Pro Gly Pro Cys Ala Val Ala Gln Pro Gly Pro
    275                 280                 285

Ala Gln Ala Gly Pro Gln Gly Gln Gly Val Leu Ala Pro Pro Thr Ser
    290                 295                 300

Gln Gly Ser Pro Trp Trp Gly Trp Gly Arg Gly Pro Gln Val Ala Gly
305                 310                 315                 320

Ala Ala Trp Glu Pro Gln Ala Gly Ala Ala Pro Pro Gln Pro Ala
                325                 330                 335

Pro Pro Asp Ala Ser Ala Ser Ala Arg Gln Gly Gln Met Gln Gly Ile
                340                 345                 350

Pro Ala Pro Ser Gln Ala Leu Gln Glu Pro Ala Pro Trp Ser Ala Leu
                355                 360                 365

Pro Cys Gly Leu Leu Leu Asp Glu Leu Leu Ala Ser Pro Glu Phe Leu
    370                 375                 380

Gln Gln Ala Gln Pro Leu Leu Glu Thr Glu Ala Pro Gly Glu Leu Glu
385                 390                 395                 400

Ala Ser Glu Glu Ala Ala Ser Leu Glu Ala Pro Leu Ser Glu Glu Glu
                405                 410                 415

Tyr Arg Ala Leu Leu Glu Glu Leu
            420

<210> SEQ ID NO 3
<211> LENGTH: 1563
<212> TYPE: DNA
<213> ORGANISM: Homo sapiens

<400> SEQUENCE: 3 atgggagga aaaagattca gatccagcga atcaccgacg agcggaaccg acaggtgact      60
ttcaccaagc ggaagtttgg cctgatgaag aaggcgtatg agctgagcgt gctatgtgac    120
tgcgagatcg cactcatcat cttcaaccac tccaacaagc tgttccagta cgccagcacc    180
gacatggaca aggtgctgct caagtacacg gagtacaatg agccacacga gagccgcacc    240
aacgccgaca tcatcgagac cctgaggaag aagggcttca acggctgcga cagccccgag    300
cccgacgggg aggactcgct ggaacagagc cccctgctgg aggacaagta ccgacgcgcc    360
agcgaggagc tcgacgggct cttccggcgc tatgggtcaa ctgtcccggc ccccaacttt    420
```

-continued

```
gccatgcctg tcacggtgcc cgtgtccaat cagagctcac tgcagttcag caatcccagc    480
ggctccctgg tcaccccttc cctggtgaca tcatccctca cggacccgcg gctcctgtcc    540
ccccagcagc cagcactaca gaggaacagt gtgtctcctg gcctgcccca gcggccagct    600
agtgcggggg ccatgctggg gggtgacctg aacagtgcta acggagcctg ccccagccct    660
gttgggaatg gctacgtcag tgctcgggct ccccctggcc tcctccctgt ggccaatggc    720
aacagcctaa acaaggtcat ccctgccaag tctccacccc cacctaccca cagcacccag    780
cttggagccc ccagccgcaa gcccgacctg cgagtcatca cttcccaggc aggaaagggg    840
ttaatgcatc acttgactga ggaccattta gatctgaaca atgcccagcg ccttggggtc    900
tcccagtcta ctcattcgct caccacccca gtggtttctg tggcaacgcc gagtttactc    960
agccagggcc tccccttctc ttccatgccc actgcctaca acacagatta ccagttgacc   1020
agtgcagagc tctcctcctt accagccttt agttcacctg gggggctgtc gctaggcaat   1080
gtcactgcct ggcaacagcc acagcagccc cagcagccgc agcagccaca gcctccacag   1140
cagcagccac cgcagccaca gcagccacag ccacagcagc tcagcagcc gcaacagcca   1200
cctcagcaac agtcccacct ggtccctgta tctctcagca acctcatccc gggcagcccc   1260
ctgccccacg tgggtgctgc cctcacagtc accacccacc cccacatcag catcaagtca   1320
gaaccggtgt ccccaagccg tgagcgcagc cctgcgcctc cccctccagc tgtgttccca   1380
gctgcccgcc ctgagcctgg cgatggtctc agcagcccag ccgggggatc ctatgagacg   1440
ggagaccggg atgacggacg gggggacttc gggcccacac tgggcctgct cgcccagcc   1500
ccagagcctg aggctgaggg ctcagctgtg aagaggatgc ggcttgatac ctggacatta   1560
aag                                                                 1563

<210> SEQ ID NO 4
<211> LENGTH: 521
<212> TYPE: PRT
<213> ORGANISM: Homo sapiens

<400> SEQUENCE: 4

Met Gly Arg Lys Lys Ile Gln Ile Gln Arg Ile Thr Asp Glu Arg Asn
1               5                   10                  15

Arg Gln Val Thr Phe Thr Lys Arg Lys Phe Gly Leu Met Lys Lys Ala
            20                  25                  30

Tyr Glu Leu Ser Val Leu Cys Asp Cys Glu Ile Ala Leu Ile Ile Phe
        35                  40                  45

Asn His Ser Asn Lys Leu Phe Gln Tyr Ala Ser Thr Asp Met Asp Lys
    50                  55                  60

Val Leu Leu Lys Tyr Thr Glu Tyr Asn Glu Pro His Glu Ser Arg Thr
65                  70                  75                  80

Asn Ala Asp Ile Ile Glu Thr Leu Arg Lys Lys Gly Phe Asn Gly Cys
                85                  90                  95

Asp Ser Pro Glu Pro Asp Gly Glu Asp Ser Leu Glu Gln Ser Pro Leu
            100                 105                 110

Leu Glu Asp Lys Tyr Arg Arg Ala Ser Glu Glu Leu Asp Gly Leu Phe
        115                 120                 125

Arg Arg Tyr Gly Ser Thr Val Pro Ala Pro Asn Phe Ala Met Pro Val
    130                 135                 140

Thr Val Pro Val Ser Asn Gln Ser Ser Leu Gln Phe Ser Asn Pro Ser
145                 150                 155                 160
```

```
Gly Ser Leu Val Thr Pro Ser Leu Val Thr Ser Ser Leu Thr Asp Pro
                165                 170                 175

Arg Leu Leu Ser Pro Gln Gln Pro Ala Leu Gln Arg Asn Ser Val Ser
            180                 185                 190

Pro Gly Leu Pro Gln Arg Pro Ala Ser Ala Gly Ala Met Leu Gly Gly
        195                 200                 205

Asp Leu Asn Ser Ala Asn Gly Ala Cys Pro Ser Pro Val Gly Asn Gly
    210                 215                 220

Tyr Val Ser Ala Arg Ala Ser Pro Gly Leu Leu Pro Val Ala Asn Gly
225                 230                 235                 240

Asn Ser Leu Asn Lys Val Ile Pro Ala Lys Ser Pro Pro Pro Pro Thr
                245                 250                 255

His Ser Thr Gln Leu Gly Ala Pro Ser Arg Lys Pro Asp Leu Arg Val
            260                 265                 270

Ile Thr Ser Gln Ala Gly Lys Gly Leu Met His His Leu Thr Glu Asp
        275                 280                 285

His Leu Asp Leu Asn Asn Ala Gln Arg Leu Gly Val Ser Gln Ser Thr
    290                 295                 300

His Ser Leu Thr Thr Pro Val Val Ser Val Ala Thr Pro Ser Leu Leu
305                 310                 315                 320

Ser Gln Gly Leu Pro Phe Ser Ser Met Pro Thr Ala Tyr Asn Thr Asp
                325                 330                 335

Tyr Gln Leu Thr Ser Ala Glu Leu Ser Ser Leu Pro Ala Phe Ser Ser
            340                 345                 350

Pro Gly Gly Leu Ser Leu Gly Asn Val Thr Ala Trp Gln Gln Pro Gln
        355                 360                 365

Gln Pro Gln Gln Pro Gln Gln Pro Gln Pro Gln Gln Gln Pro Pro
    370                 375                 380

Gln Pro Gln Gln Pro Gln Pro Gln Gln Pro Gln Gln Pro Gln Gln Pro
385                 390                 395                 400

Pro Gln Gln Gln Ser His Leu Val Pro Val Ser Leu Ser Asn Leu Ile
                405                 410                 415

Pro Gly Ser Pro Leu Pro His Val Gly Ala Ala Leu Thr Val Thr Thr
            420                 425                 430

His Pro His Ile Ser Ile Lys Ser Glu Pro Val Ser Pro Ser Arg Glu
        435                 440                 445

Arg Ser Pro Ala Pro Pro Pro Ala Val Phe Pro Ala Ala Arg Pro
450                 455                 460

Glu Pro Gly Asp Gly Leu Ser Ser Pro Ala Gly Gly Ser Tyr Glu Thr
465                 470                 475                 480

Gly Asp Arg Asp Asp Gly Arg Gly Asp Phe Gly Pro Thr Leu Gly Leu
                485                 490                 495

Leu Arg Pro Ala Pro Glu Pro Glu Ala Glu Gly Ser Ala Val Lys Arg
            500                 505                 510

Met Arg Leu Asp Thr Trp Thr Leu Lys
        515                 520

<210> SEQ ID NO 5
<211> LENGTH: 4278
<212> TYPE: DNA
<213> ORGANISM: Homo sapiens
```

```
<400> SEQUENCE: 5
atgcattcca gtaaccctaa agtgaggagc tctccatcag gaaacacaca gagtagccct      60
aagtcaaagc aggaggtgat ggtccgtccc cctacagtga tgtccccatc tggaaacccc     120
cagctggatt ccaaattctc caatcagggt aaacaggggg gctcagccag ccaatcccag     180 ccatcccct gtgactccaa gagtgggggc catacccta aagcactccc tggcccaggt      240
gggagcatgg ggctgaagaa tggggctgga atggtgcca agggcaaggg gaaaagggag      300
cgaagtattt ccgccgactc ctttgatcag agagatcctg ggactccaaa cgatgactct     360
gacattaaag aatgtaattc tgctgaccac ataaagtccc aggattccca gcacacacca     420
cactcgatga ccccatcaaa tgctacagcc cccaggtctt ctaccccctc ccatggccaa     480
actactgcca cagagcccac acctgctcag aagactccag ccaaagtggt gtacgtgttt     540
tctactgaga tggccaataa agctgcagaa gctgttttga agggccaggt tgaaactatc     600
gtctctttcc acatccagaa catttctaac aacaagacag agagaagcac agcgcctctg     660
aacacacaga tatctgccct tcggaatgat ccgaaacctc tcccacaaca gccccagct      720 ccggccaacc aggaccagaa ttcttcccag aataccagac tgcagccaac tccacccatt     780
ccggcaccag cacccaagcc tgccgcaccc ccacgtcccc tggaccggga gagtcctggg     840
gtagaaaaca aactgattcc ttctgtagga agtcctgcca gctccactcc actgccccca     900
gatggtactg ggcccaactc aactcccaac aatagggcag tgacccctgt ctcccagggg     960
agcaatagct cttcagcaga tcccaaagcc cctccgcctc caccagtgtc cagtggcgag    1020
ccccccacac tgggagagaa tcccgatggc ctatctcagg agcagctgga gcaccggag    1080 cgctccttac aaactctcag agatatccag cgcatgcttt ttcctgatga gaaagaattc    1140
acaggagcac aaagtggggg accgcagcag aatcctgggg tattagatgg gcctcagaaa    1200
aaaccagaag ggccaataca ggccatgatg gcccaatccc aaagcctagg taagggacct    1260
gggccccgga cagacgtggg agctccattt ggccctcaag acatagaga tgtacccttt     1320 tctccagatg aaatggttcc accttctatg aactcccagt ctgggaccat aggacccgac    1380
caccttgacc atatgactcc cgagcagata gcgtggctga aactgcagca ggagttttat    1440
gaagagaaga ggaggaagca ggaacaagtg gttgtccagc agtgttccct ccaggacatg    1500
atggtccatc agcacgggcc tcggggagtg gtccgaggac ccccccctcc ataccagatg    1560 accccctagtg aaggctgggc acctgggggt acagagccat tttctgatgg tatcaacatg    1620
ccacattctc tgccccgag gggcatggct ccccaccca acatgccagg agccagatg     1680 cgcctccctg gatttgcagg catgataaac tctgaaatgg aagggccgaa tgtccccaac    1740
cctgcatcta gaccaggtct ttctggagtc agttggccag atgatgtgcc aaaaatccca    1800
gatggtcgaa attttcctcc tggccagggc attttcagcg gtcctggccg aggggaacgc    1860
ttcccaaacc cccaaggatt gtctgaagag atgtttcagc agcagctggc agagaaacag    1920
ctgggtctcc ccccagggat ggccatggaa ggcatcaggc ccagcatgga gatgaacagg    1980
atgattccag ctcccagcg ccacatggag cctgggaata ccccatttt ccctcgaata     2040 ccagttgagg gccctctgag tccttctagg ggtgactttc caaaggaat tcccccacag    2100 atgggccctg gtcgggaact tgagtttggg atggttccta gtgggatgaa gggagatgtc    2160
aatctaaatg tcaacatggg atccaactct cagatgatac ctcagaagat gagagaggct    2220
ggggcgggcc ctgaggagat gctgaaatta cgcccaggtg gctcagacat gctgcctgct    2280
cagcagaaga tggtgccact gccatttggt gagcaccccc agcaggagta tggcatgggc    2340
```

-continued

```
cccagaccat tccttcccat gtctcagggt ccaggcagca acagtggctt gcggaatctc    2400
agagaaccaa ttgggcccga ccagaggact aacagccggc tcagtcatat gccaccacta    2460
cctctcaacc cttccagtaa ccccaccagc ctcaacacag ctcctccagt tcagcgcggc    2520
ctggggcgga agcccttgga tatatctgtg gcaggcagcc aggtgcattc ccaggcatt     2580 aaccctctga agtctcccac gatgcaccaa gtccagtcac caatgctggg ctcgccctcg    2640
gggaacctca gtcccccca gactccatcg cagctggcag gcatgctggc gggcccagct     2700
gctgctgctt ccattaagtc cccccctgtt ttggggtctg ctgctgcttc acctgtccac    2760
ctcaagtctc catcacttcc tgccccgtca cctggatgga cctcttctcc aaaacctccc    2820
cttcagagtc ctgggatccc tccaaaccat aaagcacccc tcaccatggc ctccccagcc    2880
atgctgggaa atgtagagtc aggtggcccc ccacctccta cagccagcca gcctgcctct    2940
gtgaatatcc ctggaagtct tccctctagt acaccttata ccatgcctcc agagccaacc    3000
ctttcccaga acccactctc tattatgatg tctcgaatgt ccaagtttgc aatgcccagt    3060
tccaccccgt tataccatga tgctatcaag actgtggcca gctcagatga cgactcccct    3120
ccagctcgtt ctcccaactt gccatcaatg aataatatgc caggaatggg cattaataca    3180
cagaatcctc gaatttcagg tccaaacccc gtggttccga tgccaaccct cagcccaatg    3240
ggaatgaccc agccactttc tcactccaat cagatgccct ctccaaatgc cgtgggaccc    3300 aacataccctc tcatggggt cccaatgggg cctggcttga tgtcacacaa tcctatcatg    3360
gggcatgggt cccaggagcc accgatggta cctcaaggac ggatgggctt cccccagggc    3420
ttccctccag tacagtctcc cccacagcag gttccattcc ctcacaatgg ccccagtggg    3480
gggcagggca gcttcccagg agggatgggt ttcccaggag aaggccccct tggccgcccc    3540
agcaacctgc cccaaagttc agcagatgca gcactttgca agcctggagg ccccggggt    3600 cctgactcct tcactgtcct ggggaacagc atgccttcgg tgtttacaga cccagatctg    3660
caggaggtca tccgacctgg agccaccgga atacctgagt tgatctatc ccgcattatt     3720 ccatctgaga agcccagcca gacgctgcaa tatttccctc gaggggaagt tccaggccgt    3780
aaacagcccc agggtcctgg acctgggtt tcacacatgc aggggatgat gggcgaacaa     3840
gcccccagaa tgggactagc attacctggc atgggaggtc cagggccagt gggaactccg    3900
gacatccctc ttggtacagc tccatccatg ccaggccaca accccatgag accaccagcc    3960
tttctccaac aaggcatgat gggacctcac catcggatga tgtcaccagc acaatctaca    4020
atgcccggcc agcccaccct gatgagcaat ccagctgctg ccgtgggcat gattcctggc    4080
aaggatcggg ggcctgccgg gctctacacc caccctgggc ctgtgggctc tccaggcatg    4140
atgatgtcca tgcagggcat gatgggaccc aacagaaca tcatgatccc cccacagatg     4200
aggccccggg gcatggctgc tgacgtgggc atgggtggat ttagccaagg acctggcaac    4260
ccaggaaaca tgatgttt                                                  4278
```

<210> SEQ ID NO 6
<211> LENGTH: 1426
<212> TYPE: PRT
<213> ORGANISM: Homo sapiens

<400> SEQUENCE: 6

```
Met His Ser Ser Asn Pro Lys Val Arg Ser Pro Ser Gly Asn Thr
1               5                   10                  15

Gln Ser Ser Pro Lys Ser Lys Gln Glu Val Met Val Arg Pro Pro Thr
            20                  25                  30
```

```
Val Met Ser Pro Ser Gly Asn Pro Gln Leu Asp Ser Lys Phe Ser Asn
         35                  40                  45
Gln Gly Lys Gln Gly Gly Ser Ala Ser Gln Ser Gln Pro Ser Pro Cys
 50                  55                  60
Asp Ser Lys Ser Gly Gly His Thr Pro Lys Ala Leu Pro Gly Pro Gly
 65                  70                  75                  80
Gly Ser Met Gly Leu Lys Asn Gly Ala Gly Asn Gly Ala Lys Gly Lys
                 85                  90                  95
Gly Lys Arg Glu Arg Ser Ile Ser Ala Asp Ser Phe Asp Gln Arg Asp
                100                 105                 110
Pro Gly Thr Pro Asn Asp Asp Ser Asp Ile Lys Glu Cys Asn Ser Ala
                115                 120                 125
Asp His Ile Lys Ser Gln Asp Ser Gln His Thr Pro His Ser Met Thr
         130                 135                 140
Pro Ser Asn Ala Thr Ala Pro Arg Ser Ser Thr Pro Ser His Gly Gln
145                 150                 155                 160
Thr Thr Ala Thr Glu Pro Thr Pro Ala Gln Lys Thr Pro Ala Lys Val
                165                 170                 175
Val Tyr Val Phe Ser Thr Glu Met Ala Asn Lys Ala Ala Glu Ala Val
                180                 185                 190
Leu Lys Gly Gln Val Glu Thr Ile Val Ser Phe His Ile Gln Asn Ile
         195                 200                 205
Ser Asn Asn Lys Thr Glu Arg Ser Thr Ala Pro Leu Asn Thr Gln Ile
         210                 215                 220
Ser Ala Leu Arg Asn Asp Pro Lys Pro Leu Pro Gln Gln Pro Pro Ala
225                 230                 235                 240
Pro Ala Asn Gln Asp Gln Asn Ser Ser Gln Asn Thr Arg Leu Gln Pro
                245                 250                 255
Thr Pro Pro Ile Pro Ala Pro Ala Pro Lys Pro Ala Ala Pro Pro Arg
                260                 265                 270
Pro Leu Asp Arg Glu Ser Pro Gly Val Glu Asn Lys Leu Ile Pro Ser
         275                 280                 285
Val Gly Ser Pro Ala Ser Ser Thr Pro Leu Pro Pro Asp Gly Thr Gly
         290                 295                 300
Pro Asn Ser Thr Pro Asn Asn Arg Ala Val Thr Pro Val Ser Gln Gly
305                 310                 315                 320
Ser Asn Ser Ser Ser Ala Asp Pro Lys Ala Pro Pro Pro Pro Pro Val
                325                 330                 335
Ser Ser Gly Glu Pro Pro Thr Leu Gly Glu Asn Pro Asp Gly Leu Ser
                340                 345                 350
Gln Glu Gln Leu Glu His Arg Glu Arg Ser Leu Gln Thr Leu Arg Asp
         355                 360                 365
Ile Gln Arg Met Leu Phe Pro Asp Glu Lys Glu Phe Thr Gly Ala Gln
         370                 375                 380
Ser Gly Gly Pro Gln Gln Asn Pro Gly Val Leu Asp Gly Pro Gln Lys
385                 390                 395                 400
Lys Pro Glu Gly Pro Ile Gln Ala Met Met Ala Gln Ser Gln Ser Leu
                405                 410                 415
Gly Lys Gly Pro Gly Pro Arg Thr Asp Val Gly Ala Pro Phe Gly Pro
                420                 425                 430
Gln Gly His Arg Asp Val Pro Phe Ser Pro Asp Glu Met Val Pro Pro
         435                 440                 445
```

```
Ser Met Asn Ser Gln Ser Gly Thr Ile Gly Pro Asp His Leu Asp His
    450             455             460
Met Thr Pro Glu Gln Ile Ala Trp Leu Lys Leu Gln Gln Glu Phe Tyr
465             470             475             480
Glu Glu Lys Arg Arg Lys Gln Glu Gln Val Val Gln Gln Cys Ser
                485             490             495
Leu Gln Asp Met Met Val His Gln His Gly Pro Arg Gly Val Val Arg
            500             505             510
Gly Pro Pro Pro Tyr Gln Met Thr Pro Ser Glu Gly Trp Ala Pro
        515             520             525
Gly Gly Thr Glu Pro Phe Ser Asp Gly Ile Asn Met Pro His Ser Leu
    530             535             540
Pro Pro Arg Gly Met Ala Pro His Pro Asn Met Pro Gly Ser Gln Met
545             550             555             560
Arg Leu Pro Gly Phe Ala Gly Met Ile Asn Ser Glu Met Glu Gly Pro
                565             570             575
Asn Val Pro Asn Pro Ala Ser Arg Pro Gly Leu Ser Gly Val Ser Trp
            580             585             590
Pro Asp Asp Val Pro Lys Ile Pro Asp Gly Arg Asn Phe Pro Pro Gly
        595             600             605
Gln Gly Ile Phe Ser Gly Pro Gly Arg Gly Glu Arg Phe Pro Asn Pro
    610             615             620
Gln Gly Leu Ser Glu Glu Met Phe Gln Gln Leu Ala Glu Lys Gln
625             630             635             640
Leu Gly Leu Pro Pro Gly Met Ala Met Glu Gly Ile Arg Pro Ser Met
                645             650             655
Glu Met Asn Arg Met Ile Pro Gly Ser Gln Arg His Met Glu Pro Gly
            660             665             670
Asn Asn Pro Ile Phe Pro Arg Ile Pro Val Glu Gly Pro Leu Ser Pro
        675             680             685
Ser Arg Gly Asp Phe Pro Lys Gly Ile Pro Pro Gln Met Gly Pro Gly
    690             695             700
Arg Glu Leu Glu Phe Gly Met Val Pro Ser Gly Met Lys Gly Asp Val
705             710             715             720
Asn Leu Asn Val Asn Met Gly Ser Asn Ser Gln Met Ile Pro Gln Lys
                725             730             735
Met Arg Glu Ala Gly Ala Gly Pro Glu Glu Met Leu Lys Leu Arg Pro
            740             745             750
Gly Gly Ser Asp Met Leu Pro Ala Gln Gln Lys Met Val Pro Leu Pro
        755             760             765
Phe Gly Glu His Pro Gln Gln Glu Tyr Gly Met Gly Pro Arg Pro Phe
    770             775             780
Leu Pro Met Ser Gln Gly Pro Gly Ser Asn Ser Gly Leu Arg Asn Leu
785             790             795             800
Arg Glu Pro Ile Gly Pro Asp Gln Arg Thr Asn Ser Arg Leu Ser His
                805             810             815
Met Pro Pro Leu Pro Leu Asn Pro Ser Ser Asn Pro Thr Ser Leu Asn
            820             825             830
Thr Ala Pro Pro Val Gln Arg Gly Leu Gly Arg Lys Pro Leu Asp Ile
        835             840             845
Ser Val Ala Gly Ser Gln Val His Ser Pro Gly Ile Asn Pro Leu Lys
    850             855             860
```

```
Ser Pro Thr Met His Gln Val Gln Ser Pro Met Leu Gly Ser Pro Ser
865                 870                 875                 880

Gly Asn Leu Lys Ser Pro Gln Thr Pro Ser Gln Leu Ala Gly Met Leu
                885                 890                 895

Ala Gly Pro Ala Ala Ala Ala Ser Ile Lys Ser Pro Val Leu Gly
        900                 905                 910

Ser Ala Ala Ala Ser Pro Val His Leu Lys Ser Pro Ser Leu Pro Ala
        915                 920                 925

Pro Ser Pro Gly Trp Thr Ser Ser Pro Lys Pro Pro Leu Gln Ser Pro
    930                 935                 940

Gly Ile Pro Pro Asn His Lys Ala Pro Leu Thr Met Ala Ser Pro Ala
945                 950                 955                 960

Met Leu Gly Asn Val Glu Ser Gly Gly Pro Pro Pro Thr Ala Ser
                965                 970                 975

Gln Pro Ala Ser Val Asn Ile Pro Gly Ser Leu Pro Ser Ser Thr Pro
            980                 985                 990

Tyr Thr Met Pro Pro Glu Pro Thr Leu Ser Gln Asn Pro Leu Ser Ile
            995                 1000                1005

Met Met Ser Arg Met Ser Lys Phe Ala Met Pro Ser Ser Thr Pro
    1010                1015                1020

Leu Tyr His Asp Ala Ile Lys Thr Val Ala Ser Ser Asp Asp Asp
    1025                1030                1035

Ser Pro Pro Ala Arg Ser Pro Asn Leu Pro Ser Met Asn Asn Met
    1040                1045                1050

Pro Gly Met Gly Ile Asn Thr Gln Asn Pro Arg Ile Ser Gly Pro
    1055                1060                1065

Asn Pro Val Val Pro Met Pro Thr Leu Ser Pro Met Gly Met Thr
    1070                1075                1080

Gln Pro Leu Ser His Ser Asn Gln Met Pro Ser Pro Asn Ala Val
    1085                1090                1095

Gly Pro Asn Ile Pro Pro His Gly Val Pro Met Gly Pro Gly Leu
    1100                1105                1110

Met Ser His Asn Pro Ile Met Gly His Gly Ser Gln Glu Pro Pro
    1115                1120                1125

Met Val Pro Gln Gly Arg Met Gly Phe Pro Gln Gly Phe Pro Pro
    1130                1135                1140

Val Gln Ser Pro Pro Gln Gln Val Pro Phe Pro His Asn Gly Pro
    1145                1150                1155

Ser Gly Gly Gln Gly Ser Phe Pro Gly Gly Met Gly Phe Pro Gly
    1160                1165                1170

Glu Gly Pro Leu Gly Arg Pro Ser Asn Leu Pro Gln Ser Ser Ala
    1175                1180                1185

Asp Ala Ala Leu Cys Lys Pro Gly Gly Pro Gly Pro Asp Ser
    1190                1195                1200

Phe Thr Val Leu Gly Asn Ser Met Pro Ser Val Phe Thr Asp Pro
    1205                1210                1215

Asp Leu Gln Glu Val Ile Arg Pro Gly Ala Thr Gly Ile Pro Glu
    1220                1225                1230

Phe Asp Leu Ser Arg Ile Ile Pro Ser Glu Lys Pro Ser Gln Thr
    1235                1240                1245

Leu Gln Tyr Phe Pro Arg Gly Glu Val Pro Gly Arg Lys Gln Pro
    1250                1255                1260
```

| | | | | | | | | | | |
|---|---|---|---|---|---|---|---|---|---|---|
|Gln|Gly|Pro|Gly|Pro|Gly|Phe|Ser|His|Met|Gln|Gly|Met|Met|Gly|
| |1265| | | |1270| | | |1275| | | | | |

Gln Gly Pro Gly Pro Gly Phe Ser His Met Gln Gly Met Met Gly
    1265            1270            1275

Glu Gln Ala Pro Arg Met Gly Leu Ala Leu Pro Gly Met Gly Gly
    1280            1285            1290

Pro Gly Pro Val Gly Thr Pro Asp Ile Pro Leu Gly Thr Ala Pro
    1295            1300            1305

Ser Met Pro Gly His Asn Pro Met Arg Pro Pro Ala Phe Leu Gln
    1310            1315            1320

Gln Gly Met Met Gly Pro His His Arg Met Met Ser Pro Ala Gln
    1325            1330            1335

Ser Thr Met Pro Gly Gln Pro Thr Leu Met Ser Asn Pro Ala Ala
    1340            1345            1350

Ala Val Gly Met Ile Pro Gly Lys Asp Arg Gly Pro Ala Gly Leu
    1355            1360            1365

Tyr Thr His Pro Gly Pro Val Gly Ser Pro Gly Met Met Met Ser
    1370            1375            1380

Met Gln Gly Met Met Gly Pro Gln Gln Asn Ile Met Ile Pro Pro
    1385            1390            1395

Gln Met Arg Pro Arg Gly Met Ala Ala Asp Val Gly Met Gly Gly
    1400            1405            1410

Phe Ser Gln Gly Pro Gly Asn Pro Gly Asn Met Met Phe
    1415            1420            1425

<210> SEQ ID NO 7
<211> LENGTH: 2568
<212> TYPE: DNA
<213> ORGANISM: Homo sapiens

<400> SEQUENCE: 7

```
atggatgtgc gccgtctgaa ggtgaacgaa cttcgcgagg agctgcagcg ccgcggcctg      60
gacactcgag gcctcaaggc cgagcttgct gagcggctgc aggcggcgtt ggaggccgag     120
gagcctgacg acgagcggga gctcgacgcc gacgacgaac cggggcgacc cgggcacatc     180
aacgaggagg tcgagaccga gggggggctcc gagctggagg ggaccgcgca gccaccgccg     240
cccgggctgc agccgcacgc ggagcccggc ggctactcgg ggccggacgg acattatgcc     300
atggacaata ttaccaggca gaaccaattc tacgataccc aagtcatcaa acaagaaaac     360
gagtcaggct acgagaggag accactggaa atggagcagc agcaggccta tcgtccagaa     420
atgaagacag agatgaagca aggagcaccc accagcttcc tcccgcctga agcttctcaa     480
ctcaagccag acaggcagca attccagagt cgaaagaggc ttatgaagaa aaaccgggga     540
cgggggtact tgagcaccg agaggatagg aggggccgct ctcctcagcc tcctgctgaa     600
gaggatgaag atgactttga tataccctt gttgctattg acacctataa ctgcgacctc     660
cacttcaagg tggcccgaga tcggagtagt ggctatccgc tcacaattga gggctttgca     720
tacctgtggt caggagcccg tgccagctat ggggtcagaa ggggccgtgt atgcttcgag     780
atgaagatca tgaggaaat ctccgtgaag caccttccgt ctacagagcc tgaccccac     840 gtggtccgta tcggctggtc cctggactcc tgcagcaccc agctaggcga agagcctttc     900
tcctatggct atggaggcac tgggaagaag tccaccaata gccggtttga aaactacgga     960
gacaagtttg cagagaacga tgtgattggc tgctttgcgg attttgaatg tggaaatgac    1020
gtggaactgt cttttaccaa gaatggaaag tggatgggca ttgctttccg aatccagaag    1080
gaagccttgg ggggtcaggc cctctatcct catgtcctgg tgaagaattg cgcagtggag    1140
```

-continued

```
ttcaacttcg  acagagagc   agagccctac  tgttctgtcc  tcccggggtt  taccttcatc  1200
cagcaccttc  cccttagtga  gcgtatccgg  ggcaccgttg  gaccaaagag  caaggcagaa  1260
tgtgagattc  tgatgatggt  gggcctgcct  gctgctggca  agaccacatg  ggccatcaaa  1320
catgcagcct  ccaacccttc  caagaagtac  aacatcctgg  gtaccaatgc  catcatggat  1380
aagatgcggg  tgatgggcct  acgccggcag  cggaactatg  ctggccgctg  ggatgtcctg  1440
atccagcagg  ccacccagtg  cctcaaccgc  tcatccaga   ttgctgcccg  caagaaacgc  1500
aactatatcc  tagatcagac  aaatgtttat  gggtcagccc  agagacgaaa  atgagacca   1560
tttgaaggct  tccagcgcaa  agctattgta  atttgtccca  ctgacgagga  cctaaaagac  1620
cgaacaataa  agcgaaccga  cgaggaaggg  aaggatgtcc  cagatcatgc  ggtcttagaa  1680
atgaaagcca  acttcacgtt  gccagatgtt  ggggacttcc  tggatgaggt  tctgttcatt  1740
gagctgcagc  gggaggaagc  ggacaagcta  gtgaggcagt  acaacgagga  aggccgcaag  1800
gctgggccac  cccctgaaaa  gcctttgac   aaccgaggtg  gtggtggctt  ccggggccgc  1860
gggggtggtg  gtggcttcca  gcgctatgaa  aaccgaggac  ccctggagg   caaccgtggc  1920
ggcttccaga  accgaggggg  aggcagcggt  ggaggaggca  actaccgagg  aggttcaac   1980
cgcagcggag  gtggtggcta  tagccagaac  cgctgggta   caacaaccg   ggataacaac  2040
aactccaaca  acagaggcag  ctacaaccgg  ctccccagc   aacagccgcc  accacagcag  2100
cctccgccac  cacagccacc  accccagcag  ccaccgccac  cacccagcta  cagccctgct  2160
cggaaccccc  caggggccag  cacctacaat  aagaacagca  acatccctgg  ctcaagcgcc  2220
aataccagca  cccccaccgt  cagcagctac  agccctccac  agccgagtta  cagccagcca  2280
ccctacaacc  agggaggtta  cagccagggc  tacacagccc  caccgcctcc  acctccacca  2340
ccacctgcct  acaactatgg  gagctacggc  ggttacaacc  cggccccta   taccccaccg  2400
ccaccccca   ctgcacagac  ctaccctcag  cccagctata  accagtatca  gcagtatgcc  2460
cagcagtgga  accagtacta  tcagaaccag  ggccagtggc  cgccatacta  cgggaactac  2520
gactacggga  gctactccgg  gaacacacag  ggtggcacaa  gtacacag                2568
```

<210> SEQ ID NO 8
<211> LENGTH: 856
<212> TYPE: PRT
<213> ORGANISM: Homo sapiens

<400> SEQUENCE: 8

```
Met Asp Val Arg Arg Leu Lys Val Asn Glu Leu Arg Glu Glu Leu Gln
1               5                   10                  15

Arg Arg Gly Leu Asp Thr Arg Gly Leu Lys Ala Glu Leu Ala Glu Arg
            20                  25                  30

Leu Gln Ala Ala Leu Glu Ala Glu Pro Asp Glu Arg Glu Leu
        35                  40                  45

Asp Ala Asp Asp Glu Pro Gly Arg Pro Gly His Ile Asn Glu Val
    50                  55                  60

Glu Thr Glu Gly Gly Ser Glu Leu Glu Gly Thr Ala Gln Pro Pro
65                  70                  75                  80

Pro Gly Leu Gln Pro His Ala Pro Gly Gly Tyr Ser Gly Pro Asp
            85                  90                  95

Gly His Tyr Ala Met Asp Asn Ile Thr Arg Gln Asn Gln Phe Tyr Asp
            100                 105                 110

Thr Gln Val Ile Lys Gln Glu Asn Glu Ser Gly Tyr Glu Arg Arg Pro
        115                 120                 125
```

-continued

```
Leu Glu Met Glu Gln Gln Gln Ala Tyr Arg Pro Glu Met Lys Thr Glu
130                 135                 140

Met Lys Gln Gly Ala Pro Thr Ser Phe Leu Pro Pro Glu Ala Ser Gln
145                 150                 155                 160

Leu Lys Pro Asp Arg Gln Gln Phe Gln Ser Arg Lys Arg Pro Tyr Glu
                165                 170                 175

Glu Asn Arg Gly Arg Gly Tyr Phe Glu His Arg Glu Asp Arg Arg Gly
                180                 185                 190

Arg Ser Pro Gln Pro Pro Ala Glu Glu Asp Glu Asp Phe Asp Asp
            195                 200                 205

Thr Leu Val Ala Ile Asp Thr Tyr Asn Cys Asp Leu His Phe Lys Val
210                 215                 220

Ala Arg Asp Arg Ser Ser Gly Tyr Pro Leu Thr Ile Glu Gly Phe Ala
225                 230                 235                 240

Tyr Leu Trp Ser Gly Ala Arg Ala Ser Tyr Gly Val Arg Arg Gly Arg
                245                 250                 255

Val Cys Phe Glu Met Lys Ile Asn Glu Glu Ile Ser Val Lys His Leu
                260                 265                 270

Pro Ser Thr Glu Pro Asp Pro His Val Val Arg Ile Gly Trp Ser Leu
        275                 280                 285

Asp Ser Cys Ser Thr Gln Leu Gly Glu Glu Pro Phe Ser Tyr Gly Tyr
        290                 295                 300

Gly Gly Thr Gly Lys Lys Ser Thr Asn Ser Arg Phe Glu Asn Tyr Gly
305                 310                 315                 320

Asp Lys Phe Ala Glu Asn Asp Val Ile Gly Cys Phe Ala Asp Phe Glu
                325                 330                 335

Cys Gly Asn Asp Val Glu Leu Ser Phe Thr Lys Asn Gly Lys Trp Met
            340                 345                 350

Gly Ile Ala Phe Arg Ile Gln Lys Glu Ala Leu Gly Gly Gln Ala Leu
            355                 360                 365

Tyr Pro His Val Leu Val Lys Asn Cys Ala Val Glu Phe Asn Phe Gly
        370                 375                 380

Gln Arg Ala Glu Pro Tyr Cys Ser Val Leu Pro Gly Phe Thr Phe Ile
385                 390                 395                 400

Gln His Leu Pro Leu Ser Glu Arg Ile Arg Gly Thr Val Gly Pro Lys
                405                 410                 415

Ser Lys Ala Glu Cys Glu Ile Leu Met Met Val Gly Leu Pro Ala Ala
            420                 425                 430

Gly Lys Thr Thr Trp Ala Ile Lys His Ala Ala Ser Asn Pro Ser Lys
            435                 440                 445

Lys Tyr Asn Ile Leu Gly Thr Asn Ala Ile Met Asp Lys Met Arg Val
        450                 455                 460

Met Gly Leu Arg Arg Gln Arg Asn Tyr Ala Gly Arg Trp Asp Val Leu
465                 470                 475                 480

Ile Gln Gln Ala Thr Gln Cys Leu Asn Arg Leu Ile Gln Ile Ala Ala
                485                 490                 495

Arg Lys Lys Arg Asn Tyr Ile Leu Asp Gln Thr Asn Val Tyr Gly Ser
            500                 505                 510

Ala Gln Arg Arg Lys Met Arg Pro Phe Glu Gly Phe Gln Arg Lys Ala
        515                 520                 525

Ile Val Ile Cys Pro Thr Asp Glu Asp Leu Lys Asp Arg Thr Ile Lys
        530                 535                 540
```

```
Arg Thr Asp Glu Glu Gly Lys Asp Val Pro Asp His Ala Val Leu Glu
545                 550                 555                 560

Met Lys Ala Asn Phe Thr Leu Pro Asp Val Gly Asp Phe Leu Asp Glu
            565                 570                 575

Val Leu Phe Ile Glu Leu Gln Arg Glu Glu Ala Asp Lys Leu Val Arg
        580                 585                 590

Gln Tyr Asn Glu Glu Gly Arg Lys Ala Gly Pro Pro Glu Lys Arg
    595                 600                 605

Phe Asp Asn Arg Gly Gly Gly Phe Arg Gly Arg Gly Gly Gly
610                 615                 620

Gly Phe Gln Arg Tyr Glu Asn Arg Gly Pro Pro Gly Gly Asn Arg Gly
625                 630                 635                 640

Gly Phe Gln Asn Arg Gly Gly Ser Gly Gly Gly Asn Tyr Arg
            645                 650                 655

Gly Gly Phe Asn Arg Ser Gly Gly Gly Tyr Ser Gln Asn Arg Trp
                660                 665                 670

Gly Asn Asn Asn Arg Asp Asn Asn Ser Asn Asn Arg Gly Ser Tyr
            675                 680                 685

Asn Arg Ala Pro Gln Gln Gln Pro Pro Gln Gln Pro Pro Pro
690                 695                 700

Gln Pro Pro Pro Gln Gln Pro Pro Pro Pro Ser Tyr Ser Pro Ala
705                 710                 715                 720

Arg Asn Pro Pro Gly Ala Ser Thr Tyr Asn Lys Asn Ser Asn Ile Pro
                725                 730                 735

Gly Ser Ser Ala Asn Thr Ser Thr Pro Thr Val Ser Ser Tyr Ser Pro
                740                 745                 750

Pro Gln Pro Ser Tyr Ser Gln Pro Pro Tyr Asn Gln Gly Gly Tyr Ser
                755                 760                 765

Gln Gly Tyr Thr Ala Pro Pro Pro Pro Pro Pro Pro Ala Tyr
    770                 775                 780

Asn Tyr Gly Ser Tyr Gly Gly Tyr Asn Pro Ala Pro Tyr Thr Pro Pro
785                 790                 795                 800

Pro Pro Pro Thr Ala Gln Thr Tyr Pro Gln Pro Ser Tyr Asn Gln Tyr
                805                 810                 815

Gln Gln Tyr Ala Gln Gln Trp Asn Gln Tyr Tyr Gln Asn Gln Gly Gln
            820                 825                 830

Trp Pro Pro Tyr Tyr Gly Asn Tyr Asp Tyr Gly Ser Tyr Ser Gly Asn
                835                 840                 845

Thr Gln Gly Gly Thr Ser Thr Gln
    850                 855

<210> SEQ ID NO 9
<211> LENGTH: 1119
<212> TYPE: DNA
<213> ORGANISM: Homo sapiens

<400> SEQUENCE: 9
atggccctcc cgacaccttc ggacagcacc ctccccgcgg aagcccgggg acgaggacgg      60
cgacggagac tcgtttggac cccgagccaa agcgaggccc tgcgagcctg ctttgagcgg     120
aacccgtacc cgggcatcgc caccagagaa cggctggccc aggccatcgg cattccggag     180
cccagggtcc agatttggtt tcagaatgag aggtcacgcc agctgaggca gcaccggcgg     240
gaatctcggc cctggcccgg agacgcggcc ccgccagaag gcggcgaaa gcggaccgcc     300 gtcaccggat cccagaccgc cctgctcctc cgagcctttg agaaggatcg ctttccaggc     360
```

```
atcgccgccc gggaggagct ggccagagag acgggcctcc cggagtccag gattcagatc    420
tggtttcaga atcgaagggc caggcacccg ggacagggtg gcaggcgcc cgcgcaggca     480
ggcggcctgt gcagcgcggc ccccggcggg ggtcaccctg ctccctcgtg ggtcgccttc    540
gcccacaccg gcgagtgggg aacgggcctt cccgcacccc acgtgccctg cgcgcctggg   600
gctctcccac aggggcttt cgtgagccag gcagcgaggg ccgcccccgc gctgcagccc    660
agccaggccg cgacggcaga gggggtctcc caacctgccc cggcgcgcgg ggatttcgcc    720
tacgccgccc cggctcctcc ggacggggcg ctctcccacc ctcaggctcc tcggtggcct    780
ccgcacccgg gcaaaagccg ggaggaccgg gacccgcagc gcgacggcct gccgggcccc   840
tgcgcggtgg cacagcctgg gcccgctcaa gcggggccgc agggccaagg ggtgcttgcg    900
ccacccacgt cccaggggag tccgtggtgg ggctggggcc ggggtcccca ggtcgccggg   960
gcggcgtggg aaccccaagc cggggcagct ccacctcccc agcccgcgcc cccggacgcc   1020
tccgcctccg cgcggcaggg gcagatgcaa ggcatcccgg cgccctccca ggcgctccag   1080
gagccggcgc cctggtctgc acagggttgg gggcagggg                           1119
```

<210> SEQ ID NO 10
<211> LENGTH: 373
<212> TYPE: PRT
<213> ORGANISM: Homo sapiens

<400> SEQUENCE: 10

```
Met Ala Leu Pro Thr Pro Ser Asp Ser Thr Leu Pro Ala Glu Ala Arg
1               5                   10                  15

Gly Arg Gly Arg Arg Arg Leu Val Trp Thr Pro Ser Gln Ser Glu
            20                  25                  30

Ala Leu Arg Ala Cys Phe Glu Arg Asn Pro Tyr Pro Gly Ile Ala Thr
        35                  40                  45

Arg Glu Arg Leu Ala Gln Ala Ile Gly Ile Pro Glu Pro Arg Val Gln
    50                  55                  60

Ile Trp Phe Gln Asn Glu Arg Ser Arg Gln Leu Arg Gln His Arg Arg
65                  70                  75                  80

Glu Ser Arg Pro Trp Pro Gly Arg Gly Pro Pro Glu Gly Arg Arg
                85                  90                  95

Lys Arg Thr Ala Val Thr Gly Ser Gln Thr Ala Leu Leu Leu Arg Ala
            100                 105                 110

Phe Glu Lys Asp Arg Phe Pro Gly Ile Ala Ala Arg Glu Glu Leu Ala
        115                 120                 125

Arg Glu Thr Gly Leu Pro Glu Ser Arg Ile Gln Ile Trp Phe Gln Asn
    130                 135                 140

Arg Arg Ala Arg His Pro Gly Gln Gly Gly Arg Ala Pro Ala Gln Ala
145                 150                 155                 160

Gly Gly Leu Cys Ser Ala Ala Pro Gly Gly His Pro Ala Pro Ser
            165                 170                 175

Trp Val Ala Phe Ala His Thr Gly Glu Trp Gly Thr Gly Leu Pro Ala
        180                 185                 190

Pro His Val Pro Cys Ala Pro Gly Ala Leu Pro Gln Gly Ala Phe Val
    195                 200                 205

Ser Gln Ala Ala Arg Ala Ala Pro Ala Leu Gln Pro Ser Gln Ala Ala
    210                 215                 220

Thr Ala Glu Gly Val Ser Gln Pro Ala Pro Ala Arg Gly Asp Phe Ala
225                 230                 235                 240
```

Tyr Ala Ala Pro Ala Pro Pro Asp Gly Ala Leu Ser His Pro Gln Ala
            245                 250                 255

Pro Arg Trp Pro Pro His Pro Gly Lys Ser Arg Glu Asp Arg Asp Pro
        260                 265                 270

Gln Arg Asp Gly Leu Pro Gly Pro Cys Ala Val Ala Gln Pro Gly Pro
    275                 280                 285

Ala Gln Ala Gly Pro Gln Gly Gln Gly Val Leu Ala Pro Pro Thr Ser
290                 295                 300

Gln Gly Ser Pro Trp Trp Gly Trp Gly Arg Gly Pro Gln Val Ala Gly
305                 310                 315                 320

Ala Ala Trp Glu Pro Gln Ala Gly Ala Ala Pro Pro Gln Pro Ala
            325                 330                 335

Pro Pro Asp Ala Ser Ala Ser Ala Arg Gln Gly Gln Met Gln Gly Ile
        340                 345                 350

Pro Ala Pro Ser Gln Ala Leu Gln Glu Pro Ala Pro Trp Ser Ala Gln
    355                 360                 365

Gly Trp Gly Gln Gly
    370

<210> SEQ ID NO 11
<211> LENGTH: 1293
<212> TYPE: DNA
<213> ORGANISM: Homo sapiens

<400> SEQUENCE: 11

```
atggccctcc cgacaccctc ggacagcacc ctccccgcgg aagcccgggg acgaggacgg      60
cgacggagac tcgtttggac cccgagccaa agcgaggccc tgcgagcctg ctttgagcgg     120
aacccgtacc cgggcatcgc caccagagaa cggctggccc aggccatcgg cattccggag     180
cccagggtcc agatttggtt tcagaatgag aggtcacgcc agctgaggca gcaccggcgg     240
gaatctcggc cctggcccgg agacgcggcc ccgccagaag gccggcgaaa gcggaccgcc     300
gtcaccggat cccagaccgc cctgctcctc cgagcctttg agaaggatcg ctttccaggc     360
atcgccgccc gggaggagct ggccagagag acgggcctcc cggagtccag gattcagatc     420
tggtttcaga atcgaagggc caggcacccg ggacagggtg gcagggcgcc cgcgcaggca     480
ggcggcctgt gcagcgcggc cccggcggg ggtcaccctg ctccctcgtg ggtcgccttc     540
gcccacaccg cgcgcgtgg gaacgggct cccgcacccc acgtgccctg cgcgcctggg     600
gctctcccac aggggctt cgtgagccag gcagcgaggg ccgcccccgc gctgcagccc     660
agccaggccg cgccggcaga ggggatctcc caacctgccc cggcgcgcgg ggatttcgcc     720
tacgccgccc cggctcctcc ggacggggcg ctctcccacc ctcaggctcc tgctggcct     780 ccgcacccgg gcaaaagccg gaggaccgg gaccgcagc gcgacggcct gccgggcccc     840
tgcgcggtgg cacagcctgg gccgctcaa gcggggccgc agggccaagg ggtgcttgcg     900
ccacccacgt cccagggag tccgtggtgg ggctggggcc gggtcccca ggtcgccggg     960 gcggcgtggg aaccccaagc cggggcagct ccacctcccc agcccgcgcc cccggacgcc    1020
tccgcctccg cgcggcaggg gcagatgcaa ggcatcccgg cgccctccca ggcgctccag    1080
gagccggcgc cctggtctgc actcccctgc ggcctgctgc tggatgagct cctggcgagc    1140
ccggagtttc tgcagcaggc gcaacctctc ctagaaacgg aggccccggg ggagctgctg    1200
tggggtttcc tgagcattgc aggttggtcc tcggggcatg ttccgagggg acctgggcgg    1260
actggccagg aggggacggg cactggggtg cct                                 1293
```

<210> SEQ ID NO 12
<211> LENGTH: 431
<212> TYPE: PRT
<213> ORGANISM: Homo sapiens

<400> SEQUENCE: 12

```
Met Ala Leu Pro Thr Pro Ser Asp Ser Thr Leu Pro Ala Glu Ala Arg
1               5                   10                  15

Gly Arg Gly Arg Arg Arg Arg Leu Val Trp Thr Pro Ser Gln Ser Glu
            20                  25                  30

Ala Leu Arg Ala Cys Phe Glu Arg Asn Pro Tyr Pro Gly Ile Ala Thr
        35                  40                  45

Arg Glu Arg Leu Ala Gln Ala Ile Gly Ile Pro Glu Pro Arg Val Gln
    50                  55                  60

Ile Trp Phe Gln Asn Glu Arg Ser Arg Gln Leu Arg Gln His Arg Arg
65                  70                  75                  80

Glu Ser Arg Pro Trp Pro Gly Arg Arg Gly Pro Glu Gly Arg Arg
                85                  90                  95

Lys Arg Thr Ala Val Thr Gly Ser Gln Thr Ala Leu Leu Arg Ala
            100                 105                 110

Phe Glu Lys Asp Arg Phe Pro Gly Ile Ala Ala Arg Glu Glu Leu Ala
        115                 120                 125

Arg Glu Thr Gly Leu Pro Glu Ser Arg Ile Gln Ile Trp Phe Gln Asn
    130                 135                 140

Arg Arg Ala Arg His Pro Gly Gln Gly Gly Arg Ala Pro Ala Gln Ala
145                 150                 155                 160

Gly Gly Leu Cys Ser Ala Ala Pro Gly Gly His Pro Ala Pro Ser
            165                 170                 175

Trp Val Ala Phe Ala His Thr Gly Ala Trp Gly Thr Gly Leu Pro Ala
        180                 185                 190

Pro His Val Pro Cys Ala Pro Gly Ala Leu Pro Gln Gly Ala Phe Val
    195                 200                 205

Ser Gln Ala Ala Arg Ala Ala Pro Ala Leu Gln Pro Ser Gln Ala Ala
    210                 215                 220

Pro Ala Glu Gly Ile Ser Gln Pro Ala Pro Ala Arg Gly Asp Phe Ala
225                 230                 235                 240

Tyr Ala Ala Pro Ala Pro Pro Asp Gly Ala Leu Ser His Pro Gln Ala
                245                 250                 255

Pro Arg Trp Pro Pro His Pro Gly Lys Ser Arg Glu Asp Arg Asp Pro
            260                 265                 270

Gln Arg Asp Gly Leu Pro Gly Pro Cys Ala Val Ala Gln Pro Gly Pro
        275                 280                 285

Ala Gln Ala Gly Pro Gln Gly Gln Gly Val Leu Ala Pro Pro Thr Ser
    290                 295                 300

Gln Gly Ser Pro Trp Trp Gly Trp Gly Arg Gly Pro Gln Val Ala Gly
305                 310                 315                 320

Ala Ala Trp Glu Pro Gln Ala Gly Ala Ala Pro Pro Gln Pro Ala
                325                 330                 335

Pro Pro Asp Ala Ser Ala Ser Ala Arg Gln Gly Gln Met Gln Gly Ile
            340                 345                 350

Pro Ala Pro Ser Gln Ala Leu Gln Glu Pro Ala Pro Trp Ser Ala Leu
        355                 360                 365

Pro Cys Gly Leu Leu Leu Asp Glu Leu Leu Ala Ser Pro Glu Phe Leu
    370                 375                 380
```

```
Gln Gln Ala Gln Pro Leu Leu Glu Thr Glu Ala Pro Gly Glu Leu Leu
385                 390                 395                 400

Trp Gly Phe Leu Ser Ile Ala Gly Trp Ser Ser Gly His Val Pro Arg
                405                 410                 415

Gly Pro Gly Arg Thr Gly Gln Glu Gly Thr Gly Thr Gly Val Pro
            420                 425                 430

<210> SEQ ID NO 13
<211> LENGTH: 1080
<212> TYPE: DNA
<213> ORGANISM: Homo sapiens

<400> SEQUENCE: 13
atggccctcc cgacaccttc ggacagcacc ctccccgcgg aagcccgggg acgaggacgg    60
cgatggagac tcgtttggac cccgagccaa agcgaggccc tgcgagcctg ctttgagcgg   120
aacccgtacc cgggcatcgc caccagagaa cggctggccc aggccatcgg cattccggag   180
cccagggtcc agatttggtt tcagaatgag aggtcacgcc agctgaggca gcaccggcgg   240
gaatctcggc cctggcccgg agacgcggc cgccagaag gccggcgaaa gcggaccgcc   300
gtcaccggat cccagaccgc cctgctcctc cgagcctttg agaaggatcg ctttccaggc   360
atcgccgccc gggaggagct ggccagagag acgggcctcc cggagtccag gattcagatc   420
tggtttcaga atcgaaggggc caggcacccg gacagggtg gcaggcgcc cgcgcaggca   480 ggcggcctgt gcagcgcggc cccggcgggg ggtcaccctg ctccctcgtg ggtcgccttc   540
gcccacaccg gcgcgtgggg aacgggcctt cccgcacccc acgtgccctg cgcgcctggg   600
gctctcccac aggggctttt cgtgagccag gcagcgaggg ccgccccgc gctgcagccc   660 agccaggccg cgccggcaga ggggatctcc caacctgccc cggcgcgcgg ggatttcgcc   720
tacgccgccc cggctcctcc ggacggggcg ctctcccacc ctcaggctcc tcggtggcct   780
ccgcacccgg gcaaaagccg ggaggaccgg gacccgcagc gcgacggcct gccgggcccc   840
tgcgcggtgg cacagcctgg gcccgctcaa gcggggccgc agggccaagg ggtgcttgcg   900
ccacccacgt cccaggggag tccgtggtgg ggctggggcc ggggtcccca ggtcgccggg   960
gcggcgtggg aacccaaagc cggggcagct ccacctcccc agcccgcgcc ccggacgcc   1020 tccgcgcggc aggggcagat gcaaggcatc ccggcgcctc agcgcctctg tggagacttg   1080

<210> SEQ ID NO 14
<211> LENGTH: 360
<212> TYPE: PRT
<213> ORGANISM: Homo sapiens

<400> SEQUENCE: 14

Met Ala Leu Pro Thr Pro Ser Asp Ser Thr Leu Pro Ala Glu Ala Arg
1               5                   10                  15

Gly Arg Gly Arg Arg Trp Arg Leu Val Trp Thr Pro Ser Gln Ser Glu
                20                  25                  30

Ala Leu Arg Ala Cys Phe Glu Arg Asn Pro Tyr Pro Gly Ile Ala Thr
            35                  40                  45

Arg Glu Arg Leu Ala Gln Ala Ile Gly Ile Pro Glu Pro Arg Val Gln
        50                  55                  60

Ile Trp Phe Gln Asn Glu Arg Ser Arg Gln Leu Arg Gln His Arg Arg
65                  70                  75                  80

Glu Ser Arg Pro Trp Pro Gly Arg Arg Gly Pro Glu Gly Arg Arg
                85                  90                  95
```

```
Lys Arg Thr Ala Val Thr Gly Ser Gln Thr Ala Leu Leu Leu Arg Ala
                100                 105                 110

Phe Glu Lys Asp Arg Phe Pro Gly Ile Ala Ala Arg Glu Glu Leu Ala
            115                 120                 125

Arg Glu Thr Gly Leu Pro Glu Ser Arg Ile Gln Ile Trp Phe Gln Asn
        130                 135                 140

Arg Arg Ala Arg His Pro Gly Gln Gly Gly Arg Ala Pro Ala Gln Ala
145                 150                 155                 160

Gly Gly Leu Cys Ser Ala Pro Gly Gly His Pro Ala Pro Ser
                165                 170                 175

Trp Val Ala Phe Ala His Thr Gly Ala Trp Gly Thr Gly Leu Pro Ala
                180                 185                 190

Pro His Val Pro Cys Ala Pro Gly Ala Leu Pro Gln Gly Ala Phe Val
            195                 200                 205

Ser Gln Ala Ala Arg Ala Ala Pro Ala Leu Gln Pro Ser Gln Ala Ala
        210                 215                 220

Pro Ala Glu Gly Ile Ser Gln Pro Ala Pro Ala Arg Gly Asp Phe Ala
225                 230                 235                 240

Tyr Ala Ala Pro Ala Pro Pro Asp Gly Ala Leu Ser His Pro Gln Ala
                245                 250                 255

Pro Arg Trp Pro Pro His Pro Gly Lys Ser Arg Glu Asp Arg Asp Pro
                260                 265                 270

Gln Arg Asp Gly Leu Pro Gly Pro Cys Ala Val Ala Gln Pro Gly Pro
            275                 280                 285

Ala Gln Ala Gly Pro Gln Gly Gln Gly Val Leu Ala Pro Pro Thr Ser
        290                 295                 300

Gln Gly Ser Pro Trp Trp Gly Trp Gly Arg Gly Pro Gln Val Ala Gly
305                 310                 315                 320

Ala Ala Trp Glu Pro Gln Ala Gly Ala Ala Pro Pro Gln Pro Ala
                325                 330                 335

Pro Pro Asp Ala Ser Ala Arg Gln Gly Gln Met Gln Gly Ile Pro Ala
            340                 345                 350

Pro Gln Arg Leu Cys Gly Asp Leu
        355                 360

<210> SEQ ID NO 15
<211> LENGTH: 954
<212> TYPE: DNA
<213> ORGANISM: Homo sapiens

<400> SEQUENCE: 15
atggccctcc cgacaccttc ggacagcacc ctccccgcgg aagcccgggg acgaggacgg      60
cgacggagac tcgtttggac cccgagccaa agcgaggccc tgcgagcctg ctttgagcgg     120
aacccgtacc cggcatcgc caccagagaa cggctggccc aggccatcgg cattccggag     180
cccagggtcc agatttggtt tcagaatgag aggtcacgcc agctgaggca gcaccggcgg     240
gaatctcggc cctggcccgg gagacgcggc ccgccagaag gccggcgaaa gcggaccgcc     300
gtcaccggat cccagaccgc cctgctcctc gagcctttg agaaggatcg ctttccaggc     360
atcgccgccc gggaggagct ggccagagag acgggcctcc ggagtccag gattcagatc     420 tggtttcaga atcgaagggc caggcacccg ggacagggtg cagggcgcc cgcgcaggca     480 ggcggcctgt gcaacgcggc ccccggcggg ggtcaccctg ctcccctcgt ggtcgccttc     540
gcccacaccg gcgcgtgggg aacggggctt cccgcacccc acgtgccctg cgcgcctggg     600
```

```
gctctcccac aggggctttt cgtgagccag gcagcgaggg ccgccccgc gctgcagccc      660 agccaggccg cgccggcaga ggggatctcc caacctgccc cggcgcgcgg ggatttcgcc      720
tacgccgccc cggctcctcc ggacggggcg ctctcccacc ctcaggctcc tcggtggcct      780
ccgcacccgg gcaaaagccg ggaggaccgg gacccgcagc gcgacggcct gccgggcccc      840
tgcgcggtgg cacagcctgg gcccgctcaa gcggggccgc agggccaagg ggtgcttgcg      900
ccacccacgt cccagggag tccgtggtgg ggctggggcc ggggtccctg cttc             954
```

```
<210> SEQ ID NO 16
<211> LENGTH: 318
<212> TYPE: PRT
<213> ORGANISM: Homo sapiens

<400> SEQUENCE: 16

Met Ala Leu Pro Thr Pro Ser Asp Ser Thr Leu Pro Ala Glu Ala Arg
1               5                   10                  15

Gly Arg Gly Arg Arg Arg Leu Val Trp Thr Pro Ser Gln Ser Glu
        20                  25                  30

Ala Leu Arg Ala Cys Phe Glu Arg Asn Pro Tyr Pro Gly Ile Ala Thr
            35                  40                  45

Arg Glu Arg Leu Ala Gln Ala Ile Gly Ile Pro Glu Pro Arg Val Gln
        50                  55                  60

Ile Trp Phe Gln Asn Glu Arg Ser Arg Gln Leu Arg Gln His Arg Arg
65                  70                  75                  80

Glu Ser Arg Pro Trp Pro Gly Arg Arg Gly Pro Pro Glu Gly Arg Arg
                85                  90                  95

Lys Arg Thr Ala Val Thr Gly Ser Gln Thr Ala Leu Leu Leu Arg Ala
            100                 105                 110

Phe Glu Lys Asp Arg Phe Pro Gly Ile Ala Ala Arg Glu Glu Leu Ala
        115                 120                 125

Arg Glu Thr Gly Leu Pro Glu Ser Arg Ile Gln Ile Trp Phe Gln Asn
    130                 135                 140

Arg Arg Ala Arg His Pro Gly Gln Gly Gly Arg Ala Pro Ala Gln Ala
145                 150                 155                 160

Gly Gly Leu Cys Asn Ala Ala Pro Gly Gly His Pro Ala Pro Ser
                165                 170                 175

Trp Val Ala Phe Ala His Thr Gly Ala Trp Gly Thr Gly Leu Pro Ala
            180                 185                 190

Pro His Val Pro Cys Ala Pro Gly Ala Leu Pro Gln Gly Ala Phe Val
        195                 200                 205

Ser Gln Ala Ala Arg Ala Ala Pro Ala Leu Gln Pro Ser Gln Ala Ala
    210                 215                 220

Pro Ala Glu Gly Ile Ser Gln Pro Ala Pro Ala Arg Gly Asp Phe Ala
225                 230                 235                 240

Tyr Ala Ala Pro Ala Pro Pro Asp Gly Ala Leu Ser His Pro Gln Ala
                245                 250                 255

Pro Arg Trp Pro Pro His Pro Gly Lys Ser Arg Glu Asp Arg Asp Pro
            260                 265                 270

Gln Arg Asp Gly Leu Pro Gly Pro Cys Ala Val Ala Gln Pro Gly Pro
        275                 280                 285

Ala Gln Ala Gly Pro Gln Gly Gln Val Leu Ala Pro Pro Thr Ser
    290                 295                 300

Gln Gly Ser Pro Trp Trp Gly Trp Gly Arg Gly Pro Cys Phe
305                 310                 315
```

<210> SEQ ID NO 17
<211> LENGTH: 1296
<212> TYPE: DNA
<213> ORGANISM: Homo sapiens

<400> SEQUENCE: 17

```
atggccctcc cgacaccttc ggacagcacc ctccccgcgg aagcccgggg acgaggacgg      60
cgacggagac tcgtttggac cccgagccaa agcgaggccc tgcgagcctg ctttgagcgg     120
aacccgtacc cgggcatcgc caccagagaa cggctggccc aggccatcgg cattccggag     180
cccagggtcc agatttggtt tcagaatgag aggtcacgcc agctgaggca gcaccggcgg     240
gaatctcggc cctggcccgg agacgcggcc cgccagaag gccggcgaaa gcggaccgcc      300
gtcaccggat cccagaccgc cctgctcctc cgagcctttg agaaggatcg ctttccaggc     360
atcgccgccc gggaggagct ggccagagag acgggcctcc ggagtccag gattcagatc      420
tggtttcaga atcgaagggc caggcacccg ggacagggtg gcagggcgcc cgcgcaggca     480
ggcggcctgt gcagcgcggc cccggcgggg ggtcaccctg ctccctcgtg ggtcgccttc     540
gcccacaccg gcgcgtgggg aacggggctt ccgcaccccc acgtgccctg cgcgcctggg     600
gctctcccac aggggctttt cgtgagccag gcagcgaggg ccgcccccgc gctgcagccc     660
agccaggccg cgccggcaga ggggatctcc caacctgccc cggcgcgcgg ggatttcgcc     720
tacgccgccc cggctcctcc ggacggggcg ctctcccacc ctcaggctcc tcggtggcct     780
ccgcacccgg gcaaaagccg ggaggaccgg gaccccgcagc gcgacggcct gccggggcccc    840
tgcgcggtgg cacagcctgg gcccgctcaa gcggggccgc agggccaagg ggtgcttgcg     900
ccacccacgt cccaggggag tccgtggtgg ggctggggcc ggggtcccca ggtcgccggg     960
gcggcgtggg aaccccaagc cggggcagct ccacctcccc agcccgcgcc ccggacgcc     1020
tccgcctccg cgcggcaggg gcagatgcaa ggcatcccgg cgccctccca ggcgctccag    1080
gagccggcgc cctggtctgc actccccctg cggcctgctgc tggatgagct cctggcgagc    1140
ccggagtttc tgcagcaggc gcaacctctc ctagaaacgg aggccccggg ggagctggag    1200
gcctcggaag aggccgcctc gctgcgatcc ctcagggttg gctgtagtca ccgtatgggg    1260
gaagcctgtg tcatcattta tttacccaac ctgggt                               1296
```

<210> SEQ ID NO 18
<211> LENGTH: 432
<212> TYPE: PRT
<213> ORGANISM: Homo sapiens

<400> SEQUENCE: 18

```
Met Ala Leu Pro Thr Pro Ser Asp Ser Thr Leu Pro Ala Glu Ala Arg
1               5                   10                  15

Gly Arg Gly Arg Arg Arg Leu Val Trp Thr Pro Ser Gln Ser Glu
            20                  25                  30

Ala Leu Arg Ala Cys Phe Glu Arg Asn Pro Tyr Pro Gly Ile Ala Thr
        35                  40                  45

Arg Glu Arg Leu Ala Gln Ala Ile Gly Ile Pro Glu Pro Arg Val Gln
    50                  55                  60

Ile Trp Phe Gln Asn Glu Arg Ser Arg Gln Leu Arg Gln His Arg Arg
65                  70                  75                  80

Glu Ser Arg Pro Trp Pro Gly Arg Arg Gly Pro Pro Glu Gly Arg Arg
                85                  90                  95

Lys Arg Thr Ala Val Thr Gly Ser Gln Thr Ala Leu Leu Leu Arg Ala
                100                 105                 110
```

Phe Glu Lys Asp Arg Phe Pro Gly Ile Ala Ala Arg Glu Leu Ala
            115                 120                 125

Arg Glu Thr Gly Leu Pro Glu Ser Arg Ile Gln Ile Trp Phe Gln Asn
        130                 135                 140

Arg Arg Ala Arg His Pro Gly Gln Gly Arg Ala Pro Ala Gln Ala
145                 150                 155                 160

Gly Gly Leu Cys Ser Ala Ala Pro Gly Gly His Pro Ala Pro Ser
                165                 170                 175

Trp Val Ala Phe Ala His Thr Gly Ala Trp Thr Gly Leu Pro Ala
            180                 185                 190

Pro His Val Pro Cys Ala Pro Gly Ala Leu Pro Gln Gly Ala Phe Val
        195                 200                 205

Ser Gln Ala Ala Arg Ala Ala Pro Ala Leu Gln Pro Ser Gln Ala Ala
    210                 215                 220

Pro Ala Glu Gly Ile Ser Gln Pro Ala Pro Ala Arg Gly Asp Phe Ala
225                 230                 235                 240

Tyr Ala Ala Pro Ala Pro Pro Asp Gly Ala Leu Ser His Pro Gln Ala
                245                 250                 255

Pro Arg Trp Pro Pro His Pro Gly Lys Ser Arg Glu Asp Arg Asp Pro
            260                 265                 270

Gln Arg Asp Gly Leu Pro Gly Pro Cys Ala Val Ala Gln Pro Gly Pro
        275                 280                 285

Ala Gln Ala Gly Pro Gln Gly Gln Gly Val Leu Ala Pro Pro Thr Ser
    290                 295                 300

Gln Gly Ser Pro Trp Trp Gly Trp Gly Arg Gly Pro Gln Val Ala Gly
305                 310                 315                 320

Ala Ala Trp Glu Pro Gln Ala Gly Ala Ala Pro Pro Gln Pro Ala
                325                 330                 335

Pro Pro Asp Ala Ser Ala Ser Ala Arg Gln Gly Gln Met Gln Gly Ile
            340                 345                 350

Pro Ala Pro Ser Gln Ala Leu Gln Glu Pro Ala Pro Trp Ser Ala Leu
        355                 360                 365

Pro Cys Gly Leu Leu Leu Asp Glu Leu Leu Ala Ser Pro Glu Phe Leu
    370                 375                 380

Gln Gln Ala Gln Pro Leu Leu Glu Thr Glu Ala Pro Gly Glu Leu Glu
385                 390                 395                 400

Ala Ser Glu Glu Ala Ala Ser Leu Arg Ser Leu Arg Val Gly Cys Ser
                405                 410                 415

His Arg Met Gly Glu Ala Cys Val Ile Ile Tyr Leu Pro Asn Leu Gly
            420                 425                 430

<210> SEQ ID NO 19
<211> LENGTH: 1779
<212> TYPE: DNA
<213> ORGANISM: Homo sapiens

<400> SEQUENCE: 19
atggggagga aaaagattca gatccagcga atcaccgacg agcggaaccg acaggtgact      60
ttcaccaagc ggaagtttgg cctgatgaag aaggcgtatg agctgagcgt gctatgtgac     120
tgcgagatcg cactcatcat cttcaaccac tccaacaagc tgttccagta cgccagcacc     180
gacatggaca ggtgctgct caagtacacg gagtacaatg agccacacga gccgcacc       240 aacgccgaca tcatcgagac cctgaggaag aagggcttca cggctgcga cagccccgag     300 cccgacgggg aggactcgct ggaacagagc ccctgctgg aggacaagta ccgacgcgcc     360

```
agcgaggagc tcgacgggct cttccggcgc tatgggtcaa ctgtcccggc ccccaacttt      420
gccatgcctg tcacggtgcc cgtgtccaat cagagctcac tgcagttcag caatcccagc      480
ggctccctgg tcaccccttc cctggtgaca tcatccctca cggacccgcg gctcctgtcc      540
ccccagcagc cagcactaca gaggaacagt gtgtctcctg gcctgcccca gcggccagct      600
agtgcggggg ccatgctggg gggtgacctg aacagtgcta acggagcctg ccccagccct      660
gttggaatgg gcattaatac acagaatcct cgaatttcag gtccaaaccc cgtggttccg      720
atgccaaccc tcagcccaat gggaatgacc cagccacttt ctcactccaa tcagatgccc      780
tctccaaatg ccgtgggacc caacatacct cctcatgggg tcccaatggg gcctggcttg      840
atgtcacaca atcctatcat ggggcatggg tcccaggagc caccgatggt acctcaagga      900
cggatgggct tcccccaggg cttccctcca gtacagtctc ccccacagca ggttccattc      960
cctcacaatg gccccagtgg ggggcagggc agcttcccag agggatgggt ttcccagga      1020
gaaggccccc ttggccgccc cagcaacctg ccccaaagtt cagcagatgc agcactttgc      1080
aagcctggag gccccggggg tcctgactcc ttcactgtcc tggggaacag catgccttcg      1140
gtgtttacag acccagatct gcaggaggtc atccgacctg gagccaccgg aatacctgag      1200
tttgatctat cccgcattat tccatctgag aagcccagcc agacgctgca atatttccct      1260
cgaggggaag ttccaggccg taaacagccc cagggtcctg gacctgggtt ttcacacatg      1320
caggggatga tgggcgaaca gccccccaga atgggactag cattacctgg catgggaggt      1380
ccagggccag tgggaactcc ggacatccct cttggtacag ctccatccat gccaggccac      1440
aaccccatga ccaccagcc ctttctccaa caaggcatga tgggacctca ccatcggatg      1500
atgtcaccag cacaatctac aatgcccggc cagcccaccc tgatgagcaa tccagctgct      1560
gccgtgggca tgattcctgg caaggatcgg ggggcctgccg ggctctacac ccaccctggg      1620
cctgtgggct ctccaggcat gatgatgtcc atgcagggca tgatgggacc ccaacagaac      1680
atcatgatcc ccccacagat gaggccccgg ggcatggctg ctgacgtggg catgggtgga      1740
tttagccaag gacctggcaa cccaggaaac atgatgttt                            1779
```

<210> SEQ ID NO 20
<211> LENGTH: 593
<212> TYPE: PRT
<213> ORGANISM: Homo sapiens

<400> SEQUENCE: 20

```
Met Gly Arg Lys Lys Ile Gln Ile Gln Arg Ile Thr Asp Glu Arg Asn
1               5                   10                  15

Arg Gln Val Thr Phe Thr Lys Arg Lys Phe Gly Leu Met Lys Lys Ala
            20                  25                  30

Tyr Glu Leu Ser Val Leu Cys Asp Cys Glu Ile Ala Leu Ile Ile Phe
        35                  40                  45

Asn His Ser Asn Lys Leu Phe Gln Tyr Ala Ser Thr Asp Met Asp Lys
    50                  55                  60

Val Leu Leu Lys Tyr Thr Glu Tyr Asn Glu Pro His Glu Ser Arg Thr
65                  70                  75                  80

Asn Ala Asp Ile Ile Glu Thr Leu Arg Lys Lys Gly Phe Asn Gly Cys
                85                  90                  95

Asp Ser Pro Glu Pro Asp Gly Glu Asp Ser Leu Glu Gln Ser Pro Leu
            100                 105                 110

Leu Glu Asp Lys Tyr Arg Arg Ala Ser Glu Glu Leu Asp Gly Leu Phe
        115                 120                 125
```

```
Arg Arg Tyr Gly Ser Thr Val Pro Ala Pro Asn Phe Ala Met Pro Val
    130                 135                 140
Thr Val Pro Val Ser Asn Gln Ser Ser Leu Gln Phe Ser Asn Pro Ser
145                 150                 155                 160
Gly Ser Leu Val Thr Pro Ser Leu Val Thr Ser Ser Leu Thr Asp Pro
                165                 170                 175
Arg Leu Leu Ser Pro Gln Gln Pro Ala Leu Gln Arg Asn Ser Val Ser
            180                 185                 190
Pro Gly Leu Pro Gln Arg Pro Ala Ser Ala Gly Ala Met Leu Gly Gly
        195                 200                 205
Asp Leu Asn Ser Ala Asn Gly Ala Cys Pro Ser Pro Val Gly Met Gly
    210                 215                 220
Ile Asn Thr Gln Asn Pro Arg Ile Ser Gly Pro Asn Pro Val Val Pro
225                 230                 235                 240
Met Pro Thr Leu Ser Pro Met Gly Met Thr Gln Pro Leu Ser His Ser
                245                 250                 255
Asn Gln Met Pro Ser Pro Asn Ala Val Gly Pro Asn Ile Pro Pro His
            260                 265                 270
Gly Val Pro Met Gly Pro Gly Leu Met Ser His Asn Pro Ile Met Gly
        275                 280                 285
His Gly Ser Gln Glu Pro Pro Met Val Pro Gln Gly Arg Met Gly Phe
    290                 295                 300
Pro Gln Gly Phe Pro Pro Val Gln Ser Pro Gln Gln Val Pro Phe
305                 310                 315                 320
Pro His Asn Gly Pro Ser Gly Gln Gly Ser Phe Pro Gly Gly Met
                325                 330                 335
Gly Phe Pro Gly Glu Gly Pro Leu Gly Arg Pro Ser Asn Leu Pro Gln
            340                 345                 350
Ser Ser Ala Asp Ala Ala Leu Cys Lys Pro Gly Gly Pro Gly Pro
        355                 360                 365
Asp Ser Phe Thr Val Leu Gly Asn Ser Met Pro Ser Val Phe Thr Asp
    370                 375                 380
Pro Asp Leu Gln Glu Val Ile Arg Pro Gly Ala Thr Gly Ile Pro Glu
385                 390                 395                 400
Phe Asp Leu Ser Arg Ile Ile Pro Ser Glu Lys Pro Ser Gln Thr Leu
                405                 410                 415
Gln Tyr Phe Pro Arg Gly Glu Val Pro Gly Arg Lys Gln Pro Gln Gly
            420                 425                 430
Pro Gly Pro Gly Phe Ser His Met Gln Gly Met Met Gly Glu Gln Ala
        435                 440                 445
Pro Arg Met Gly Leu Ala Leu Pro Gly Met Gly Gly Pro Gly Pro Val
    450                 455                 460
Gly Thr Pro Asp Ile Pro Leu Gly Thr Ala Pro Ser Met Pro Gly His
465                 470                 475                 480
Asn Pro Met Arg Pro Pro Ala Phe Leu Gln Gln Gly Met Met Gly Pro
                485                 490                 495
His His Arg Met Met Ser Pro Ala Gln Ser Thr Met Pro Gly Gln Pro
            500                 505                 510
Thr Leu Met Ser Asn Pro Ala Ala Val Gly Met Ile Pro Gly Lys
        515                 520                 525
Asp Arg Gly Pro Ala Gly Leu Tyr Thr His Pro Gly Pro Val Gly Ser
    530                 535                 540
```

Pro Gly Met Met Met Ser Met Gln Gly Met Met Gly Pro Gln Gln Asn
545                 550                 555                 560

Ile Met Ile Pro Pro Gln Met Arg Pro Arg Gly Met Ala Ala Asp Val
                565                 570                 575

Gly Met Gly Gly Phe Ser Gln Gly Pro Gly Asn Pro Gly Asn Met Met
                580                 585                 590

Phe

<210> SEQ ID NO 21
<211> LENGTH: 1722
<212> TYPE: DNA
<213> ORGANISM: Homo sapiens

<400> SEQUENCE: 21

| | | |
|---|---|---|
| atggggagga aaaagattca gatccagcga atcaccgacg agcggaaccg acaggtgact | 60 |
| ttcaccaagc ggaagtttgg cctgatgaag aaggcgtatg agctgagcgt gctatgtgac | 120 |
| tgcgagatcg cactcatcat cttcaaccac tccaacaagc tgttccagta cgccagcacc | 180 |
| gacatggaca aggtgctgct caagtacacg gagtacaatg agccacacga gagccgcacc | 240 |
| aacgccgaca tcatcgagac cctgaggaag aagggcttca cggctgcga cagccccgag | 300 |
| cccgacgggg aggactcgct ggaacagagc cccctgctgg aggacaagta ccgacgcgcc | 360 |
| agcgaggagc tcgacgggct cttccggcgc tatgggtcaa ctgtcccggc ccccaacttt | 420 |
| gccatgcctg tcacggtgcc cgtgtccaat cagagctcac tgcagttcag caatcccagc | 480 |
| ggctccctgg tcaccccttc cctggtgaca tcatccctca cggacccgcg gctcctgtcc | 540 |
| ccccagcagc agcactaca gaggaacagt gtgtctcctg gcctgcccca gcggccagct | 600 |
| agtgcgggaa tgggcattaa tacacagaat cctcgaattt caggtccaaa ccccgtggtt | 660 |
| ccgatgccaa ccctcagccc aatgggaatg acccagccac tttctcactc caatcagatg | 720 |
| ccctctccaa atgccgtggg acccaacata cctcctcatg gggtcccaat ggggcctggc | 780 |
| ttgatgtcac acaatcctat catggggcat gggtcccagg agccaccgat ggtacctcaa | 840 |
| ggacggatgg gcttccccca gggcttccct ccagtacagt ctcccccaca gcaggttcca | 900 |
| ttccctcaca atggcccag tggggggcag gcagcttcc caggagggat gggtttccca | 960 |
| ggagaaggcc cccttggccg ccccagcaac ctgccccaaa gttcagcaga tgcagcactt | 1020 |
| tgcaagcctg gaggccccgg gggtcctgac tccttcactg tcctggggaa cagcatgcct | 1080 |
| tcggtgttta cagacccaga tctgcaggag gtcatccgac ctggagccac cggaatacct | 1140 |
| gagtttgatc tatcccgcat tattccatct gagaagccca gccagacgct gcaatatttc | 1200 |
| cctcgagggg aagttccagg ccgtaaacag ccccagggtc ctggacctgg ttttcacac | 1260 |
| atgcagggga tgatgggcga acaagccccc agaatgggac tagcattacc tggcatggga | 1320 |
| ggtccagggc cagtgggaac tccggacatc cctcttggta cagctccatc catgccaggc | 1380 |
| cacaacccca tgagaccacc agcctttctc caacaaggca tgatgggacc tcaccatcgg | 1440 |
| atgatgtcac cagcacaatc tacaatgccc ggccagccca ccctgatgag caatccagct | 1500 |
| gctgccgtgg gcatgattcc tggcaaggat cggggggcctg ccgggctcta cacccacccct | 1560 |
| gggcctgtgg gctctccagg catgatgatg tccatgcagg gcatgatggg accccaacag | 1620 |
| aacatcatga tcccccaca gatgaggccc cggggcatgg ctgctgacgt gggcatgggt | 1680 |
| ggatttagcc aaggacctgg caacccagga aacatgatgt tt | 1722 |

```
<210> SEQ ID NO 22
<211> LENGTH: 574
<212> TYPE: PRT
<213> ORGANISM: Homo sapiens

<400> SEQUENCE: 22

Met Gly Arg Lys Lys Ile Gln Ile Gln Arg Ile Thr Asp Glu Arg Asn
1               5                   10                  15

Arg Gln Val Thr Phe Thr Lys Arg Lys Phe Gly Leu Met Lys Lys Ala
            20                  25                  30

Tyr Glu Leu Ser Val Leu Cys Asp Cys Glu Ile Ala Leu Ile Ile Phe
        35                  40                  45

Asn His Ser Asn Lys Leu Phe Gln Tyr Ala Ser Thr Asp Met Asp Lys
    50                  55                  60

Val Leu Leu Lys Tyr Thr Glu Tyr Asn Glu Pro His Glu Ser Arg Thr
65                  70                  75                  80

Asn Ala Asp Ile Ile Glu Thr Leu Arg Lys Lys Gly Phe Asn Gly Cys
                85                  90                  95

Asp Ser Pro Glu Pro Asp Gly Glu Asp Ser Leu Glu Gln Ser Pro Leu
            100                 105                 110

Leu Glu Asp Lys Tyr Arg Arg Ala Ser Glu Glu Leu Asp Gly Leu Phe
        115                 120                 125

Arg Arg Tyr Gly Ser Thr Val Pro Ala Pro Asn Phe Ala Met Pro Val
    130                 135                 140

Thr Val Pro Val Ser Asn Gln Ser Ser Leu Gln Phe Ser Asn Pro Ser
145                 150                 155                 160

Gly Ser Leu Val Thr Pro Ser Leu Val Thr Ser Ser Leu Thr Asp Pro
                165                 170                 175

Arg Leu Leu Ser Pro Gln Gln Pro Ala Leu Gln Arg Asn Ser Val Ser
            180                 185                 190

Pro Gly Leu Pro Gln Arg Pro Ala Ser Ala Gly Met Gly Ile Asn Thr
        195                 200                 205

Gln Asn Pro Arg Ile Ser Gly Pro Asn Pro Val Val Pro Met Pro Thr
    210                 215                 220

Leu Ser Pro Met Gly Met Thr Gln Pro Leu Ser His Ser Asn Gln Met
225                 230                 235                 240

Pro Ser Pro Asn Ala Val Gly Pro Asn Ile Pro Pro His Gly Val Pro
                245                 250                 255

Met Gly Pro Gly Leu Met Ser His Asn Pro Ile Met Gly His Gly Ser
            260                 265                 270

Gln Glu Pro Pro Met Val Pro Gln Gly Arg Met Gly Phe Pro Gln Gly
        275                 280                 285

Phe Pro Pro Val Gln Ser Pro Gln Gln Val Pro Phe Pro His Asn
    290                 295                 300

Gly Pro Ser Gly Gly Gln Gly Ser Phe Pro Gly Met Gly Phe Pro
305                 310                 315                 320

Gly Glu Gly Pro Leu Gly Arg Pro Ser Asn Leu Pro Gln Ser Ser Ala
                325                 330                 335

Asp Ala Ala Leu Cys Lys Pro Gly Gly Pro Gly Gly Pro Asp Ser Phe
            340                 345                 350

Thr Val Leu Gly Asn Ser Met Pro Ser Val Phe Thr Asp Pro Asp Leu
        355                 360                 365

Gln Glu Val Ile Arg Pro Gly Ala Thr Gly Ile Pro Glu Phe Asp Leu
    370                 375                 380
```

```
Ser Arg Ile Ile Pro Ser Glu Lys Pro Ser Gln Thr Leu Gln Tyr Phe
385                 390                 395                 400

Pro Arg Gly Glu Val Pro Gly Arg Lys Gln Pro Gln Gly Pro Gly Pro
                405                 410                 415

Gly Phe Ser His Met Gln Gly Met Met Gly Glu Gln Ala Pro Arg Met
            420                 425                 430

Gly Leu Ala Leu Pro Gly Met Gly Pro Gly Pro Val Gly Thr Pro
        435                 440                 445

Asp Ile Pro Leu Gly Thr Ala Pro Ser Met Pro Gly His Asn Pro Met
    450                 455                 460

Arg Pro Pro Ala Phe Leu Gln Gln Gly Met Met Gly Pro His His Arg
465                 470                 475                 480

Met Met Ser Pro Ala Gln Ser Thr Met Pro Gly Gln Pro Thr Leu Met
                485                 490                 495

Ser Asn Pro Ala Ala Val Gly Met Ile Pro Gly Lys Asp Arg Gly
            500                 505                 510

Pro Ala Gly Leu Tyr Thr His Pro Gly Pro Val Gly Ser Pro Gly Met
        515                 520                 525

Met Met Ser Met Gln Gly Met Met Gly Pro Gln Gln Asn Ile Met Ile
530                 535                 540

Pro Pro Gln Met Arg Pro Arg Gly Met Ala Ala Asp Val Gly Met Gly
545                 550                 555                 560

Gly Phe Ser Gln Gly Pro Gly Asn Pro Gly Asn Met Met Phe
            565                 570
```

<210> SEQ ID NO 23
<211> LENGTH: 2040
<212> TYPE: DNA
<213> ORGANISM: Homo sapiens

<400> SEQUENCE: 23

```
atggggagga aaaagattca gatccagcga atcaccgacg agcggaaccg acaggtgact      60
ttcaccaagc ggaagtttgg cctgatgaag aaggcgtatg agctgagcgt gctatgtgac     120
tgcgagatcg cactcatcat cttcaaccac tccaacaagc tgttccagta cgccagcacc     180
gacatggaca aggtgctgct caagtacacg gagtacaatg agccacacga gagccgcacc     240
aacgccgaca tcatcgagac cctgaggaag aagggcttca cggctgcga cagccccgag     300
cccgacgggg aggactcgct ggaacagagc cccctgctgg aggacaagta ccgacgcgcc     360
agcgaggagc tcgacgggct cttccggcgc tatgggtcaa ctgtcccggc ccccaacttt     420
gccatgcctg tcacggtgcc cgtgtccaat cagagctcac tgcagttcag caatcccagc     480
ggctccctgg tcaccccttc cctggtgaca tcatccctca cggacccgcg gctcctgtcc     540
ccccagcagc agcactaca aggaacagt gtgtctcctg gcctgcccca gcggccagct     600
agtgcggggg ccatgctggg gggtgacctg aacagtgcta acggagcctg ccccagccct     660
gttggtggcc ccccacctcc tacagccagc agcctgcct ctgtgaatat ccctggaagt     720
cttccctcta gtacacctta ccatgcct ccagagccaa cctttccca gaacccactc     780
tctattatga tgtctcgaat gtccaagttt gcaatgccca gttccacccc gttataccat     840
gatgctatca agactgtggc cagctcagat gacgactccc ctccagctcg ttctcccaac     900
ttgccatcaa tgaataatat gccaggaatg gcattaata cacagaatcc tcgaatttca     960
ggtccaaacc ccgtggttcc gatgccaacc ctcagcccaa tgggaatgac ccagccactt    1020
tctcactcca atcagatgcc ctctccaaat gccgtgggac ccaacatacc tcctcatggg    1080
```

-continued

```
gtcccaatgg ggcctggctt gatgtcacac aatcctatca tggggcatgg gtcccaggag    1140
ccaccgatgg tacctcaagg acggatgggc ttcccccagg gcttccctcc agtacagtct    1200
cccccacagc aggttccatt ccctcacaat ggccccagtg gggggcaggg cagcttccca    1260
ggagggatgg gtttcccagg agaaggcccc cttggccgcc ccagcaacct gccccaaagt    1320
tcagcagatg cagcactttg caagcctgga ggccccgggg gtcctgactc cttcactgtc    1380
ctggggaaca gcatgccttc ggtgtttaca gacccagatc tgcaggaggt catccgacct    1440
ggagccaccg gaatacctga gtttgatcta tcccgcatta ttccatctga aagcccagc     1500 cagacgctgc aatatttccc tcgaggggaa gttccaggcc gtaaacagcc cagggtcct    1560 ggacctgggt tttcacacat gcaggggatg atgggcgaac aagcccccag aatgggacta    1620
gcattacctg catgggagg tccagggcca gtgggaactc cggacatccc tcttggtaca     1680
gctccatcca tgccaggcca caaccccatg agaccaccag cctttctcca acaaggcatg    1740
atgggacctc accatcggat gatgtcacca gcacaatcta caatgcccgg ccagcccacc    1800
ctgatgagca atccagctgc tgccgtgggc atgattcctg caaggatcg ggggcctgcc     1860 gggctctaca cccaccctgg gcctgtgggc tctccaggca tgatgatgtc catgcagggc    1920
atgatgggac cccaacagaa catcatgatc cccccacaga tgaggcccg gggcatggct    1980 gctgacgtgg gcatgggtgg atttagccaa ggacctggca acccaggaaa catgatgttt    2040
```

<210> SEQ ID NO 24
<211> LENGTH: 680
<212> TYPE: PRT
<213> ORGANISM: Homo sapiens

<400> SEQUENCE: 24

Met Gly Arg Lys Lys Ile Gln Ile Gln Arg Ile Thr Asp Glu Arg Asn
1               5                   10                  15

Arg Gln Val Thr Phe Thr Lys Arg Lys Phe Gly Leu Met Lys Lys Ala
            20                  25                  30

Tyr Glu Leu Ser Val Leu Cys Asp Cys Glu Ile Ala Leu Ile Ile Phe
        35                  40                  45

Asn His Ser Asn Lys Leu Phe Gln Tyr Ala Ser Thr Asp Met Asp Lys
    50                  55                  60

Val Leu Leu Lys Tyr Thr Glu Tyr Asn Glu Pro His Glu Ser Arg Thr
65                  70                  75                  80

Asn Ala Asp Ile Ile Glu Thr Leu Arg Lys Lys Gly Phe Asn Gly Cys
                85                  90                  95

Asp Ser Pro Glu Pro Asp Gly Glu Asp Ser Leu Glu Gln Ser Pro Leu
            100                 105                 110

Leu Glu Asp Lys Tyr Arg Arg Ala Ser Glu Glu Leu Asp Gly Leu Phe
        115                 120                 125

Arg Arg Tyr Gly Ser Thr Val Pro Ala Pro Asn Phe Ala Met Pro Val
    130                 135                 140

Thr Val Pro Val Ser Asn Gln Ser Ser Leu Gln Phe Ser Asn Pro Ser
145                 150                 155                 160

Gly Ser Leu Val Thr Pro Ser Leu Val Thr Ser Ser Leu Thr Asp Pro
                165                 170                 175

Arg Leu Leu Ser Pro Gln Gln Pro Ala Leu Gln Arg Asn Ser Val Ser
            180                 185                 190

Pro Gly Leu Pro Gln Arg Pro Ala Ser Ala Gly Ala Met Leu Gly Gly
        195                 200                 205

```
Asp Leu Asn Ser Ala Asn Gly Ala Cys Pro Ser Pro Val Gly Gly Pro
    210                 215                 220

Pro Pro Pro Thr Ala Ser Gln Pro Ala Ser Val Asn Ile Pro Gly Ser
225                 230                 235                 240

Leu Pro Ser Ser Thr Pro Tyr Thr Met Pro Glu Pro Thr Leu Ser
                245                 250                 255

Gln Asn Pro Leu Ser Ile Met Met Ser Arg Met Ser Lys Phe Ala Met
                260                 265                 270

Pro Ser Ser Thr Pro Leu Tyr His Asp Ala Ile Lys Thr Val Ala Ser
            275                 280                 285

Ser Asp Asp Ser Pro Ala Arg Ser Pro Asn Leu Pro Ser Met
    290                 295                 300

Asn Asn Met Pro Gly Met Gly Ile Asn Thr Gln Asn Pro Arg Ile Ser
305                 310                 315                 320

Gly Pro Asn Pro Val Val Pro Met Pro Thr Leu Ser Pro Met Gly Met
                325                 330                 335

Thr Gln Pro Leu Ser His Ser Asn Gln Met Pro Ser Pro Asn Ala Val
                340                 345                 350

Gly Pro Asn Ile Pro Pro His Gly Val Pro Met Gly Pro Gly Leu Met
            355                 360                 365

Ser His Asn Pro Ile Met Gly His Gly Ser Gln Glu Pro Pro Met Val
    370                 375                 380

Pro Gln Gly Arg Met Gly Phe Pro Gln Gly Phe Pro Val Gln Ser
385                 390                 395                 400

Pro Pro Gln Gln Val Pro Phe Pro His Asn Gly Pro Ser Gly Gly Gln
                405                 410                 415

Gly Ser Phe Pro Gly Gly Met Gly Phe Pro Gly Glu Gly Pro Leu Gly
            420                 425                 430

Arg Pro Ser Asn Leu Pro Gln Ser Ser Ala Asp Ala Leu Cys Lys
    435                 440                 445

Pro Gly Gly Pro Gly Gly Pro Asp Ser Phe Thr Val Leu Gly Asn Ser
450                 455                 460

Met Pro Ser Val Phe Thr Asp Pro Asp Leu Gln Glu Val Ile Arg Pro
465                 470                 475                 480

Gly Ala Thr Gly Ile Pro Glu Phe Asp Leu Ser Arg Ile Ile Pro Ser
                485                 490                 495

Glu Lys Pro Ser Gln Thr Leu Gln Tyr Phe Pro Arg Gly Glu Val Pro
            500                 505                 510

Gly Arg Lys Gln Pro Gln Gly Pro Gly Pro Gly Phe Ser His Met Gln
    515                 520                 525

Gly Met Met Gly Glu Gln Ala Pro Arg Met Gly Leu Ala Leu Pro Gly
530                 535                 540

Met Gly Gly Pro Gly Pro Val Gly Thr Pro Asp Ile Pro Leu Gly Thr
545                 550                 555                 560

Ala Pro Ser Met Pro Gly His Asn Pro Met Arg Pro Pro Ala Phe Leu
                565                 570                 575

Gln Gln Gly Met Met Gly Pro His His Arg Met Met Ser Pro Ala Gln
            580                 585                 590

Ser Thr Met Pro Gly Gln Pro Thr Leu Met Ser Asn Pro Ala Ala Ala
    595                 600                 605

Val Gly Met Ile Pro Gly Lys Asp Arg Gly Pro Ala Gly Leu Tyr Thr
610                 615                 620
```

```
His Pro Gly Pro Val Gly Ser Pro Gly Met Met Ser Met Gln Gly
625                 630                 635                 640

Met Met Gly Pro Gln Gln Asn Ile Met Ile Pro Pro Gln Met Arg Pro
            645                 650                 655

Arg Gly Met Ala Ala Asp Val Gly Met Gly Gly Phe Ser Gln Gly Pro
            660                 665                 670

Gly Asn Pro Gly Asn Met Met Phe
            675                 680

<210> SEQ ID NO 25
<211> LENGTH: 1983
<212> TYPE: DNA
<213> ORGANISM: Homo sapiens

<400> SEQUENCE: 25
```

| | | | | | |
|---|---|---|---|---|---|
| atggggagga | aaaagattca | gatccagcga | atcaccgacg | agcggaaccg | acaggtgact | 60 |
| ttcaccaagc | ggaagtttgg | cctgatgaag | aaggcgtatg | agctgagcgt | gctatgtgac | 120 |
| tgcgagatcg | cactcatcat | cttcaaccac | tccaacaagc | tgttccagta | cgccagcacc | 180 |
| gacatggaca | aggtgctgct | caagtacacg | gagtacaatg | agccacacga | gagccgcacc | 240 |
| aacgccgaca | tcatcgagac | cctgaggaag | aagggcttca | acggctgcga | cagccccgag | 300 |
| cccgacgggg | aggactcgct | ggaacagagc | cccctgctgg | aggacaagta | ccgacgcgcc | 360 |
| agcgaggagc | tcgacgggct | cttccggcgc | tatgggtcaa | ctgtcccggc | cccaactttt | 420 |
| gccatgcctg | tcacggtgcc | cgtgtccaat | cagagctcac | tgcagttcag | caatcccagc | 480 |
| ggctccctgg | tcaccccttc | cctggtgaca | tcatccctca | cggacccgcg | gctcctgtcc | 540 |
| ccccagcagc | cagcactaca | gaggaacagt | gtgtctcctg | gcctgcccca | gcggccagct | 600 |
| agtgcgggtg | ccccccaccc | tcctacagcc | agccagcctg | cctctgtgaa | atccctgga | 660 |
| agtcttccct | ctagtacacc | ttataccatg | cctccagagc | caacccttc | ccagaaccca | 720 |
| ctctctatta | tgatgtctcg | aatgtccaag | tttgcaatgc | ccagttccac | cccgttatac | 780 |
| catgatgcta | tcaagactgt | ggccagctca | gatgacgact | cccctccagc | tcgttctccc | 840 |
| aacttgccat | caatgaataa | tatgccagga | atgggcatta | atacacagaa | tcctcgaatt | 900 |
| tcaggtccaa | accccgtggt | tccgatgcca | accctcagcc | caatgggaat | gacccagcca | 960 |
| ctttctcact | ccaatcagat | gccctctcca | aatgccgtgg | acccaacat | acctcctcat | 1020 |
| ggggtcccaa | tggggcctgg | cttgatgtca | cacaatccta | tcatggggca | tgggtcccag | 1080 |
| gagccaccga | tggtacctca | aggacggatg | ggcttccccc | agggcttccc | tccagtacag | 1140 |
| tctccccac | agcaggttcc | attccctcac | aatggcccca | gtgggggca | gggcagcttc | 1200 |
| ccaggaggga | tgggttttccc | aggagaaggc | cccctttggcc | gccccagcaa | cctgccccaa | 1260 |
| agttcagcag | atgcagcact | ttgcaagcct | ggaggccccg | ggggtcctga | ctccttcact | 1320 |
| gtcctgggga | acagcatgcc | ttcggtgttt | acagacccag | atctgcagga | ggtcatccga | 1380 |
| cctggagcca | ccggaatacc | tgagtttgat | ctatcccgca | ttattccatc | tgagaagccc | 1440 |
| agccagacgc | tgcaatattt | ccctcgaggg | gaagttccag | gccgtaaaca | gccccagggt | 1500 |
| cctggacctg | ggttttcaca | catgcaggg | atgatgggcg | aacaagcccc | cagaatggga | 1560 |
| ctagcattac | ctggcatggg | aggtccaggg | ccagtgggaa | ctccggacat | ccctcttggt | 1620 |
| acagctccat | ccatgccagg | ccacaaccccc | atgagaccac | cagcctttct | ccaacaaggc | 1680 |
| atgatgggac | tcaccatcg | gatgatgtca | ccagcacaat | ctacaatgcc | cggccagccc | 1740 |
| accctgatga | gcaatccagc | tgctgccgtg | ggcatgattc | ctggcaagga | tcggggggct | 1800 |

-continued

```
gccgggctct acacccaccc tgggcctgtg ggctctccag gcatgatgat gtccatgcag    1860
ggcatgatgg gacccaaaca gaacatcatg atccccccac agatgaggcc ccggggcatg    1920
gctgctgacg tgggcatggg tggatttagc caaggacctg gcaacccagg aaacatgatg    1980
ttt                                                                   1983
```

<210> SEQ ID NO 26
<211> LENGTH: 661
<212> TYPE: PRT
<213> ORGANISM: Homo sapiens

<400> SEQUENCE: 26

```
Met Gly Arg Lys Lys Ile Gln Ile Gln Arg Ile Thr Asp Glu Arg Asn
1               5                   10                  15

Arg Gln Val Thr Phe Thr Lys Arg Lys Phe Gly Leu Met Lys Lys Ala
            20                  25                  30

Tyr Glu Leu Ser Val Leu Cys Asp Cys Glu Ile Ala Leu Ile Ile Phe
        35                  40                  45

Asn His Ser Asn Lys Leu Phe Gln Tyr Ala Ser Thr Asp Met Asp Lys
    50                  55                  60

Val Leu Leu Lys Tyr Thr Glu Tyr Asn Glu Pro His Glu Ser Arg Thr
65                  70                  75                  80

Asn Ala Asp Ile Ile Glu Thr Leu Arg Lys Lys Gly Phe Asn Gly Cys
                85                  90                  95

Asp Ser Pro Glu Pro Asp Gly Glu Asp Ser Leu Glu Gln Ser Pro Leu
            100                 105                 110

Leu Glu Asp Lys Tyr Arg Arg Ala Ser Glu Glu Leu Asp Gly Leu Phe
        115                 120                 125

Arg Arg Tyr Gly Ser Thr Val Pro Ala Pro Asn Phe Ala Met Pro Val
    130                 135                 140

Thr Val Pro Val Ser Asn Gln Ser Ser Leu Gln Phe Ser Asn Pro Ser
145                 150                 155                 160

Gly Ser Leu Val Thr Pro Ser Leu Val Thr Ser Ser Leu Thr Asp Pro
                165                 170                 175

Arg Leu Leu Ser Pro Gln Gln Pro Ala Leu Gln Arg Asn Ser Val Ser
            180                 185                 190

Pro Gly Leu Pro Gln Arg Pro Ala Ser Ala Gly Gly Pro Pro Pro
        195                 200                 205

Thr Ala Ser Gln Pro Ala Ser Val Asn Ile Pro Gly Ser Leu Pro Ser
    210                 215                 220

Ser Thr Pro Tyr Thr Met Pro Pro Glu Pro Thr Leu Ser Gln Asn Pro
225                 230                 235                 240

Leu Ser Ile Met Met Ser Arg Met Ser Lys Phe Ala Met Pro Ser Ser
                245                 250                 255

Thr Pro Leu Tyr His Asp Ala Ile Lys Thr Val Ala Ser Ser Asp Asp
            260                 265                 270

Asp Ser Pro Pro Ala Arg Ser Pro Asn Leu Pro Ser Met Asn Asn Met
        275                 280                 285

Pro Gly Met Gly Ile Asn Thr Gln Asn Pro Arg Ile Ser Gly Pro Asn
    290                 295                 300

Pro Val Val Pro Met Pro Thr Leu Ser Pro Met Gly Met Thr Gln Pro
305                 310                 315                 320

Leu Ser His Ser Asn Gln Met Pro Ser Pro Asn Ala Val Gly Pro Asn
                325                 330                 335
```

```
Ile Pro Pro His Gly Val Pro Met Gly Pro Gly Leu Met Ser His Asn
            340                 345                 350
Pro Ile Met Gly His Gly Ser Gln Glu Pro Pro Met Val Pro Gln Gly
        355                 360                 365
Arg Met Gly Phe Pro Gln Gly Phe Pro Pro Val Gln Ser Pro Pro Gln
    370                 375                 380
Gln Val Pro Phe Pro His Asn Gly Pro Ser Gly Gln Gly Ser Phe
385                 390                 395                 400
Pro Gly Gly Met Gly Phe Pro Gly Glu Gly Pro Leu Gly Arg Pro Ser
                405                 410                 415
Asn Leu Pro Gln Ser Ser Ala Asp Ala Ala Leu Cys Lys Pro Gly Gly
            420                 425                 430
Pro Gly Gly Pro Asp Ser Phe Thr Val Leu Gly Asn Ser Met Pro Ser
        435                 440                 445
Val Phe Thr Asp Pro Asp Leu Gln Glu Val Ile Arg Pro Gly Ala Thr
    450                 455                 460
Gly Ile Pro Glu Phe Asp Leu Ser Arg Ile Ile Pro Ser Glu Lys Pro
465                 470                 475                 480
Ser Gln Thr Leu Gln Tyr Phe Pro Arg Gly Glu Val Pro Gly Arg Lys
                485                 490                 495
Gln Pro Gln Gly Pro Gly Pro Gly Phe Ser His Met Gln Gly Met Met
            500                 505                 510
Gly Glu Gln Ala Pro Arg Met Gly Leu Ala Leu Pro Gly Met Gly Gly
        515                 520                 525
Pro Gly Pro Val Gly Thr Pro Asp Ile Pro Leu Gly Thr Ala Pro Ser
    530                 535                 540
Met Pro Gly His Asn Pro Met Arg Pro Pro Ala Phe Leu Gln Gln Gly
545                 550                 555                 560
Met Met Gly Pro His His Arg Met Met Ser Pro Ala Gln Ser Thr Met
                565                 570                 575
Pro Gly Gln Pro Thr Leu Met Ser Asn Pro Ala Ala Val Gly Met
            580                 585                 590
Ile Pro Gly Lys Asp Arg Gly Pro Ala Gly Leu Tyr Thr His Pro Gly
        595                 600                 605
Pro Val Gly Ser Pro Gly Met Met Met Ser Met Gln Gly Met Met Gly
    610                 615                 620
Pro Gln Gln Asn Ile Met Ile Pro Pro Gln Met Arg Pro Arg Gly Met
625                 630                 635                 640
Ala Ala Asp Val Gly Met Gly Gly Phe Ser Gln Gly Pro Gly Asn Pro
                645                 650                 655
Gly Asn Met Met Phe
            660

<210> SEQ ID NO 27
<211> LENGTH: 1887
<212> TYPE: DNA
<213> ORGANISM: Homo sapiens

<400> SEQUENCE: 27
atggggagga aaaagattca gatccagcga atcaccgacg agcggaaccg acaggtgact     60
ttcaccaagc ggaagtttgg cctgatgaag aaggcgtatg agctgagcgt gctatgtgac    120
tgcgagatcg cactcatcat cttcaaccac tccaacaagc tgttccagta cgccagcacc    180
gacatggaca aggtgctgct caagtacacg gagtacaatg agccacacga gagccgcacc    240
```

-continued

```
aacgccgaca tcatcgagac cctgaggaag aagggcttca acggctgcga cagccccgag    300
cccgacgggg aggactcgct ggaacagagc cccctgctgg aggacaagta ccgacgcgcc    360
agcgaggagc tcgacgggct cttccggcgc tatgggtcaa ctgtcccggc ccccaacttt    420
gccatgcctg tcacggtgcc cgtgtccaat cagagctcac tgcagttcag caatcccagc    480
ggctccctgg tcaccccttc cctggtgaca tcatccctca cggacccgcg gctcctgtcc    540
ccccagcagc cagcactaca gaggaacagt gtgtctcctg gcctgcccca gcggccagct    600
agtgcggggg ccatgctggg gggtgacctg aacagtgcta acggagcctg ccccagccct    660
gttgggaatg ctacgtcag tgctcgggct cccctggcc cctccctgt ggccaatggc       720 aacagcctaa acaaggtcat ccctgccaag tctccacccc cacctaccca cagcacccag    780
cttggagccc ccagccgcaa gcccgacctg cgagtcatca cttcccaggc aggaaagggg    840
ttaatgcatc acttgactga ggaccattta gatctgaaca atgcccagcg ccttggggtc    900
tcccagtcta ctcattcgct caccacccca gtggtttctg tggcaacgcc gagtttactc    960
agccagggcc tccccttctc ttccatgccc actgcctaca acacagccaa cttcacgttg   1020
ccagatgttg gggacttcct ggatgaggtt ctgttcattg agctgcagcg ggaggaagcg   1080
gacaagctag tgaggcagta caacgaggaa ggccgcaagg ctgggccacc ccctgaaaag   1140
cgctttgaca accgaggtgg tggtggcttc cggggccgcg ggggtggtgg tggcttccag   1200
cgctatgaaa accgaggacc ccctggaggc aaccgtggcg gcttccagaa ccgaggggga   1260
ggcagcggtg gaggaggcaa ctaccgagga ggtttcaacc gcagcggagg tggtggctat   1320
agccagaacc gctggggtaa caacaaccgg gataacaaca actccaacaa cagaggcagc   1380
tacaaccggg ctccccagca acagccgcca ccacagcagc ctccgccacc acagccacca   1440
ccccagcagc caccgccacc acccagctac agccctgctc ggaaccccccc aggggccagc   1500 acctacaata gaacagcaa catccctggc tcaagcgcca ataccagcac ccccaccgtc   1560
agcagctaca gccctccaca gccgagttac agccagccac cctacaacca gggaggttac   1620
agccagggct acacagcccc accgcctcca cctccaccac cacctgccta caactatggg   1680
agctacggcg gttacaaccc ggccccctat accccaccgc caccccccac tgcacagacc   1740
taccctcagc ccagctataa ccagtatcag cagtatgccc agcagtggaa ccagtactat   1800
cagaaccagg gccagtggcc gccatactac gggaactacg actacgggag ctactccggg   1860
aacacacagg gtggcacaag tacacag                                       1887
```

<210> SEQ ID NO 28
<211> LENGTH: 629
<212> TYPE: PRT
<213> ORGANISM: Homo sapiens

<400> SEQUENCE: 28

Met Gly Arg Lys Lys Ile Gln Ile Gln Arg Ile Thr Asp Glu Arg Asn
1               5                   10                  15

Arg Gln Val Thr Phe Thr Lys Arg Lys Phe Gly Leu Met Lys Lys Ala
                20                  25                  30

Tyr Glu Leu Ser Val Leu Cys Asp Cys Glu Ile Ala Leu Ile Ile Phe
            35                  40                  45

Asn His Ser Asn Lys Leu Phe Gln Tyr Ala Ser Thr Asp Met Asp Lys
        50                  55                  60

Val Leu Leu Lys Tyr Thr Glu Tyr Asn Glu Pro His Glu Ser Arg Thr
65                  70                  75                  80

```
Asn Ala Asp Ile Ile Glu Thr Leu Arg Lys Lys Gly Phe Asn Gly Cys
                 85                  90                  95
Asp Ser Pro Glu Pro Asp Gly Glu Asp Ser Leu Glu Gln Ser Pro Leu
            100                 105                 110
Leu Glu Asp Lys Tyr Arg Arg Ala Ser Glu Glu Leu Asp Gly Leu Phe
        115                 120                 125
Arg Arg Tyr Gly Ser Thr Val Pro Ala Pro Asn Phe Ala Met Pro Val
130                 135                 140
Thr Val Pro Val Ser Asn Gln Ser Ser Leu Gln Phe Ser Asn Pro Ser
145                 150                 155                 160
Gly Ser Leu Val Thr Pro Ser Leu Val Thr Ser Ser Leu Thr Asp Pro
                165                 170                 175
Arg Leu Leu Ser Pro Gln Gln Pro Ala Leu Gln Arg Asn Ser Val Ser
            180                 185                 190
Pro Gly Leu Pro Gln Arg Pro Ala Ser Ala Gly Ala Met Leu Gly Gly
        195                 200                 205
Asp Leu Asn Ser Ala Asn Gly Ala Cys Pro Ser Pro Val Gly Asn Gly
210                 215                 220
Tyr Val Ser Ala Arg Ala Ser Pro Gly Leu Leu Pro Val Ala Asn Gly
225                 230                 235                 240
Asn Ser Leu Asn Lys Val Ile Pro Ala Lys Ser Pro Pro Pro Pro Thr
                245                 250                 255
His Ser Thr Gln Leu Gly Ala Pro Ser Arg Lys Pro Asp Leu Arg Val
            260                 265                 270
Ile Thr Ser Gln Ala Gly Lys Gly Leu Met His His Leu Thr Glu Asp
        275                 280                 285
His Leu Asp Leu Asn Asn Ala Gln Arg Leu Gly Val Ser Gln Ser Thr
290                 295                 300
His Ser Leu Thr Thr Pro Val Val Ser Val Ala Thr Pro Ser Leu Leu
305                 310                 315                 320
Ser Gln Gly Leu Pro Phe Ser Ser Met Pro Thr Ala Tyr Asn Thr Ala
                325                 330                 335
Asn Phe Thr Leu Pro Asp Val Gly Asp Phe Leu Asp Glu Val Leu Phe
            340                 345                 350
Ile Glu Leu Gln Arg Glu Glu Ala Asp Lys Leu Val Arg Gln Tyr Asn
        355                 360                 365
Glu Glu Gly Arg Lys Ala Gly Pro Pro Glu Lys Arg Phe Asp Asn
370                 375                 380
Arg Gly Gly Gly Phe Arg Gly Arg Gly Gly Gly Gly Phe Gln
385                 390                 395                 400
Arg Tyr Glu Asn Arg Gly Pro Pro Gly Gly Asn Arg Gly Phe Gln
                405                 410                 415
Asn Arg Gly Gly Gly Ser Gly Gly Gly Asn Tyr Arg Gly Gly Phe
            420                 425                 430
Asn Arg Ser Gly Gly Gly Tyr Ser Gln Asn Arg Trp Gly Asn Asn
        435                 440                 445
Asn Arg Asp Asn Asn Ser Asn Asn Arg Gly Ser Tyr Asn Arg Ala
450                 455                 460
Pro Gln Gln Gln Pro Pro Gln Gln Pro Pro Pro Gln Pro Pro
465                 470                 475                 480
Pro Gln Gln Pro Pro Pro Pro Ser Tyr Ser Pro Ala Arg Asn Pro
                485                 490                 495
```

```
Pro Gly Ala Ser Thr Tyr Asn Lys Asn Ser Asn Ile Pro Gly Ser Ser
            500                 505                 510

Ala Asn Thr Ser Thr Pro Thr Val Ser Ser Tyr Ser Pro Pro Gln Pro
        515                 520                 525

Ser Tyr Ser Gln Pro Pro Tyr Asn Gln Gly Gly Tyr Ser Gln Gly Tyr
        530                 535                 540

Thr Ala Pro Pro Pro Pro Pro Pro Pro Ala Tyr Asn Tyr Gly
545                 550                 555                 560

Ser Tyr Gly Gly Tyr Asn Pro Ala Pro Tyr Thr Pro Pro Pro Pro
            565                 570                 575

Thr Ala Gln Thr Tyr Pro Gln Pro Ser Tyr Asn Gln Tyr Gln Gln Tyr
        580                 585                 590

Ala Gln Gln Trp Asn Gln Tyr Tyr Gln Asn Gln Gly Gln Trp Pro Pro
        595                 600                 605

Tyr Tyr Gly Asn Tyr Asp Tyr Gly Ser Tyr Ser Gly Asn Thr Gln Gly
            610                 615                 620

Gly Thr Ser Thr Gln
625
```

<210> SEQ ID NO 29
<211> LENGTH: 684
<212> TYPE: DNA
<213> ORGANISM: Homo sapiens

<400> SEQUENCE: 29

```
atggccctcc cgacaccctc ggacagcacc ctccccgcgg aagcccgggg acgaggacgg    60
cgacggagac tcgtttggac cccgagccaa agcgaggccc tgcgagcctg ctttgagcgg   120
aacccgtacc cgggcatcgc caccagagaa cggctggccc aggccatcgg cattccggag   180
cccagggtcc agatttggtt tcagaatgag aggtcacgcc agctgaggca gcaccggcgg   240
gaatctcggc cctggcccgg gagacgcggc ccgccagaag gccggcgaaa gcggaccgcc   300
gtcaccggat cccagaccgc cctgctcctc cgagcctttg agaaggatcg ctttccaggc   360
atcgccgccc gggaggagct ggccagagag acgggcctcc ggagtccag gattcagatc    420 tggtttcaga tcgaagggc caggcacccg ggacagggtg caggggcgcc cgcgcaggca   480
ggcggcctgt gcagcgcggc cccggcggg ggtcaccctg ctccctcgtg ggtcgccttc    540
gcccacaccg cgcgcgtgggg aacgggggctt cccgcacccc acgtgccctg cgcgcctggg   600
gctctcccac aggggggcttt cgtgagccag gcagcgaggg ccgcccccgc gctgcagccc   660
agccaggccg cgccggcaga gggg                                           684
```

<210> SEQ ID NO 30
<211> LENGTH: 607
<212> TYPE: DNA
<213> ORGANISM: Homo sapiens

<400> SEQUENCE: 30

```
atggggagga aaaagattca gatccagcga atcaccgacg agcggaaccg acaggtgact    60
ttcaccaagc ggaagtttgg cctgatgaag aaggcgtatg agctgagcgt gctatgtgac   120
tgcgagatcg cactcatcat cttcaaccac tccaacaagc tgttccagta cgccagcacc   180
gacatggaca ggtgctgct caagtacacg gagtacaatg agccacacga gagccgcacc   240
aacgccgaca tcatcgagac cctgaggaag aagggcttca acggctgcga cagccccgag   300
cccgacgggg aggactcgct ggaacagagc cccctgctgg aggacaagta ccgacgcgcc   360
```

```
agcgaggagc tcgacgggct cttccggcgc tatgggtcaa ctgtcccggc ccccaacttt    420
gccatgcctg tcacggtgcc cgtgtccaat cagagctcac tgcagttcag caatcccagc    480
ggctccctgg tcacccttc cctggtgaca tcatccctca cggacccgcg gctcctgtcc     540
ccccagcagc cagcactaca gaggaacagt gtgtctcctg gcctgcccca gcggccagct    600
agtgcgg                                                               607
```

<210> SEQ ID NO 31
<211> LENGTH: 1118
<212> TYPE: DNA
<213> ORGANISM: Homo sapiens

<400> SEQUENCE: 31

```
gaatgggcat taatacacag aatcctcgaa tttcaggtcc aaaccccgtg gttccgatgc     60
caaccctcag cccaatggga atgacccagc cactttctca ctccaatcag atgccctctc    120
caaatgccgt gggacccaac atacctcctc atggggtccc aatggggcct ggcttgatgt    180
cacacaatcc tatcatgggg catgggtccc aggagccacc gatggtacct caaggacgga    240
tgggcttccc ccagggcttc cctccagtac agtctccccc acagcaggtt ccattccctc    300
acaatggccc cagtgggggg cagggcagct cccaggaggg gatgggtttc caggagaag    360 gccccccttgg ccgccccagc aacctgcccc aaagttcagc agatgcagca ctttgcaagc    420
ctggaggccc cggggtcct gactccttca ctgtcctggg aacagcatg ccttcggtgt     480 ttacagaccc agatctgcag gaggtcatcc gacctggagc caccggaata cctgagtttg    540
atctatcccg cattattcca tctgagaagc ccagccagac gctgcaatat ttccctcgag    600 ggaagttcc aggccgtaaa cagccccagg gtcctggacc tgggttttca cacatgcagg    660
ggatgatggg cgaacaagcc cccagaatgg gactagcatt acctggcatg ggaggtccag    720
ggccagtggg aactccggac atccctcttg gtacagctcc atccatgcca ggccacaacc    780
ccatgagacc accagccttt ctccaacaag gcatgatggg acctcaccat cggatgatgt    840
caccagcaca atctacaatg cccggccagc ccaccctgat gagcaatcca gctgctgccg    900
tgggcatgat tcctggcaag gatcgggggc ctgccgggc ctacacccac cctgggcctg     960
tgggctctcc aggcatgatg atgtccatgc agggcatgat gggaccccaa cagaacatca   1020 tgatccccc acagatgagg cccgggggca tggctgctga cgtgggcatg ggtggattta   1080
gccaaggacc tggcaaccca ggaaacatga tgttttaa                            1118
```

<210> SEQ ID NO 32
<211> LENGTH: 1006
<212> TYPE: DNA
<213> ORGANISM: Homo sapiens

<400> SEQUENCE: 32

```
atggggagga aaaagattca gatccagcga atcaccgacg agcggaaccg acaggtgact     60
ttcaccaagc ggaagtttgg cctgatgaag aaggcgtatg agctgagcgt gctatgtgac    120
tgcgagatcg cactcatcat cttcaaccac tccaacaagc tgttccagta cgccagcacc    180
gacatggaca aggtgctgct caagtacacg gagtacaatg agccacacga gagccgcacc    240
aacgccgaca tcatcgagac cctgaggaag aagggcttca cggctgcga cagccccgag    300 cccgacgggg aggactcgct ggaacagagc cccctgctgg aggacaagta ccgacgcgcc    360
agcgaggagc tcgacgggct cttccggcgc tatgggtcaa ctgtcccggc ccccaacttt    420
gccatgcctg tcacggtgcc cgtgtccaat cagagctcac tgcagttcag caatcccagc    480
```

```
ggctccctgg tcaccccttc cctggtgaca tcatccctca cggacccgcg gctcctgtcc      540
ccccagcagc cagcactaca gaggaacagt gtgtctcctg gcctgcccca gcggccagct      600
agtgcggggg ccatgctggg gggtgacctg aacagtgcta acggagcctg ccccagccct      660
gttgggaatg ctacgtcag tgctcgggct ccctggcc tctccctgt ggccaatggc         720
```

```
ggctccctgg tcaccccttc cctggtgaca tcatccctca cggacccgcg gctcctgtcc      540
ccccagcagc cagcactaca gaggaacagt gtgtctcctg gcctgcccca gcggccagct      600
agtgcggggg ccatgctggg gggtgacctg aacagtgcta acggagcctg ccccagccct      660
gttgggaatg ctacgtcag tgctcgggct cccctggcc tctccctgt ggccaatggc        720
aacagcctaa acaaggtcat ccctgccaag tctccacccc acctaccca cagcacccag      780
cttggagccc ccagccgcaa gcccgacctg cgagtcatca cttcccaggc aggaaagggg     840
ttaatgcatc acttgactga ggaccattta gatctgaaca atgcccagcg ccttggggtc     900
tcccagtcta ctcattcgct caccacccca gtggtttctg tggcaacgcc gagtttactc     960
agccagggcc tccccttctc ttccatgccc actgcctaca acacag                   1006

<210> SEQ ID NO 33
<211> LENGTH: 2023
<212> TYPE: DNA
<213> ORGANISM: Homo sapiens

<400> SEQUENCE: 33
ccaacttcac gttgccagat gttggggact tcctggatga ggttctgttc attgagctgc      60
agcgggagga agcggacaag ctagtgaggc agtacaacga ggaaggccgc aaggctgggc     120
cacccctga aaagcgcttt gacaaccgag gtggtggtgg cttccggggc cgcggggtg      180
gtggtggctt ccagcgctat gaaaaccgag accccctgg aggcaaccgt ggcggcttcc      240
agaaccgagg ggaggcagc ggtggaggag gcaactaccg aggaggtttc aaccgcagcg      300
gaggtggtgg ctatagccag aaccgctggg gtaacaacaa ccgggataac aacaactcca     360
acaacagagg cagctacaac cgggctcccc agcaacagcc gccaccacag cagcctccgc     420
caccacagcc accaccccag cagccaccgc caccacccag ctacagccct gctcggaacc     480
ccccaggggc cagcacctac aataagaaca gcaacatccc tggctcaagc gccaatacca     540
gcacccccac cgtcagcagc tacagccctc acagccgag ttacagccag ccaccctaca     600
accagggagg ttacagccag ggctacacag ccccaccgcc tccacctcca ccaccacctg     660
cctacaacta tgggagctac gccggtacag accccggcccc ctataccca ccgccacccc    720
ccactgcaca gacctaccct cagcccagct ataaccagta tcagcagtat gcccagcagt     780
ggaaccagta ctatcagaac cagggccagt ggccgccata ctacgggaac tacgactacg     840
ggagctactc cgggaacaca cagggtggca caagtacaca gtagccagtg tgacccagag     900
gctcccggag gccctgccg gcttcctcca ccagcgcctg cctcggcccc tcctctgccc      960
ccgccagatc ccgtggtgct ggggatgggg tcatcccagg gctgcctccc tccagcccac   1020
tgcctcccct ctgaggggct tccttcccct ccatagggcc aggcatttt ttctggattc    1080
aaacaggcaa caatgacctt ttattttctg tttgtcccca cctcccagc cttccacctc    1140
ctgttcttcc taccttcttc cttttgact aaataatccc cacctccctt gatcatacag    1200
tgaggctaca gtgactgagg ggagaatccc ctcctgttca ctctcccaac cctgctccag   1260
cccctcagct tcccagaccc tcatgcagtt ggttgtaaat tctcccagga gctgttttac   1320
tgtctacttt tcaggattaa aaaaaaaatc aaaacttaaa aaaaaaaaag tttaaaagc     1380
aaaatgggga gggggaggaa gcagtgactt tttttggta attatgcgct ttttttaat      1440
ttttagaatt tgtcttttta ctgtgggtgg gctgttgata tttcatcaag ataagcattt    1500
ctttcctgag ttcaggtgac tgaggaagag ccacaaaaca aaacacaaca aaaccaaacc    1560
acagaatcat cttaacccaa acttttata cgatgcccca gttccccata actttgcaca     1620
```

-continued

| | |
|---|---|
| caagcttctg tgttcagttg aattgtaact gcttttgta tttggagaga gtgactattg | 1680 |
| aacttgaaac cttttattcc gggcgtcttg gtagtttctg gtgggattca gtgggtgaga | 1740 |
| gggaagaagg ggaggttggg gggctccttc ccttcagaac ttgaagtttc tcccactgcc | 1800 |
| tcctctccag tggtctccca ggtgccagac ccaaaagctt ttcctacagt gatacccttt | 1860 |
| attttactt cccttgact catatgtttt aacatgattt taacaaactg cacttattaa | 1920 |
| gaaatgtgtt tgccctgttt tgtttggttt cgttttgttt ctttgaata aatgacatgg | 1980 |
| cacctcctag caggaaggaa gcagggttga aaaaaaaaaa aaa | 2023 |

<210> SEQ ID NO 34
<211> LENGTH: 24
<212> TYPE: DNA
<213> ORGANISM: Artificial
<220> FEATURE:
<223> OTHER INFORMATION: Primer

<400> SEQUENCE: 34
ataacggtgt ccttctgttt gcag                                         24

<210> SEQ ID NO 35
<211> LENGTH: 21
<212> TYPE: DNA
<213> ORGANISM: Artificial
<220> FEATURE:
<223> OTHER INFORMATION: Primer

<400> SEQUENCE: 35
gcagagggga tctcccaacc t                                            21

<210> SEQ ID NO 36
<211> LENGTH: 23
<212> TYPE: DNA
<213> ORGANISM: Artificial
<220> FEATURE:
<223> OTHER INFORMATION: Primer

<400> SEQUENCE: 36
cagccagcac tacagaggaa cag                                          23

<210> SEQ ID NO 37
<211> LENGTH: 24
<212> TYPE: DNA
<213> ORGANISM: Artificial
<220> FEATURE:
<223> OTHER INFORMATION: Primer

<400> SEQUENCE: 37
ggcatctgat tggagtgaga aagt                                         24

<210> SEQ ID NO 38
<211> LENGTH: 24
<212> TYPE: DNA
<213> ORGANISM: Artificial
<220> FEATURE:
<223> OTHER INFORMATION: Primer

<400> SEQUENCE: 38
cttctcctta atgtcacgca cgat                                         24

<210> SEQ ID NO 39
<211> LENGTH: 25
<212> TYPE: DNA
<213> ORGANISM: Artificial

```
<220> FEATURE:
<223> OTHER INFORMATION: Primer

<400> SEQUENCE: 39
gatcatgttt gagaccttca acacc                                              25

<210> SEQ ID NO 40
<211> LENGTH: 22
<212> TYPE: RNA
<213> ORGANISM: Artificial
<220> FEATURE:
<223> OTHER INFORMATION: Synthetic

<400> SEQUENCE: 40
acccugugug ucucaguuca ua                                                 22

<210> SEQ ID NO 41
<211> LENGTH: 13
<212> TYPE: PRT
<213> ORGANISM: Homo Sapiens

<400> SEQUENCE: 41

Met Ala Leu Pro Thr Pro Ser Asp Ser Thr Leu Pro Ala
1               5                   10
```

METHOD FOR DETERMINING PRESENCE OR ABSENCE OF SUFFERING FROM MALIGNANT LYMPHOMA OR LEUKEMIA, AND AGENT FOR TREATMENT AND/OR PREVENTION OF LEUKEMIA

CROSS-REFERENCE TO RELATED APPLICATIONS

This application is a 371 of PCT/JP2016/081738, filed Oct. 26, 2016, which claims benefit of Japanese Patent Application No. 2015-210226 filed on Oct. 26, 2015.

TECHNICAL FIELD

The present invention relates to a method for determining whether a subject suffers from, or likely to suffer from malignant lymphoma or leukemia, an agent for treating and/or preventing malignant lymphoma or leukemia, and the like.

BACKGROUND ART

Malignant lymphoma is a malignant neoplasm occurring in lymphoreticular tissue. Malignant lymphoma arises from malignant transformation of cells of the lymphoid lineage and is often found as a swollen lymph node, and infiltration into organs is also observed. Malignant lymphoma is a disease that often develops in elderly people, but also develops commonly in adolescents and young adults. The sites where lymphoma develops are lymph nodes, the spleen, and other sites where lymphoreticular cells locate. Malignant lymphoma is tentatively distinguished from lymphocytic leukemia by the site of occurrence and the tumorigenicity, but both diseases are biologically closely related and it may be difficult to clinically distinguish between the diseases.

Meanwhile, leukemia is a disease in which a hematopoietic cell in the process of differentiation becomes a tumor and clonally proliferates. Leukemia is classified roughly into acute leukemia, which progresses acutely with undifferentiated leukemia blast cells increase, and chronic leukemia, which progresses usually chronically with differentiated leukemia cells increase. Among acute leukemia, in particular, acute lymphoblastic leukemia (ALL) is a disease that develops commonly, regardless of age. While childhood ALL has a relatively good prognosis, adolescent and young adult ALL or elderly ALL responds poorly to chemotherapy and there are almost no effective molecular targeted therapies (Non Patent Literatures 1 and 2).

It is considered that methods of diagnosis and therapies for malignant lymphoma and leukemia have not been sufficiently established and a method of rapid diagnosis and an effective therapy have been eagerly demanded.

CITATION LIST

Non Patent Literature

Non Patent Literature 1: Pulte, D., Gondos, et al., Blood, 2009, 113, pp. 1408-1411.
Non Patent Literature 2: Schafer, E. S. et al., Nat. Rev. Clin. Oncol., 2011, 8, pp. 417-424.

SUMMARY OF INVENTION

Technical Problem

An object of the present invention is to provide a method for determining whether a subject suffers from, or is likely to suffer from malignant lymphoma or leukemia and an agent for treating and/or preventing the disease.

Solution to Problem

The present inventors have found that a fusion mutation of a DUX4 gene and an IGH or IGL gene, overexpression of a DUX4 gene, or a fusion mutation of an MEF2D gene specifically occurs in leukemia patients, by exhaustively analyzing sequences of cDNAs prepared from leukemia cells derived from leukemia patients with a next-generation sequencer. Furthermore, the present inventors have found that an inhibitor of DUX4 suppresses the proliferation of cell lines having the fusion mutation of a DUX4 gene and the overexpression of a DUX4 gene.

The present invention is based on the foregoing findings and encompasses the following aspects.

(1) A method for assisting in determining whether a subject suffers from, or is likely to suffer from malignant lymphoma or leukemia, comprising:

a detection step of detecting at least one of: a fusion mutation of a DUX4 gene and an immunoglobulin heavy chain or immunoglobulin light chain gene; an overexpression of a DUX4 gene; and a fusion mutation of an MEF2D gene in a sample obtained from the subject; and a determination step of determining that the subject suffers from or is likely to suffer from malignant lymphoma or leukemia when at least one of the fusion mutations or the overexpression is detected;

wherein the DUX4 gene encodes a polypeptide consisting of the amino acid sequence set forth in SEQ ID NO: 2 and the fusion mutation of a DUX4 gene and an immunoglobulin heavy chain or immunoglobulin light chain gene is a mutation that forms a fusion gene comprising a part of the DUX4 gene on the 5' terminal side and a part of the immunoglobulin heavy chain or immunoglobulin light chain gene on the 3' terminal side.

(2) The method according to (1) described above, wherein the polypeptide encoded by the fusion gene of a DUX4 gene and an immunoglobulin heavy chain or immunoglobulin light chain gene comprises:

(i) an amino acid sequence comprising: an amino acid sequence comprising amino acids at positions 1 to 300 and lacking amino acids at positions 410 to 424 in the amino acid sequence set forth in SEQ ID NO: 2 on the N-terminal side; and 2 to 100 amino acids derived from an immunoglobulin heavy chain or immunoglobulin light chain gene on the C-terminal side;

(ii) an amino acid sequence having an identity of 90% or more to the amino acid sequence of (i); or (iii) an amino acid sequence modified from the amino acid sequence of (i) by addition, deletion, and/or substitution of one or more amino acids.

(3) The method according to (1) or (2) described above, wherein a gene encoding the amino acid sequence set forth in SEQ ID NO: 2 comprises the nucleotide sequence set forth in SEQ ID NO: 1.

(4) The method according to any one of (1) to (3) described above, wherein the fusion mutation of an MEF2D gene is a mutation that forms a fusion gene comprising a part of the MEF2D gene on the 5' terminal side and a part of the BCL9 gene on the 3' terminal side; and a polypeptide encoded by the fusion gene of an MEF2D gene and a BCL9 gene comprises:

(i) an amino acid sequence comprising amino acids at positions 1 to 200 in the amino acid sequence set forth in SEQ ID NO: 4 on the N-terminal side and amino acids at positions 1100 to 1426 in the amino acid sequence set forth in SEQ ID NO: 6 on the C-terminal side;

(ii) an amino acid sequence having an identity of 90% or more to the amino acid sequence of (i); or (iii) an amino acid sequence modified from the amino acid sequence of (i) by addition, deletion, and/or substitution of one or more amino acids.

(5) The method according to any one of (1) to (3) described above, wherein the fusion mutation of an MEF2D gene is a mutation that forms a fusion gene comprising a part of the MEF2D gene on the 5' terminal side and a part of the HNRNPUL1 gene on the 3' terminal side; and a polypeptide encoded by the fusion gene of an MEF2D gene and an HNRNPUL1 gene comprises:

(i) an amino acid sequence comprising amino acids at positions 1 to 335 in the amino acid sequence set forth in SEQ ID NO: 4 on the N-terminal side and amino acids at positions 563 to 856 in the amino acid sequence set forth in SEQ ID NO: 8 on the C-terminal side;

(ii) an amino acid sequence having an identity of 90% or more to the amino acid sequence of (i); or (iii) an amino acid sequence modified from the amino acid sequence of (i) by addition, deletion, and/or substitution of one or more amino acids.

(6) The method according to any one of (1) to (5) described above, wherein the leukemia is acute lymphoblastic leukemia.

(7) The method according to (6) described above, wherein the acute lymphoblastic leukemia is adolescent and young adult acute lymphoblastic leukemia.

(8) A polypeptide comprising any of amino acid sequences of the following (i) to (iii):

(i) an amino acid sequence comprising: an amino acid sequence comprising amino acids at positions 1 to 300 and lacking amino acids at positions 410 to 424 in the amino acid sequence set forth in SEQ ID NO: 2 encoded by a DUX4 gene on the N-terminal side; and 2 to 100 amino acids derived from an immunoglobulin heavy chain or immunoglobulin light chain gene on the C-terminal side;

(ii) an amino acid sequence having an identity of 90% or more to the amino acid sequence of (i); or (iii) an amino acid sequence modified from the amino acid sequence of (i) by addition, deletion, and/or substitution of one or more amino acids.

(9) The polypeptide according to (8) described above, wherein the amino acid sequence of (i) comprises an amino acid sequence set forth in any of SEQ ID NOs: 10, 12, 14, 16, and 18.

(10) A polynucleotide encoding the polypeptide according to (8) or (9) described above.

(11) A marker for detecting malignant lymphoma or leukemia, consisting of the polypeptide according to (8) or (9) described above or the polynucleotide according to (10) described above.

(12) A kit for detecting malignant lymphoma or leukemia, comprising a primer set comprising a forward primer and a reverse primer for detecting a gene encoding DUX4 consisting of the amino acid sequence set forth in SEQ ID NO: 2 or an antibody that specifically binds to DUX4.

(13) An agent for detecting malignant lymphoma or leukemia, comprising an antibody that specifically binds to DUX4.

(14) A pharmaceutical composition comprising a DUX4 inhibitor as an active ingredient, for treating and/or preventing malignant lymphoma or leukemia in a subject having a fusion mutation of a DUX4 gene and an immunoglobulin heavy chain or immunoglobulin light chain gene and/or an overexpression of a DUX4 gene, wherein the DUX4 gene encodes a polypeptide consisting of the amino acid sequence set forth in SEQ ID NO: 2 and the fusion mutation of a DUX4 gene and an immunoglobulin heavy chain or immunoglobulin light chain gene is a mutation that forms a fusion gene comprising a part of the DUX4 gene on the 5' terminal side and a part of the immunoglobulin heavy chain or immunoglobulin light chain gene on the 3' terminal side.

(15) The pharmaceutical composition according to (14) described above, wherein the inhibitor of DUX4 is at least one agent selected from the group consisting of an inhibitory nucleic acid to DUX4, a neutralizing antibody to DUX4, and a low molecular weight compound.

(16) The pharmaceutical composition according to (15) described above, wherein the inhibitory nucleic acid is siRNA or shRNA.

(17) A polypeptide comprising any of amino acid sequences of the following (i) to (iii):

(i) an amino acid sequence comprising amino acids at positions 1 to 200 in the amino acid sequence set forth in SEQ ID NO: 4 on the N-terminal side and amino acids at positions 1100 to 1426 in the amino acid sequence set forth in SEQ ID NO: 6 on the C-terminal side;

(ii) an amino acid sequence having an identity of 90% or more to the amino acid sequence of (i); or (iii) an amino acid sequence modified from the amino acid sequence of (i) by addition, deletion, and/or substitution of one or more amino acids.

(18) The polypeptide according to (17) described above, wherein the amino acid sequence of (i) comprises an amino acid sequence set forth in any of SEQ ID NOs: 20, 22, 24, and 26.

(19) A polypeptide comprising any of amino acid sequences of the following (i) to (iii):

(i) an amino acid sequence comprising amino acids at positions 1 to 335 in the amino acid sequence set forth in SEQ ID NO: 4 on the N-terminal side and amino acids at positions 563 to 856 in the amino acid sequence set forth in SEQ ID NO: 8 on the C-terminal side;

(ii) an amino acid sequence having an identity of 90% or more to the amino acid sequence of (i); or (iii) an amino acid sequence modified from the amino acid sequence of (i) by addition, deletion, and/or substitution of one or more amino acids.

(20) The polypeptide according to (19) described above, wherein the amino acid sequence of (i) comprises an amino acid sequence set forth in SEQ ID NO: 28.

(21) A polynucleotide encoding the polypeptide according to any of (17) to (20) described above.

(22) A marker for detecting malignant lymphoma or leukemia, consisting of the polypeptide according to any of (17) to (20) described above or the polynucleotide according to (21) described above.

(23) A kit for detecting malignant lymphoma or leukemia, comprising a primer set comprising a forward primer and a reverse primer for specifically detecting the polynucleotide according to (21) described above and/or an antibody that specifically binds to the polypeptide according to any of (17) to (20) described above.

(24) A primer set comprising a forward primer and a reverse primer for specifically detecting a gene encoding a fusion protein of MEF2D and BCL9L, wherein (1) the forward primer consists of nucleotides comprising consecutive 14 to 30 nucleotides in SEQ ID NO: 30 and the reverse primer consists of nucleotides comprising consecutive 14 to 30 nucleotides in a sequence complementary to the sequence set forth in SEQ ID NO: 31; or (2) the forward primer consists of nucleotides comprising a 14 to 30 nucleotide sequence that hybridizes to a nucleic acid consisting of a sequence complementary to the sequence set forth in SEQ ID NO: 30 under stringent conditions and the reverse primer consists of nucleotides comprising a 14 to 30 nucleotide sequence that hybridizes to a nucleic acid consisting of the sequence set forth in SEQ ID NO: 31 under stringent conditions.

(25) A primer set comprising a forward primer and a reverse primer for specifically detecting a gene encoding a fusion protein of MEF2D and HNRNPUL1, wherein (1) the forward primer consists of nucleotides comprising consecutive 14 to 30 nucleotides in SEQ ID NO: 32 and the reverse primer consists of nucleotides comprising consecutive 14 to 30 nucleotides in a sequence complementary to the sequence set forth in SEQ ID NO: 33; or (2) the forward primer consists of nucleotides comprising a 14 to 30 nucleotide sequence that hybridizes to a nucleic acid consisting of a sequence complementary to the sequence set forth in SEQ ID NO: 32 under stringent conditions and the reverse primer consists of nucleotides comprising a 14 to 30 nucleotide sequence that hybridizes to a nucleic acid consisting of the sequence set forth in SEQ ID NO: 33 under stringent conditions.

The specification of the present application encompasses the contents disclosed in JP Patent Application No. 2015-210226, to which the present application claims priority.

Advantageous Effects of Invention

A method according to the present invention makes it possible to determine whether a subject suffers from, or is likely to suffer from malignant lymphoma or leukemia rapidly and easily by detecting a novel marker gene or protein. Moreover, the present invention may provide a pharmaceutical composition for effectively treating and/or preventing malignant lymphoma or leukemia in a subject having a fusion mutation or an overexpression of a DUX4 gene.

BRIEF DESCRIPTION OF DRAWINGS

FIG. 2b shows RNA-seq reads of Example 1 mapped onto the DUX4 locus and expressed as the number of reads per total 1,000,000 reads (RPM). The fusion points from DUX4 to IGH were indicated with arrows. The exon/intron structures of the DUX4 transcripts were illustrated below with the corresponding ID numbers (ENST numbers) in Ensemble transcript database.

DESCRIPTION OF EMBODIMENTS

1. Method for Determining Disease Based on Mutation or Overexpression of DUX4 Gene In one aspect, the present invention relates to a method for assisting in determining whether a subject suffers from, or is likely to suffer from malignant lymphoma or leukemia, comprising: a detection step of detecting a fusion mutation of a DUX4 (Double homeobox 4) gene and an IGH (immunoglobulin heavy chain) or IGL (immunoglobulin light chain) gene and/or an overexpression of a DUX4 gene in a sample obtained from the subject; and a determination step of determining that the subject suffers from or is likely to suffer from malignant lymphoma or leukemia when the fusion mutation or the overexpression is detected.

As used herein, the malignant lymphoma or leukemia is not limited to a particular kind. Examples of the malignant lymphoma include Hodgkin's lymphoma and non-Hodgkin's lymphoma and preferably a malignant lymphoma is B-cell lymphoma. Examples of the leukemia include acute myeloid leukemia (AML), acute lymphoblastic leukemia (ALL), chronic myelogenous leukemia (CML), and chronic lymphocytic leukemia (CLL), etc. and the leukemia is preferably ALL, particularly preferably child or adolescent and young adult (AYA) acute lymphoblastic leukemia, and more preferably adolescent and young adult acute lymphoblastic leukemia (AYA-ALL). As used herein, childhood means subjects aged 0 to 14 years and adolescent and young adult means subjects aged 15 to 39 years.

As used herein, the "subject" may be either of an individual that is suspected to suffering from malignant lymphoma or leukemia, or a normal individual. By applying a method according to the present invention to an individual that is suspected to suffering from malignant lymphoma or leukemia, whether a subject suffers from malignant lymphoma or leukemia can be determined more accurately and, by applying a method according to the present invention to a normal individual, whether a subject suffers from malignant lymphoma or leukemia, or malignant lymphoma or leukemia, or the likelihood that the subject would suffer from malignant lymphoma or leukemia in the future can be determined.

As used herein, the "sample" means a biological sample used in a method according to the present invention. The sample which can be used in the present invention includes, but not limited to, cells or tissues isolated from a living body. Examples of the cells include, for example, peripheral blood cells, lymph and tissue fluids containing cells, hair matrix cells, buccal cells, nasal cavity cells, intestinal tract cells, intravaginal cells, mucosal cells, and expectoration (that may contain alveolus cells or tracheal cells). Examples of the tissues include lesion sites, for example, the lymph node, the bone marrow, the spleen, the thymus, and the liver and, for example, biopsy samples of these tissues may be used.

Figure 6:
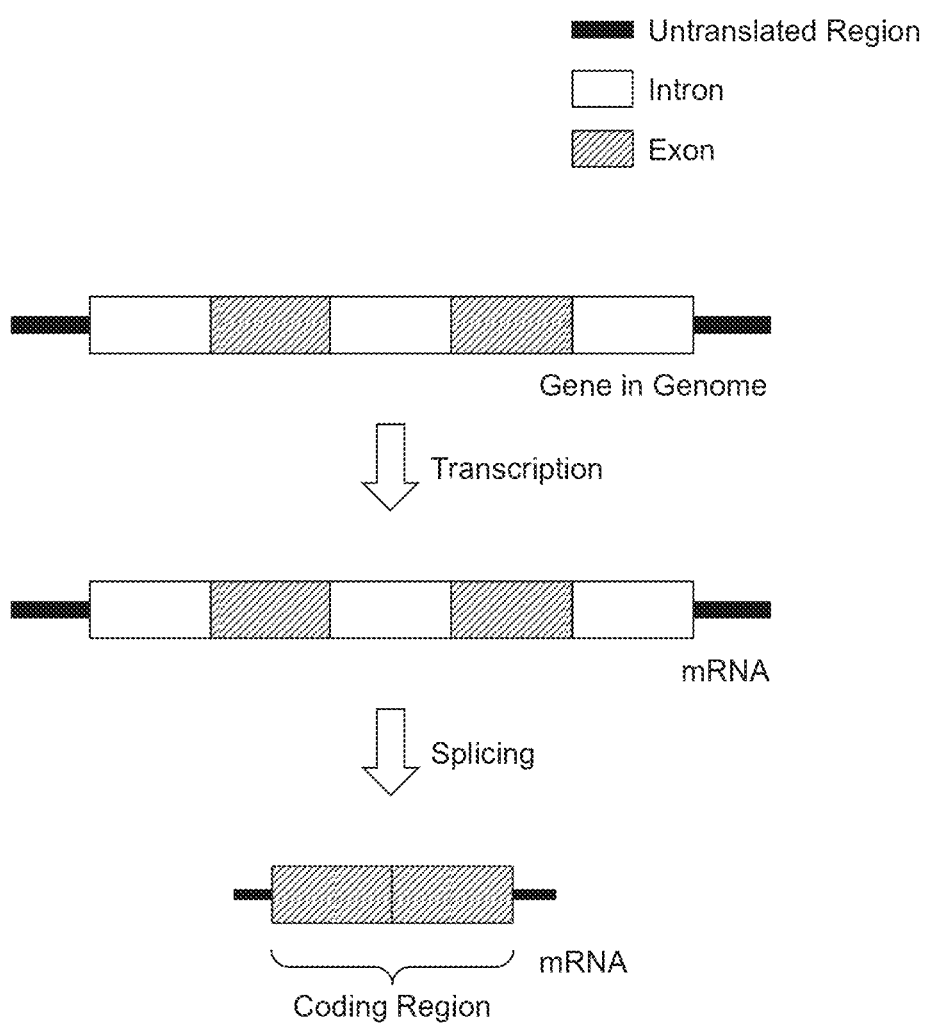
FIG. 6 is a schematic diagram of a gene in the specification. The gene in the genome is transcribed into mRNA and mRNA consisting of the coding region and the untranslated regions is produced by splicing.

As used herein, the "genes" encompass, unless otherwise specified, both coding regions that are transcribed into protein and structural genes (cistrons) encompassing coding regions plus untranslated regions that are not transcribed into protein and intron regions. A schematic diagram of a gene herein is illustrated in FIG. 6. FIG. 6 shows that a gene in the genome is transcribed into mRNA to produce mRNA consisting of coding regions and untranslated regions by splicing.

The detection step of the method according to the present invention involves detecting a fusion mutation of a DUX4 gene and an IGH or IGL gene, preferably a fusion mutation of a DUX4 gene and an IGH gene, and/or an overexpression of a DUX4 gene. The fusion mutations and overexpression detected in the detection step of the method according to the present invention and detection step will be described in detail below.

<Fusion Mutation>

As used herein, the "DUX4 gene" may be a gene encoding a polypeptide containing the amino acid sequence set forth in SEQ ID NO: 2 or an amino acid sequence having, for example, 70% or more, 80% or more, preferably, 90% or more, 95% or more, 97% or more, 98% or more, or 99% or more identity to the amino acid sequence set forth in SEQ ID NO: 2. Moreover, the DUX4 gene may be a gene encoding a polypeptide containing an amino acid sequence modified from the amino acid sequence set forth in SEQ ID NO: 2 by addition, deletion, and/or substitution of one or more amino acids. As used herein, the value of the identity is expressed as a value calculated using a software (for example, FASTA, DANASYS, and BLAST) performing the operation for identity between a plurality of sequences with a default setting. For details of the method for determining the identity, see, for example, Altschul et al, Nuc. Acids. Res. 25, 3389-3402, 1977 and Altschul et al, J. Mol. Biol. 215, 403-410, 1990. Moreover, as used herein, the range of "1 or more" is 1 to 10, preferably 1 to 7, more preferably 1 to 5, particularly preferably 1 to 3 or 1 or 2. The gene encoding the amino acid sequence set forth in SEQ ID NO: 2 preferably contains the nucleotide sequence set forth in SEQ ID NO: 1.

Figure 2A:
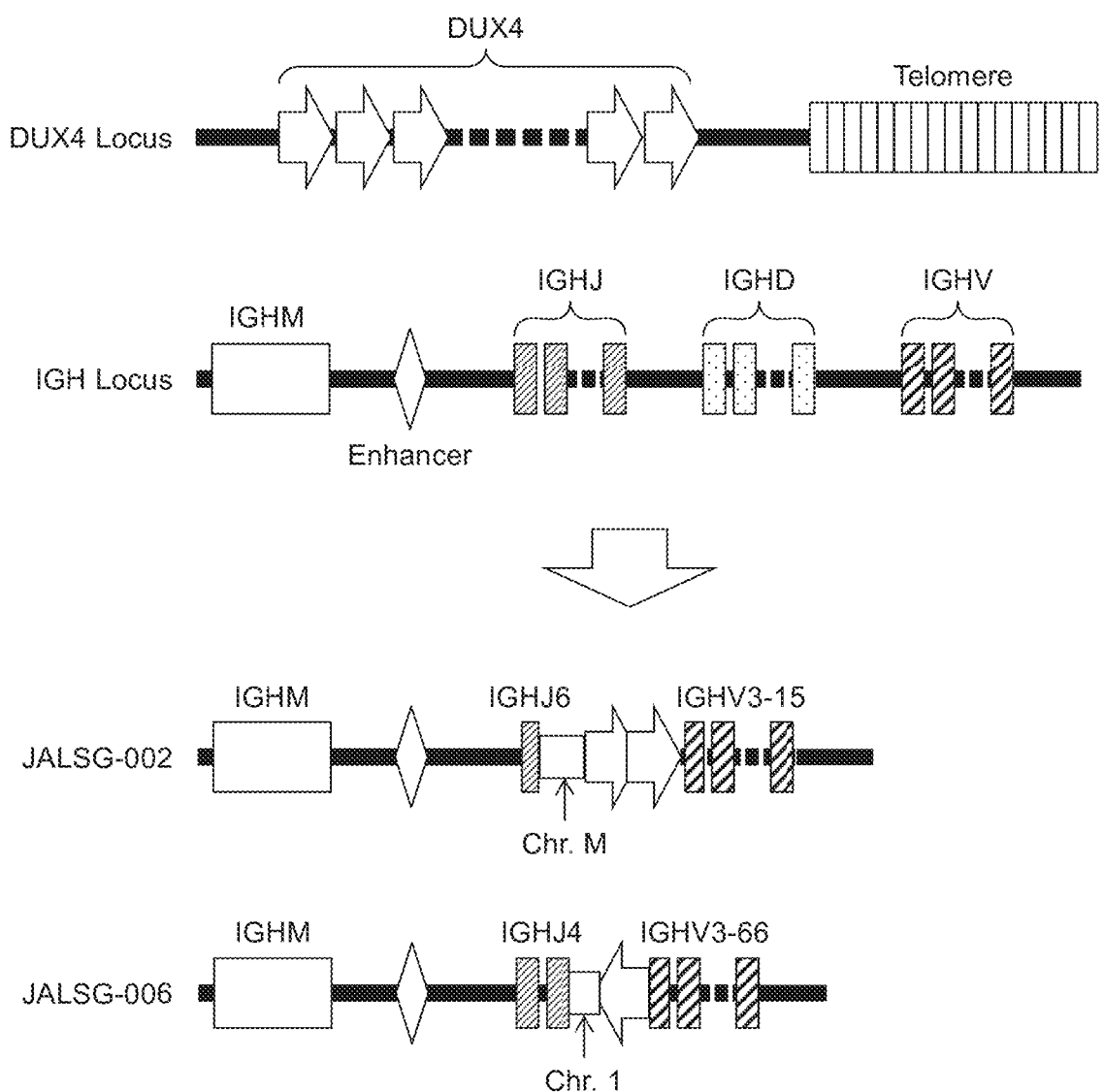
FIG. 2a is a schematic view of an example of the DUX4 translocation in ALL. In the genome of the leukemia blast cells in the patient # JALSG-002, 2 copies of DUX4 having a fragment of mitochondrial genome were inserted between IGHJ6 and IGHV3-15 in the IGH locus. In the patient # JALSG-006, 1 copy of DUX4 was transferred with a fragment of chromosome 1 between IGHJ4 and IGHV3-66. In both reconfigurations, the 3' terminal of DUX4 copies was disrupted. The symbol "Chr." means chromosome.

As used herein, the "fusion mutation of a DUX4 gene and an IGH or IGL gene" means a fusion gene containing a part (preferably 5' terminal side) of the DUX4 gene on the 5' terminal side and a part of the IGH or IGL gene on the 3' terminal side. The fusion mutation of a DUX4 gene and an IGH or IGL gene according to the present invention is generated preferably by the translocation of a partial region of the DUX4 gene to the IGH or IGL locus on genomic DNA as illustrated in FIG. 2a. In this case, the fusion gene contains, from the 5' terminal side to the 3' terminal side, an IGH or IGL gene or a part thereof, a DUX4 gene or a part thereof, and an IGH or IGL gene or a part thereof.

Figure 7:
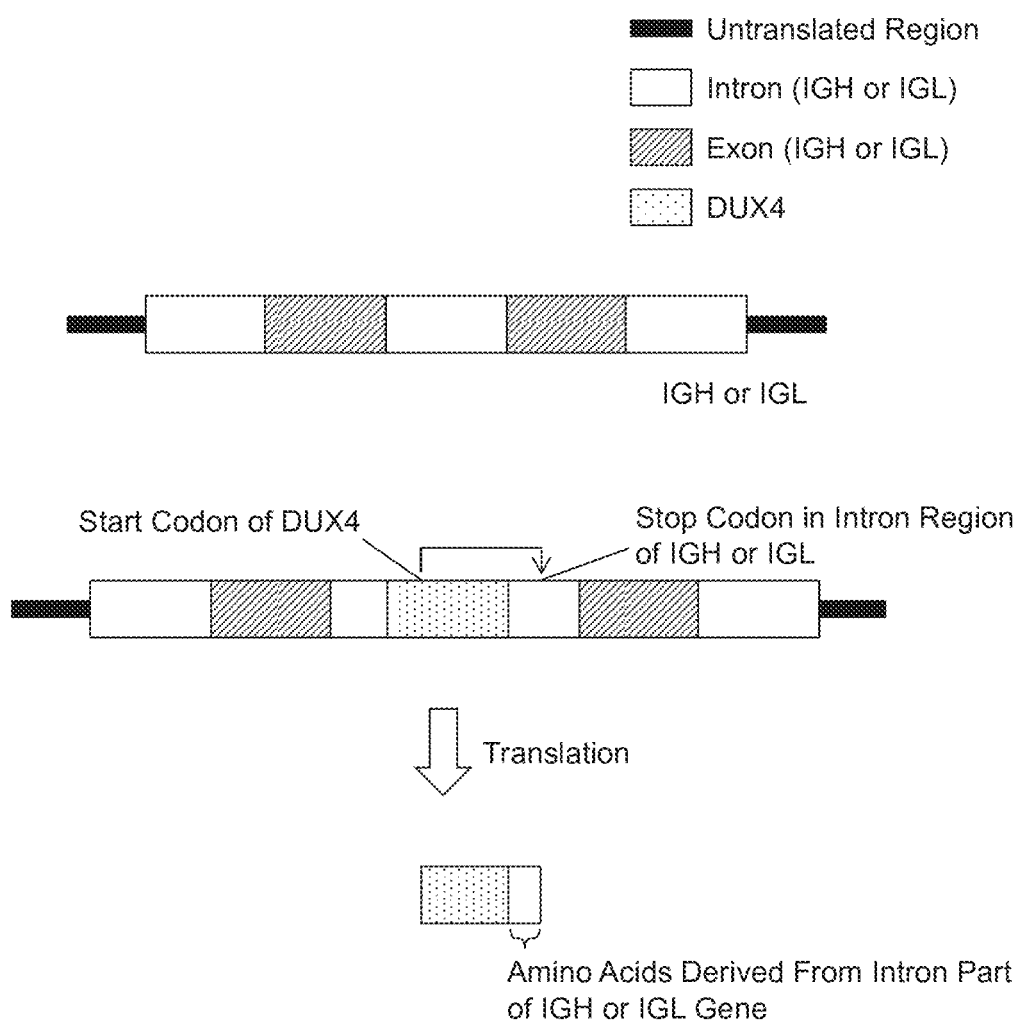
FIG. 7 shows an example when a polypeptide encoded by a fusion gene of a DUX4 gene and an IGH or IGL gene contains amino acids derived from an intron part of an IGH or IGL gene. For simplification, the DUX4 gene was expressed as one region. The figure indicates that when DUX4 is inserted in an intronic part of an IGH or IGL gene and there is a stop codon in the intron part in the open reading frame that continues from DUX4 to the intron of the IGH or IGL, the polypeptide contains an amino acid sequence derived from a nucleotide sequence from a fusion part between DUX4 and the intron to the stop codon.

The polypeptide encoded by the fusion gene of a DUX4 gene and an IGH or IGL gene comprises preferably (i) an amino acid sequence comprising amino acids at positions 1 to 300, preferably positions 1 to 316, in the amino acid sequence set forth in SEQ ID NO: 2 and lacking amino acids at positions 410 to 424, preferably positions 409 to 424, on the N-terminal side and further comprising an IGH or IGL gene, preferably 2 to 100 amino acids, preferably 2 to 32 amino acids, derived from the IGH gene on the C-terminal side. In relation with this, since the IGH or IGL gene is composed of a variety of sequences based on the gene rearrangement, the sequences thereof cannot be determined univocally. As used herein, "comprising an amino acid sequence derived from an IGH or IGL gene" means comprising a sequence encoding a protein of the IGH or IGL gene; or a sequence derived from an intron part of the IGH or IGL gene. The fusion polypeptide "comprising a sequence derived from an intron part of the IGH or IGL gene" means, when the DUX4 gene or a part thereof is inserted in an intron part of the IGH or IGL gene and there is a stop codon in the intron part in an open reading frame following from DUX4 to the intron of IGH or IGL, the polypeptide comprising an amino acid sequence derived from a nucleotide sequence from a fusion part between DUX4 and the intron to the stop codon. An example when a polypeptide encoded by a fusion gene of a DUX4 gene and an IGH or IGL gene contains amino acids derived from an intron part of an IGH or IGL gene is illustrated in FIG. 7. Examples of the amino acid sequence of (i) include amino acid sequences set forth in any of SEQ ID NOs: 10, 12, 14, 16, and 18.

The polypeptide encoded by the fusion gene may comprise (ii) an amino acid sequence having, for example, 70% or more, 80% or more, preferably, 90% or more, 95% or more, 97% or more, 98% or more, or 99% or more identity to the amino acid sequence of (i) described above, or (iii) an amino acid sequence modified from the amino acid sequence of (i) described above by addition, deletion, and/or substitution of one or more amino acids.

The polypeptide encoded by the fusion gene has tumorigenic activity. The presence or absence of tumorigenic activity of a polypeptide can be specified by a known method in the art and determined, for example, by introducing a fusion gene into suitable cells (for example, mammalian cells), growing the cells, and observing the presence or absence of the focus formation. For details of an assay for the presence or absence of tumorigenic activity, see, for example, Example 2 herein.

Without wishing to be bound by theory, in one embodiment, the gene fusion of DUX4 can be involved in the induction of malignant lymphoma or leukemia via at least one of the following three mechanisms: (i) increase of the DUX4 transcriptional activity caused by the translocation of DUX4 to the vicinity of the enhancer of IGH or IGL, (ii) reduction of apoptotic activity by deletion of the carboxy terminal of the encoded DUX4 protein, and (iii) translational activation of the DUX4 gene by a polyadenylation signal derived from IGH or IGL.

<Overexpression>

As used herein, the "overexpression" means expression that is statistically significantly higher than a reference. Examples of the reference include the amount of expression of the gene or protein obtained from a plurality (for example, 3 or more, 4 or more, or 5 or more) of normal subjects known not to suffer from malignant lymphoma or leukemia. The overexpression of DUX4 gene or protein means expression, for example, 2 times or more, 3 times or more, 4 times or more, 5 times or more, for example, 10 times or more as high as the reference.

<Detection Step>

The step of detecting a fusion mutation of a DUX4 gene and an IGH or IGL gene in the method according to the present invention comprises for example, a step of detecting the fusion gene in the genome, mRNA (or cDNA derived from mRNA) expressed from the fusion gene, or a polypeptide encoded by the fusion gene. Similarly, the step of detecting overexpression of a DUX4 gene comprises, for example, a step of detecting mRNA (or cDNA derived therefrom) expressed from the gene or a polypeptide encoded by the gene.

The detection of a gene in the genome may be performed using genomic DNA extracted, for example, by a known method. The extraction of genomic DNA may be performed using a commercially available DNA extraction kit. Moreover, the step of detecting mRNA expressed from the fusion gene may be performed by using mRNA or by using cDNA reverse-transcribed from mRNA extracted from the sample. The extraction and the reverse transcription of mRNA may be performed by using, for example, commercially available mRNA extraction and reverse transcription kits.

The step of detecting the fusion gene in the genome, or mRNA expressed from the fusion gene, or mRNA expressed from a DUX4 gene may be performed according to a known method for gene analysis (for example, PCR assay commonly used as a method for gene detection, RT-PCR, Real-time PCR, LCR (Ligase chain reaction), LAMP (Loop-mediated isothermal amplification), a microarray method, Northern hybridization, dot blotting, in situ hybridization, and an analysis by a next-generation sequencer, and the like). For example, a gene amplification technique using a suitable primer or a hybridization technique with a suitable probe, or the like is used, using a nucleic acid extracted from a sample derived from a subject, for example, mRNA. The detection of a DNA or mRNA in the genome is performed qualitatively or quantitatively and, when performed quantitatively, the amount of DNA or mRNA may be measured, for example, by a method for the gene amplification reaction.

The primer used for detecting the fusion gene or DUX4 gene in this detection step is not particularly limited, as long as they can be used to specifically amplify the fusion gene or DUX4 gene, and can be designed based on a nucleotide sequence of the fusion gene or DUX4 gene or mRNA expressed therefrom. Similarly, the probe used for detecting the fusion gene or DUX4 gene in this detection step is not particularly limited, as long as they can specifically hybridize to the fusion gene or DUX4 gene, and can be designed based on a nucleotide sequence of the fusion gene or DUX4 gene or mRNA expressed therefrom. Examples of the primer and probe that can be used for detecting the fusion gene or DUX4 gene include the primer sets and probes described in "3. Primer, probe, and antibody for detecting mutation or overexpression of DUX4 gene" described below.

The presence or absence of the fusion gene of a DUX4 gene and an IGH or IGL gene can be confirmed by a method suitable for each technology when the sequence of the fusion gene is known. For example, in the PCR method, the presence or absence of the mutation may be detected by analyzing the PCR product by agarose gel electrophoresis and confirming by ethidium bromide staining and the like whether an aimed size of amplification fragment has been obtained. For example, if an amplification fragment having a size corresponding to the fusion gene or mRNA expressed from the fusion gene is obtained, then it is presumed that the fusion gene is present in the sample obtained from the subject. As needed, the amplified fragment may be further sequenced. In this way, the presence or absence of the fusion gene can be detected. Moreover, when the sequence of the fusion gene is not known, the presence or absence of the fusion gene of a DUX4 gene and an IGH or IGL gene can be specified by sequencing the terminal of the DUX4 gene by 3'-RACE in candidate specimens that may contain the fusion of a DUX4 gene and an IGH or IGL gene or exhaustive analysis of cDNAs from cells in the candidate specimens by a next-generation sequencer. The candidate specimens can be specified by, for example, the step of detecting overexpression of the fusion genes described below.

The step of detecting a polypeptide encoded by the fusion gene may be performed by, for example, preparing a lysate derived from a sample obtained from a subject and conducting an immunological assay or an enzyme activity assay and the like for a polypeptide encoded by the fusion gene contained therein using an anti-DUX4 antibody or using an antibody to a polypeptide encoded by the fusion gene. In particular, use of the anti-DUX antibodies described in "3. Primers, probes, and antibodies for detecting mutation or overexpression of DUX4 gene" described below is preferred. Preferably, techniques such as enzyme immunoassay, two-antibody sandwich ELISA, fluorescent immunoassay, radioimmunoassay, Western blotting, and the like using a monoclonal antibody or polyclonal antibody specific to a polypeptide encoded by the fusion gene may be used.

Similarly, the presence or absence of overexpression of the DUX4 gene can be confirmed by a method suitable for each technology. The overexpression of the DUX4 gene can be detected, for example, in Real-time PCR by amplifying a sample obtained from a subject with a fluorescence-labeled primer and comparing the fluorescence intensity with the value of a reference. The overexpression of DUX4 can be detected by, for example, immunostaining cells or tissue with an antibody to DUX4 and detecting the presence or absence of the fluorescence intensity or difference from a reference. Examples of the reference include samples obtained from a plurality (for example, 3 or more, 4 or more, or 5 or more) of normal subjects known not to suffer from malignant lymphoma or leukemia.

The method according to the present invention may be used in combination with other methods (for example, X-ray radiography, endoscopy, and the like). By combining the method with another method of determining a disease or a method of diagnosis, the accuracy of the method of determination according to the present invention can be increased.

2. DUX4 Fusion Polypeptide and Polynucleotide

In one aspect, the present invention relates to a polypeptide comprising (i) an amino acid sequence comprising: an amino acid sequence comprising amino acids at positions 1 to 300, preferably positions 1 to 316, in the amino acid sequence set forth in SEQ ID NO: 2 coded by the DUX4 gene and lacking amino acids at positions 410 to 424, preferably positions 409 to 424 on the N-terminal side; and comprising 2 to 100 amino acids, preferably 2 to 32 amino acids, derived from an IGH or IGL gene on the C-terminal side. Examples of the amino acid sequence of (i) include amino acid sequences set forth in any of SEQ ID NOs: 10, 12, 14, 16, and 18.

In one embodiment, the present invention relates to a polypeptide comprising (ii) an amino acid sequence having, for example, 70% or more, 80% or more, preferably, 90% or more, 95% or more, 97% or more, 98% or more, or 99% or more identity to the amino acid sequence of (i) described above or (iii) an amino acid sequence modified from the amino acid sequence of (i) described above by addition, deletion, and/or substitution of one or more amino acids.

The polypeptide according to the present invention has tumorigenic activity. The presence or absence of the tumorigenic activity of the polypeptide can be specified by a known method in the art and determined, for example, by introducing a fusion gene into suitable cells (for example, mammalian cells), growing the cells, and observing the presence or absence of the focus formation.

The polypeptide according to the present invention can be prepared from, for example, a sample derived from a subject determined to have the fusion gene or from a host cell into which a vector containing the fusion gene or fragment thereof is introduced. The purification of the peptide can be accomplished by performing a known method, for example, ammonium sulfate precipitation, separation by precipitation with an organic solvent (ethanol, methanol, acetone, etc.), chromatography such as ion exchange chromatography, isoelectric chromatography, gel filtration chromatography, hydrophobic chromatography, adsorption column chromatography, affinity chromatography using a substrate, an antibody, or the like, reverse-phase column chromatography, HPLC, and the like, filtration treatment such as microfiltration, ultrafiltration, reverse osmosis, and the like alone or in combination.

In one embodiment, the present invention relates to a polynucleotide encoding a polypeptide according to the present invention. Examples of such a polynucleotide include a polynucleotide comprising: (i) a nucleotide sequence set forth in any of SEQ ID NO: 9, 11, 13, 15, and 17; (ii) a nucleotide sequence having, for example, 70% or more, 80% or more, preferably, 90% or more, 95% or more, 97% or more, 98% or more, or 99% or more identity to the nucleotide sequence of (i) described above; or (iii) a nucleotide sequence modified from the nucleotide sequence of (i) described above by addition, deletion, and/or substitution of one or more nucleotides.

Examples of a method for preparing a polynucleotide according to the present invention include (1) a method using polymerase chain reaction (PCR); (2) a method involving selecting a transformant containing a desired polynucleotide from transformants transformed with a cDNA library; and (3) a method of chemical synthesis. For example, by performing RT-PCR with mRNA extracted from a sample obtained from a subject determined to have the fusion gene, a polynucleotide encoding a fusion polypeptide according to the present invention can be prepared.

Moreover, in one embodiment, the present invention relates to a marker for detecting malignant lymphoma or leukemia, consisting of the polypeptide or polynucleotide.

3. Primers, Probes, and Antibodies for Detecting Mutation or Overexpression of DUX4 Gene In one aspect, the present invention relates to a kit for detecting malignant lymphoma or leukemia. The kit according to the present invention comprises at least one of a primer set comprising a forward primer and a reverse primer for detecting a gene encoding DUX4 consisting of the amino acid sequence set forth in SEQ ID NO: 2, a probe for detecting the gene, and an antibody that specifically binds to DUX4. The kit according to the present invention may comprise 2 or more of the at least one of the primer set, the probe, and the antibody.

The primer set for detecting a gene encoding DUX4 is not particularly limited, as long as it can be used to specifically detect the DUX4 gene and examples thereof include a forward primer and a reverse primer wherein (1) the forward primer consists of nucleotides comprising consecutive 14 to 30 nucleotides, for example 16 to 28 nucleotides, preferably 18 to 26 nucleotides, in SEQ ID NO: 29 and the reverse primer consists of nucleotides comprising consecutive 14 to 30 nucleotides, for example 16 to 28 nucleotides, preferably 18 to 26 nucleotides, in a sequence complementary to the sequence set forth in SEQ ID NO: 29; or (2) the forward primer consists of nucleotides comprising a 14 to 30 nucleotide sequence, for example 16 to 28 nucleotides, preferably 18 to 26 nucleotides, that hybridizes to a nucleic acid consisting of a complementary sequence set forth in SEQ ID NO: 29 under stringent conditions and the reverse primer consists of nucleotides comprising a 14 to 30 nucleotide sequence, for example 16 to 28 nucleotides, preferably 18 to 26 nucleotides, that hybridizes to a nucleic acid consisting of the sequence set forth in SEQ ID NO: 29 under stringent conditions. As used herein, the term "stringent conditions" means conditions in which so-called specific hybrid is formed and no nonspecific hybrid is formed. The stringent conditions can be determined as appropriate, for example, with reference to Green and Sambrook, Molecular Cloning, 4th Ed (2012), Cold Spring Harbor Laboratory Press. Specifically, stringent conditions may be set according to a temperature and a salt concentration contained in a solution in Southern hybridization and a temperature and a salt concentration contained in a solution in the washing step in Southern hybridization. More particularly, examples of the stringent conditions include a sodium concentration of 25 to 500 mM, preferably 25 to 300 mM, and a temperature of 42 to 68° C., preferably 42 to 65° C. More specifically, examples include 5×SSC (83 mM NaCl, 83 mM sodium citrate) at a temperature of 42° C.

The probe for detecting the gene encoding DUX4 is not particularly limited, as long as it can be used to detect the DUX4 gene, and preferably composed of, for example, (1) a polynucleotide that hybridizes to a polynucleotide consisting of at least 14, for example 20, preferably 30, consecutive nucleotide sequence in SEQ ID NO: 29 under stringent conditions, or (2) a polynucleotide that hybridizes to a polynucleotide consisting of a sequence complementary to at least 14, for example 20, preferably 30, consecutive nucleotide sequence in SEQ ID NO: 29 under stringent conditions.

The primer and probe can be prepared by a known method known those skilled in the art, for example but not limited to, a method of chemical synthesis.

The antibody that specifically binds to DUX4 may be a commercially available product or may be prepared by a method known to those skilled in the art. Examples of the antibody include polyclonal antibodies, monoclonal antibodies, chimeric antibodies, single chain antibodies (scFVs), humanized antibodies, fully human antibodies, and antibody fragments such as Fab, Fab', F(ab')2, Fc, Fv, and the like. Preferable examples include polyclonal or monoclonal antibodies.

The antibody according to the present invention, for example, a polyclonal antibody and a monoclonal antibody can be prepared using a target protein or a partial fragment thereof, for example, peptide containing SEQ ID NO: 41 or a cell expressing them, as a sensitized antigen in a method well known to those skilled in the art (E. Harlow et al. (Ed.), "Antibodies: A Laboratory Manual", Cold Spring Harbor Laboratory, 1988).

The polyclonal antibody can be obtained, for example, by administering an antigen such as a DUX4 protein or a fragment thereof and the like to a mammal such as a mouse or a rabbit, collecting blood from the mammal, and purifying the antibody. The method of immunization is well known to those skilled in the art and can be performed, for example, by administering an antigen one or more times. Moreover, the antigen (or a partial fragment thereof) may be dissolved in a suitable buffer solution containing a commonly used adjuvant such as the complete Freund's adjuvant and used to increase the immunogenicity. The method for purifying an antibody is also known for those skilled in the art. For example, the polyclonal antibody may be purified by conducting one or more of centrifugation, precipitation using ammonium sulfate and the like and chromatography, affinity chromatography using, for example, an antigen peptide, and the like.

A method for producing a monoclonal antibody includes the hybridoma method. In the hybridoma method, first, a mammal is immunized in a way similar to the production of a polyclonal antibody. The spleen is subsequently extracted from the immunized animal that has been sensitized to obtain B cells. Then, the B cells were fused with myeloma cells according to a conventional method to generate antibody-producing hybridoma. As a method for fusing cells, any method known for those skilled in the art may be selected and used. The selection of the hybridoma may be performed by culturing cells for a suitable period of time in HAT medium (hypoxanthine, aminopterin, and thymidine-containing medium) according to a conventional method. Next, screening for and cloning of antibody-producing hybridoma of interest are conducted. The screening can be performed by a known method for detecting an antibody such as ELISA and the cloning may be performed by a method known to those skilled in the art such as limiting dilution. Subsequently, obtained hybridoma may be cultured in a suitable culture liquid and a monoclonal antibody can be purified from the culture liquid by salt precipitation, gel filtration, ion exchange chromatography, affinity chromatography, or the like.

The primer set, probe, and antibody described above may have a label detectable by chemical or physical detection means to further facilitate the detection. Examples of the substance used as a label include fluorescent substances, enzymes, radioisotopes, luminescent substances, and the like. Examples of the fluorescent substances include fluorescamine, fluorescein isothiocyanate, and the like, examples of the enzymes include peroxidase, alkaline phosphatase, and the like, examples of the radioisotopes include $^{125}$I, $^{131}$I, $^{3}$H, and the like, and examples of the luminescent substances include luciferin, luminol, derivatives thereof, and the like.

The kit according to the present invention may comprise, for example, a buffer, an enzyme, an instruction, and the like, in addition to the primer set or probe described above.

In one aspect, the present invention relates to an agent for detecting malignant lymphoma or leukemia, comprising an antibody that specifically binds to DUX4. The agent for detecting malignant lymphoma or leukemia according to the present invention may be used as a reagent for sample analysis and the like or for the diagnosis of malignant lymphoma or leukemia.

4. Pharmaceutical Composition Comprising Inhibitor of DUX4

In one aspect, the present invention relates to a pharmaceutical composition comprising a DUX4 inhibitor as an active ingredient, for treating and/or preventing malignant lymphoma or leukemia in a subject having a fusion mutation of a DUX4 gene and an IGH or IGL gene and/or an overexpression of a DUX4 gene.

The inhibitor of DUX4 is not particularly limited, as long as it can inhibit the activity of DUX4, and examples thereof include inhibitory nucleic acids to DUX4, neutralization antibodies to DUX4, and low molecular weight compounds. These inhibitors may be used alone or in combination.

Examples of the inhibitory nucleic acids to DUX4 include nucleic acid aptamers to DUX4 and siRNAs or shRNA to DUX4, preferably siRNAs or shRNAs to DUX4.

As used herein, "siRNA" (small interference RNA) is small double strand RNA consisting of a sense strand (passenger strand) having a nucleotide sequence corresponding to a part of the target gene and an antisense strand thereof (guide strand). As used herein, "shRNA" (short hairpin RNA) refers to a single strand RNA in which the siRNA described above or a sense strand and an antisense strand of a mature double strand miRNA were connected with a short spacer sequence having a suitable sequence. In other words, shRNA forms a hairpin-shaped stem-loop structure as a whole molecule by a sense region and an antisense region forming base-pairing between each other in a molecule to form a stem structure, and a spacer sequence simultaneously forming a loop structure.

Those skilled in the art can design siRNA or shRNA to DUX as appropriate based on the sequence of DUX4. Examples of such a sequence include shRNA containing the sequence set forth in SEQ ID NO: 40. The inhibitory nucleic acid is preferably introduced into a vector and administered to a subject and examples of vectors that can be used for the delivery of the inhibitory nucleic acid include the pLMN vector (Transomic).

The pharmaceutical composition according to the present invention may comprise an active ingredient, for example, an anticancer agent, such as 5-FU (fluorouracil), methotrexate, leucovorin, trastuzumab, and the like, other than the inhibitor of DUX4.

The pharmaceutical composition according to the present invention can be formulated by a method known in the field as a general rule. For example, it can be formulated using a method described in Remington's Pharmaceutical Sciences (Merck Publishing Co. Easton, Pa.). Specific methods of formulation vary depending on the mode of administration. Modes of the administration are roughly classified into the oral administration and the parenteral administration and the mode of administration can be selected as appropriate.

When the pharmaceutical composition according to the present invention is administered orally, a pharmaceutically acceptable carrier may be added.

The "pharmaceutically acceptable carrier" refers to a substance that facilitates the formulation of an agent and the application to the living body is added in a range that does not inhibit or suppress the effect of the active ingredient. Examples thereof include excipients, binders, disintegrators, fillers, emulsifiers, flow additives and modifiers or lubricants.

Examples of the "excipients" include sugar such as monosaccharides, disaccharides, cyclodextrin, and polysaccharides (specifically including, but are not limited to, glucose, sucrose, lactose, raffinose, mannitol, sorbitol, inositol, dextrin, maltodextrin, starch, and cellulose), metal salts (for example, sodium phosphate or calcium phosphate, calcium sulfate, magnesium sulfate), citric acid, tartaric acid, glycine, low, medium, high molecular weight polyethyleneglycol (PEG), Pluronic, or a combination thereof.

Examples of the "binders" include starch paste using starch of corn, wheat, rice, or potato, gelatin, tragacanth, methylcellulose, hydroxypropyl methylcellulose, sodium carboxymethylcellulose, and/or polyvinylpyrrolidone and the like.

Examples of the "disintegrators" include the starch or carboxymethyl starch, cross-linked polyvinylpyrrolidone, agar, alginic acid, or sodium alginate, or a salt thereof.

Examples of the "fillers" include the sugar and/or calcium phosphate (for example, tricalcium phosphate or calcium hydrogen phosphate).

Examples of the "emulsifiers" include sorbitan fatty acid esters, glycerin fatty acid esters, sucrose fatty acid esters, and propylene glycol fatty acid esters.

Examples of the "flow additives and modifiers" and "lubricants" include silicates, talc, stearates, or polyethyleneglycol.

Examples of the dosage form of an oral formulation include solid preparations (including tablets, pills, lingusorbs, capsules, and drops), granules, powdered medicines, powders, solutions, and the like. Furthermore, the solid preparations can be formulated into a dosage form with a coating known in the field, for example, sugar coated tablets, gelatin coated tablets, enteric coated tablets, film coated tablets, double-coated tablets, multilayered tablets, as needed. Either of the specific shape and size of the dosage form is not particularly limited as long as it is in the range of dosage forms known in the field for each dosage form.

When the pharmaceutical composition according to the present invention is parenterally administered, specific examples thereof include administration by injection. When the pharmaceutical composition according to the present invention is administered by injection, the pharmaceutical composition may be prepared as a suspension in which the inhibitor is mixed with a pharmaceutically acceptable solvent and a pharmaceutically acceptable carrier was added to the mixture, as needed.

The "pharmaceutically acceptable solvent" may be any of water or another pharmaceutically acceptable aqueous solution or an oily liquid. Examples of the aqueous solution include physiological saline and isotonic solutions containing glucose or another pharmaceutic aid. Example of the pharmaceutic aid include D-sorbitol, D-mannose, D-mannitol, and sodium chloride, and low-concentrations of non-ionic surfactants (for example, polysorbate 80 (TM), HCO-60), polyoxyethylene sorbitan fatty acid esters, and the like. Example of the oily liquid include sesame oil and soybean oil and may be used in combination with for example, benzyl benzoate or benzyl alcohol as a solubilizing agent. Moreover, a buffer, for example, a phosphate buffer solution, a sodium acetate buffer solution, a soothing agent, for example, hydrochloric acid procaine, a stabilizer, for example, benzyl alcohol, phenol, an antioxidant may be blended.

The injections may be formulated by mixing the inhibitor in combination with a pharmaceutically acceptable excipient, emulsifier, suspension, surfactant, stabilizer, pH regulator, or the like, as appropriate in a unit dose form required in generally accepted pharmaceutical practices.

Examples of injection include intravascular injection, intralymphatic injection, intramuscular injection, intraperitoneal injection, subcutaneous injection, and the like and injection is preferably cardiovascular administration such as intravascular injection or intralymphatic injection, which is systemic administration, but may be a topical administration involving the direct administration into lymphoma.

The content of the active ingredient in the pharmaceutical composition according to the present invention may be an amount that may result in the delivery of the active ingredient to the target site by one time of administration in principle and that has almost or completely no adverse side effects to the subject to which the composition is administered. Such content varies depending on the stage of the disease, the kind of the DUX4 inhibitor, the dosage form of the pharmaceutical composition, the mode of administration, and the like, but is determined as appropriate by a person skilled in the art.

The fusion mutations of the DUX4 gene and overexpression of the DUX4 gene that a subject to which the pharmaceutical composition according to the present invention is administered (subject to which the pharmaceutical composition according to the present invention is to be applied) has are as described in "1. Method for determining disease based on mutation or overexpression of DUX4 gene" described above and therefore not described here.

Examples of the kind of malignant lymphoma and leukemia to be treated and/or prevented with the pharmaceutical composition according to the present invention include the aforementioned Hodgkin's lymphoma and non-Hodgkin's lymphoma for malignant lymphoma and the malignant lymphoma is preferably B-cell lymphoma. Examples thereof for leukemia include the aforementioned acute myeloid leukemia, acute lymphoblastic leukemia, chronic myelogenous leukemia, and chronic lymphocytic leukemia and the leukemia is preferably ALL, particularly preferably childhood or adolescent and young adult (AYA) acute lymphoblastic leukemia, and more preferably adolescent and young adult acute lymphoblastic leukemia (AYA-ALL).

The pharmaceutical composition according to the present invention may be administered to, for example, a subject to which the method according to the present invention, that is, the method for determining whether a subject suffers from, or is likely to suffer from malignant lymphoma or leukemia has been applied. Administration of the pharmaceutical composition according to the present invention to a subject suffering from malignant lymphoma or leukemia is expected to have a therapeutic effect and administration of the pharmaceutical composition according to the present invention to a subject who is likely to suffer from malignant lymphoma or leukemia is expected to have a preventive effect.

5. Method for Treating and/or Preventing Malignant Lymphoma or Leukemia Using DUX4 Inhibitor or Pharmaceutical Composition In one aspect, the present invention relates to a method for treating and/or preventing malignant lymphoma or leukemia in a subject having a fusion mutation of a DUX4 gene and an IGH or IGL gene and/or an overexpression of a DUX4 gene, the method comprising administering the aforementioned DUX4 inhibitor or the aforementioned pharmaceutical composition as an active ingredient.

A method for treatment and/or prevention according to the present invention may preferably be performed to a subject to which the method for determination according to the present invention, that is, the method for determining whether a subject suffers from, or is likely to suffer from malignant lymphoma or leukemia has been applied. That is, administration of the DUX4 inhibitor or the aforementioned pharmaceutical composition to a subject determined to suffer from malignant lymphoma or leukemia by the aforementioned method for determination is expected to have a therapeutic effect and administration of the DUX4 inhibitor or the aforementioned pharmaceutical composition to a subject determined to be likely to suffer from malignant lymphoma or leukemia is expected to have a preventive effect.

The kind of malignant lymphoma and leukemia to be treated and/or prevented by the method according to the present invention is as described above.

6. Method for Determining Disease Based on Mutation of MEF2D Gene

In one aspect, the present invention relates to a method for assisting in determining whether a subject suffers from, or is likely to suffer from malignant lymphoma or leukemia, comprising: a detection step of detecting a fusion mutation of an MEF2D (Monocyte-specific enhancer factor 2) gene in a sample obtained from a subject, and a determination step of determining that the subject suffers from or is likely to suffer from malignant lymphoma or leukemia when the fusion mutation is detected. The fusion mutations detected in this aspect will be described in detail below.

As used herein, the "MEF2D gene" may be a gene encoding a polypeptide containing the amino acid sequence set forth in SEQ ID NO: 4 or an amino acid sequence having, for example, 70% or more, 80% or more, preferably, 90% or more, 95% or more, 97% or more, 98% or more, or 99% or more identity to the amino acid sequence set forth in SEQ ID NO: 4. Moreover, the MEF2D gene may be a gene encoding a polypeptide containing an amino acid sequence modified from the amino acid sequence set forth in SEQ ID NO: 4 by addition, deletion, and/or substitution of one or more amino acids. The gene encoding the amino acid sequence set forth in SEQ ID NO: 4 preferably contains the nucleotide sequence set forth in SEQ ID NO: 3.

As used herein, the fusion mutations of an MEF2D gene are fusion mutations of an MEF2D gene and a BCL9 gene or an MEF2D gene and an HNRNPUL1 gene. As used herein, the "fusion mutations of an MEF2D gene and a BCL9 gene" mean fusion genes containing a part of the MEF2D gene (preferably 5' terminal side) on the 5' terminal side and a part of the BCL9 (B-cell Lymphoma 9) gene (preferably 3' terminal side) on the 3' terminal side. The polypeptides encoded by the fusion genes comprise (i) an amino acid sequence comprising amino acids at positions 1 to 200, preferably positions 1 to 202, in the amino acid sequence set forth in SEQ ID NO: 4 on the N-terminal side and amino acids at positions 1100 to 1426, preferably positions 1055 to 1426, in the amino acid sequence set forth in SEQ ID NO: 6 on the C-terminal side. Examples of the amino acid sequence of (i) include any of SEQ ID NOs: 20, 22, 24, and 26, preferably the amino acid sequence set forth in SEQ ID NO: 20 or 22. The polypeptides encoded by the fusion genes may comprise (ii) an amino acid sequence having, for example, 70% or more, 80% or more, preferably, 90% or more, 95% or more, 97% or more, 98% or more, or 99% or more identity to the amino acid sequence of (i) described above or (iii) an amino acid sequence modified from the amino acid sequence of (i) described above by addition, deletion, and/or substitution of one or more amino acids.

As used herein, the "fusion mutations of an MEF2D gene and an HNRNPUL1 gene" mean fusion genes containing a part of the MEF2D gene (preferably 5' terminal side) on the 5' terminal side and a part of the HNRNPUL1 (Heterogeneous Nuclear Ribonucleoprotein U-Like 1) gene (preferably 3' terminal side) on the 3' terminal side. The polypeptides encoded by the fusion genes comprise (i) an amino acid sequence comprising amino acids at positions 1 to 335 in the amino acid sequence set forth in SEQ ID NO: 4 on the N-terminal side and amino acids at positions 563 to 856 in the amino acid sequence set forth in SEQ ID NO: 8 on the C-terminal side. Examples of the amino acid sequence of (i) include the amino acid sequence set forth in any of SEQ ID NO: 28. The polypeptides encoded by the fusion genes may comprise (ii) an amino acid sequence having, for example, 70% or more, 80% or more, preferably, 90% or more, 95% or more, 97% or more, 98% or more, or 99% or more identity to the amino acid sequence of (i) described above or (iii) an amino acid sequence modified from the amino acid sequence of (i) described above by addition, deletion, and/or substitution of one or more amino acids.

The polypeptides encoded by the MEF2D fusion genes have tumorigenic activity. Methods for determining the presence or absence of the tumorigenic activity of the polypeptide and a detection step of detecting a fusion mutation of a MEF2D gene are as described in "1. Method for determining disease based on mutation or overexpression of DUX4 gene" described above and therefore not described here.

7. MEF2D Fusion Polypeptide and Polynucleotide

In one aspect, the present invention relates to a fusion polypeptide of MEF2D and BCL9. The fusion polypeptides comprise (i) an amino acid sequence comprising amino acids at positions 1 to 200, preferably positions 1 to 202, in the amino acid sequence set forth in SEQ ID NO: 4 on the N-terminal side and amino acids at positions 1100 to 1426, preferably positions 1055 to 1426, in the amino acid sequence set forth in SEQ ID NO: 6 on the C-terminal side. Examples of the amino acid sequence of (i) include any of SEQ ID NOs: 20, 22, 24, and 26, preferably the amino acid sequence set forth in SEQ ID NO: 20 or 22. The polypeptides encoded by the fusion genes may comprise (ii) an amino acid sequence having, for example, 70% or more, 80% or more, preferably, 90% or more, 95% or more, 97% or more, 98% or more, or 99% or more identity to the amino acid sequence of (i) described above or (iii) an amino acid sequence modified from the amino acid sequence of (i) described above by addition, deletion, and/or substitution of one or more amino acids.

In one aspect, the present invention relates to a fusion polypeptide of MEF2D and HNRNPUL1. The fusion polypeptide comprises (i) an amino acid sequence comprising amino acids at positions 1 to 335 in the amino acid sequence set forth in SEQ ID NO: 4 on the N-terminal side and amino acids at positions 563 to 856 in the amino acid sequence set forth in SEQ ID NO: 8 on the C-terminal side. Examples of the amino acid sequence of (i) include the amino acid sequence set forth in any of SEQ ID NO: 28. The polypeptides encoded by the fusion genes may comprise (ii) an amino acid sequence having, for example, 70% or more, 80% or more, preferably, 90% or more, 95% or more, 97% or more, 98% or more, or 99% or more identity to the amino acid sequence of (i) described above or (iii) an amino acid sequence modified from the amino acid sequence of (i) described above by addition, deletion, and/or substitution of one or more amino acids.

The fusion polypeptide has tumorigenic activity. Methods for measuring the presence or absence of the tumorigenic activity of the polypeptide are as described in "1. Method for determining disease based on mutation or overexpression of DUX4 gene" described above and therefore not described here.

In one embodiment, the present invention relates to a polynucleotide encoding the fusion polypeptide. Examples of such a polynucleotide include a polynucleotide comprising: (i) a nucleotide sequence set forth in any of SEQ ID NOs: 19, 21, 23, 25, and 27; (ii) a nucleotide sequence having, for example, 70% or more, 80% or more, preferably, 90% or more, 95% or more, 97% or more, 98% or more, or 99% or more identity to the nucleotide sequence of (i) described above; or (iii) a nucleotide sequence modified from the nucleotide sequence of (i) described above by addition, deletion, and/or substitution of one or more nucleotides.

Methods for preparing the fusion polypeptide and polynucleotide are similar to the method described in "2. DUX4 fusion polypeptide and polynucleotide" and therefore not described here.

In one embodiment, the present invention relates to a marker for detecting malignant lymphoma or leukemia consisting of the polypeptide or polynucleotide.

Since the present inventors have shown that subjects who are positive for a fusion mutation of a MEF2D gene have relatively bad prognosis, an MEF2D fusion polypeptide or polynucleotide can be used as a prognosis marker. Since it is expected that prognosis would be bad, for example, when a fusion mutation of an MEF2D gene is detected, the likelihood of recurrence of malignant lymphoma or leukemia can be reduced by conducting treating or preventing measures such as bone marrow transplantation beforehand.

8. Primers, Probes, and Antibodies for Detecting Mutation of MEF2D Gene

In one aspect, the present invention relates to a primer set comprising a forward primer and a reverse primer for detecting a fusion gene of an MEF2D gene and a BCL9 gene. The primer set is not particularly limited, as long as it can be used to specifically detect the fusion gene and examples thereof include a forward primer and a reverse primer wherein (1) the forward primer consists of nucleotides comprising consecutive 14 to 30 nucleotides, for example 16 to 28 nucleotides, preferably 18 to 26 nucleotides, in SEQ ID NO: 30 and the reverse primer consists of nucleotides comprising consecutive 14 to 30 nucleotides, for example 16 to 28 nucleotides, preferably 18 to 26 nucleotides, in a sequence complementary to the sequence set forth in SEQ ID NO: 31; (2) the forward primer consists of nucleotides comprising a 14 to 30 nucleotide sequence, for example 16 to 28 nucleotides, preferably 18 to 26 nucleotides, that hybridizes to a nucleic acid consisting of a complementary sequence set forth in SEQ ID NO: 30 under stringent conditions and the reverse primer consists of nucleotides comprising a 14 to 30 nucleotide sequence, for example 16 to 28 nucleotides, preferably 18 to 26 nucleotides, that hybridizes to a nucleic acid consisting of the sequence set forth in SEQ ID NO: 31 under stringent conditions.

In one aspect, the present invention relates to a probe for detecting a fusion gene of an MEF2D gene and a BCL9 gene. The probe is not particularly limited, as long as it can be used to detect the fusion gene, and preferably composed of, for example, (1) a polynucleotide that hybridizes to a polynucleotide consisting of at least 7, for example 10, preferably 15 consecutive nucleotide sequence in SEQ ID NO: 30 and at least 7, for example 10, preferably 15 consecutive nucleotide sequence in SEQ ID NO: 31 under stringent conditions; or (2) a polynucleotide that hybridizes to a polynucleotide consisting of at least 7, for example 10, preferably 15 consecutive nucleotide sequence in SEQ ID NO: 30 and at least 7, for example 10, preferably 15 consecutive nucleotide sequence in SEQ ID NO: 31 under stringent conditions.

In one aspect, the present invention relates to a primer set comprising a forward primer and a reverse primer for detecting a fusion gene of an MEF2D gene and an HNRNPUL1 gene. The primer set is not particularly limited, as long as it can be used to specifically detect the fusion gene and examples thereof include a forward primer and a reverse primer wherein (1) the forward primer consists of nucleotides comprising consecutive 14 to 30 nucleotides, for example 16 to 28 nucleotides, preferably 18 to 26 nucleotides, in SEQ ID NO: 32 and the reverse primer consists of nucleotides comprising consecutive 14 to 30 nucleotides, for example 16 to 28 nucleotides, preferably 18 to 26 nucleotides, in a sequence complementary to the sequence set forth in SEQ ID NO: 33; or (2) the forward primer consists of nucleotides comprising a 14 to 30 nucleotide sequence, for example 16 to 28 nucleotides, preferably 18 to 26 nucleotides, that hybridizes to a nucleic acid consisting of a complementary sequence set forth in SEQ ID NO: 32 under stringent conditions and the reverse primer consists of nucleotides comprising a 14 to 30 nucleotide sequence, for example 16 to 28 nucleotides, preferably 18 to 26 nucleotides, that hybridizes to a nucleic acid consisting of the sequence set forth in SEQ ID NO: 33 under stringent conditions.

In one aspect, the present invention relates to a probe for detecting a fusion gene of an MEF2D gene and an HNRNPUL1 gene. The probe is not particularly limited, as long as it can be used to detect the fusion gene, and preferably composed of, for example, (1) a polynucleotide that hybridizes to a polynucleotide consisting of at least 7, for example 10, preferably 15 consecutive nucleotide sequence in SEQ ID NO: 32 and at least 7, for example 10, preferably 15 consecutive nucleotide sequence in SEQ ID NO: 33 under stringent conditions; or (2) a polynucleotide that hybridizes to a polynucleotide consisting of at least 7, for example 10, preferably 15 consecutive nucleotide sequence in SEQ ID NO: 32 and at least 7, for example 10, preferably 15 consecutive nucleotide sequence in SEQ ID NO: 33 under stringent conditions.

The primer and probe can be prepared by a method known to those skilled in the art, for example but not limited to, by a method of chemical synthesis.

In one aspect, the present invention relates to an antibody that specifically binds to a fusion protein of MEF2D and BCL9 or a fusion protein of MEF2D and HNRNPUL1. The kind of and the method for preparing the antibody are similar to those described in "3. Primers, probes, and antibodies for detecting mutation or overexpression of DUX4 gene" described above and therefore not described here. For example, the antibody to the aforementioned fusion protein may be prepared by a method known to those skilled in the art. For example, a mammal is immunized with a protein containing a fusion part and an antibody can be obtained from the serum by any method known to those skilled in the art.

The primer set, probe, and antibody described above may have a label detectable by chemical or physical detection means to further facilitate the detection. Examples of the substance used as a label include fluorescent substances, enzymes, radioisotopes, luminescent substances, and the like. Examples of the fluorescent substances include fluorescamine, fluorescein isothiocyanate, and the like, examples of the enzymes include peroxidase, alkaline phosphatase, and the like, examples of the radioisotopes include $^{125}$I, $^{131}$I, $^{3}$H, and the like, and examples of the luminescent substances include luciferin, luminol, derivatives thereof, and the like.

In one embodiment, the present invention relates to a kit for detecting malignant lymphoma or leukemia comprising at least one of the aforementioned primer set, probe, and antibody. The kit according to the present invention may comprise, for example, a buffer, an enzyme, an instruction, and the like, in addition to the probe or antibody.

In one aspect, the present invention relates to an agent for detecting malignant lymphoma or leukemia, comprising an antibody that specifically binds to a fusion protein of MEF2D and BCL9 or a fusion protein of MEF2D and HNRNPUL1. The agent for detecting malignant lymphoma or leukemia according to the present invention may be used as a reagent for sample analysis and the like or for the diagnosis of malignant lymphoma or leukemia.

9. Pharmaceutical Composition Containing MEF2D Inhibitor

In one aspect, the present invention relates to a pharmaceutical composition for treating and/or preventing malignant lymphoma or leukemia, comprising an MEF2D inhibitor as an active ingredient in a subject having the aforementioned fusion mutation of the MEF2D gene.

The MEF2D inhibitor is not particularly limited, as long as it can inhibit the activity of MEF2D, and examples thereof include inhibitory nucleic acids to MEF2D, neutralizing antibodies to MEF2D, and low molecular weight compounds. These inhibitors may be used alone or in combination.

The constitution other than comprising the MEF2D inhibitor as an active ingredient is similar to "4. Pharmaceutical composition comprising inhibitor of DUX4" described above and therefore not described here.

10. Method for Treating and/or Preventing Malignant Lymphoma or Leukemia Using MEF2D Inhibitor or Pharmaceutical Composition In one aspect, the present invention relates to a method for treating and/or preventing malignant lymphoma or leukemia in a subject having the aforementioned fusion mutation of the MEF2D gene, comprising administering the aforementioned MEF2D inhibitor or the aforementioned pharmaceutical composition to the subject.

A method for treatment and/or prevention according to the present invention may preferably be performed to a subject to which the method for determination according to the present invention, that is, the method for determining whether a subject suffers from, or is likely to suffer from malignant lymphoma or leukemia has been applied.

EXAMPLES

Example 1: Identification of Novel Fusion Gene and Characterization

<Materials and Methods>
Cell Line

Human embryonic kidney (HEK) 293 cells and murine 3T3 fibroblasts were obtained from American type Culture Collection (ATCC) and maintained in Dulbecco's modified Eagle's medium-F12 (DMEM-F12) (Thermofisher) containing 10% fetal bovine serum (FBS) (Thermofisher). B-cell lines (Kasumi-7, Kasumi-9, NALM6, NAGL-1, and CCRF-SB) were purchased from the JCRB cell bank and maintained in RPMI1640 medium (Thermofisher) containing 10% FBS. Unless otherwise specified, cell culturing was conducted similarly in all Examples.

Clinical Specimen

Subjects for screening cohorts or with Ph-positive ALL were used for the study of JALSG. CD19$^+$ B-cell and T-cell fractions were selected from the peripheral blood of normal volunteers by a magnetic beads-purification system (Miltenyi Biotech). Bone marrow CD34$^+$ cells were purchased from Takara Bio. The CD10+ fraction was concentrated from bone marrow mononuclear cells purchased from Takara Bio by a magnetic beads purification system. The validation cohort consisted of 62 patients with B-cell ALL including 5 recurrences. The median age was 24 year old (in a range of 0 to 81 year old). The samples of complete remission were obtained from 34 patients. In addition, this study has obtained informed consents from all patients and been approved by the Ethical Review Board of all participated research institutes including University of Tokyo.

RNA-seq

Complementary RNA was prepared from RNA using NEBNext Ultra Directional RNA Library Prep Kit (New England Biolabs) and subjected to NGS sequencing from the both ends in HiSeq2000/2500 platform (Illumina).

In RNA-seq data, the known fusion genes exhibited the following parameter values in the deFuse analysis; Probability >0.9 and split read count >100. Therefore, Round 1 of screening for fusion genes was conducted with the same parameters as those that give yes for the inframe option (Algorithm A). Subsequently, in the next round of screening, fusion genes were searched for using the probe genes specified with Algorithm A as described above (set forth in the Table below) or already known to be involved in gene fusions, by the following standards; Probability >0.9 or split read count >100 (Algorithm B).

TABLE 1

| IGHJ1-6 | PAX5 | ZNF384 | NUP98 | BCL2 |
|---|---|---|---|---|
| IGHM | RUNX1 | DUX4 | CRLF2 | |
| TRA | PBX1 | MYC | PDGFRB | |
| TRB | CEBP family | TAL1 | JAK2 | |
| TRD | MEF2D | TLX3 | KMT2A | |

The fusion gene candidates specified with Algorithm A or Algorithm B were confirmed by RT-PCR and subsequent sequencing.

For expression profiling by RNA-seq data, paired-end reads were aligned to hg19 human genome assembly using TopHat2. The expression levels of respective RefSeq genes were calculated from read counts mapped using HTSeq and standardized by DESeq2 pipeline. For the clustering analysis, the standardized read counts were further converted by dispersion visualization conversion in DESeq2 and subjected to the hierarchical clustering analysis by the Ward's method. The genes used for the clustering have been defined in Roberts et al., N. Engl. J. Med., 371, pp. 1005-1015 (2014), but slightly modified according to the recent Refseq database.

Reads were mapped onto the DUX4 locus (chr4: 191, 007,101 to 191,011,800) using TopHat2 and the read cover range was calculated by SAMtools to make FIG. 2b. To examine the expression level of DUX4, reads were mapped onto DUX4 cDNA (NM 001293798) by Bowtie 2 and the number of reads was counted by SAMtools. Since there are several tens to several hundred copies of DUX4 are in the human genome, the expression level of DUX4 was estimated from the number of reads per total million reads (RPM) mapped on RNAseq entries. The relative expression of DUX4 and ACTB was also measured for a combination of screening and validation cohorts, normal human tissue (Clontech), and 5 cell lines of B-cell ALL by Taqman RT-PCR analysis (Thermo Fisher Scientific).

Identification of nonsynonymous SNV

The sequence reads with Q value for each base ≥20 were selected from the data set and mapped onto the RNAseq database using the Bowtie2 algorithm. Mismatches were removed when (i) the obtained read contains ≥3 independent mismatches; (ii) they are already listed as a genome change in normal humans in the "1000 genomes" database or the in-house database of the present inventors; or (iii) they are supported by only one strand in the genome. Genetic mutations were annotated by SnpEff. Since no normal cells to be paired were obtained in most subjects, the present inventors examined only the nonsynonymous SNVs that had been already reported in public databases, for example, Catalogue of Somatic Mutations in Cancer, International Cancer Genome Consortium, The Cancer Genome Atlas, and Cancer Cell Line Encyclopedia.

Genome PCR for Amplifying Fusion Points

Genomic DNA was subjected to PCR amplification using the following primers:

```
DUX4-IGH:
                              (SEQ ID NO: 34)
5'-ATAACGGTGTCCTTCTGTTTGCAG-3'
and
                              (SEQ ID NO: 35)
5'-GCAGAGGGGATCTCCCAACCT-3';

MEF2D-BCL9:
                              (SEQ ID NO: 36)
5'-CAGCCAGCACTACAGAGGAACAG-3'
and
                              (SEQ ID NO: 37)
5'-GGCATCTGATTGGAGTGAGAAAGT-3';
and ACTB:
                              (SEQ ID NO: 38)
5'-CTTCTCCTTAATGTCACGCACGAT-3'
and
                              (SEQ ID NO: 39)
5'-GATCATGTTTGAGACCTTCAACACC-3'.
```

<Result>

RNA was isolated from bone marrow mononuclear cells from Ph (Philadelphia chromosome)-negative AYA (adolescent and young adult)-ALL (acute lymphoblastic leukemia) treated with Japan Adult Leukemia Study Group (JALSG) ALL202-U protocol (Hayakawa, F. et al., Blood Cancer J., 4, e252 (2014)) (the screening cohort: 54 individuals with B cells ALL, 18 individuals with T cells ALL, and 1 individual with ALL of unknown lineage). By screening for known fusion genes in ALL based on reverse transcription (RT) polymerase chain reaction (PCR), TCF3-PBX1 was identified in 4 individuals, STIL-TAL1 in 4 individuals, ETV6-RUNX1 in 1 individual, KMT2A-MLLT1 in 1 individual, and KMT2A-AFF3 in 1 individual (STIL-TAL1 was identified in T-cell ALL and the others were identified in B-cell ALL). Furthermore, RNA was isolated from Ph-positive ALL (n=3) and normal volunteers (n=8). These RNA was subjected to RNA-seq and 40.8±4.0 Gbp per individual (mean±SD) of sequence data was obtained. The sequences were also mapped onto 16170±471 genes per sample.

Figure 1A:
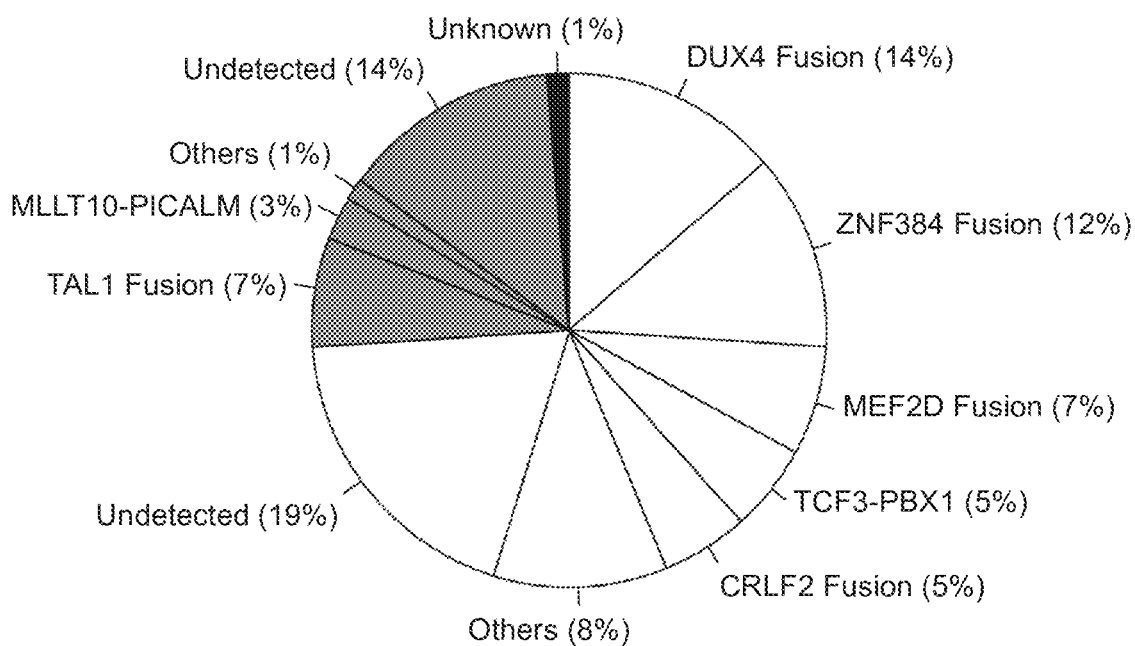
FIG. 1a is a pie graph showing the percentage of each gene fusion to all gene fusions detected in the screening cohort in Example 1. Gene fusions detected in ALLs of B-cell, T-cell, and unknown lineage are indicated with white, gray, and black colors, respectively.

Fusion gene candidates were searched for from the data set using a computer pipeline by the deFuse algorithm (McPherson, A. et al., PLoS Comput. Biol., 7, e1001138 (2011)). In addition to BCR-ABL1, the fused transcription products which were already identified in PCR were successfully detected in correspondent specimens. Furthermore, in 48 AYA-ALL patients, 26 independent fusion genes in total were found and 11 of them were novel (FIG. 1a). The most frequent fusion in AYA-ALL was DUX4, which encodes a protein containing homeobox (n=10, 18.5% of B-cell ALL) and the fusion of MEF2D was also found at high frequency in B-cell ALL. No fusion candidates were identified in 14 patients with B-cell AYA-ALL (25.9%) or 10 patients (55.6%) with T-cell AYA-ALL.

Figure 1B:
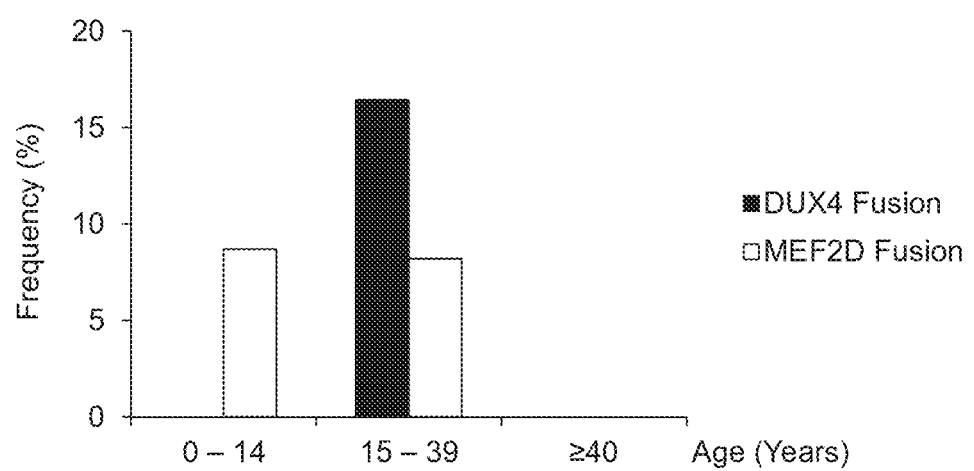
FIG. 1b shows the frequency of DUX4- or MEF2D-fusion genes in the 3 generations (0 to 14 year old (children), 15 to 39 year old (AYA), 40 year old or older) in the combination cohort in Example 1. The screening for fusion genes was performed by RNA-seq in most of children or AYA, and RT-PCR was used in other examples.

Since novel chromosome rearrangement was frequently found in B-cell ALL, further 61 individuals with B-cell ALL in all age groups were analyzed (validation cohort: children (0 to 14 year old) 23 individuals, AYA 19 individuals, ≥40 year old 19 individuals). As illustrated in FIG. 1b, the result of RNA-seq and RT-PCR screening of the screening cohort+validation cohort revealed that the frequencies of DUX4- and MEF2D-fusions are different at particular ages. For example, the DUX4-fusion is found only in the AYA generation (16.4% in both AYA-ALL cohorts). In contrast, the MEF2D-fusion was found at equal frequencies in children and AYA. By RT-PCR screening, none of these fusions was found in the ≥40-year-old specimen.

Figure 1C:
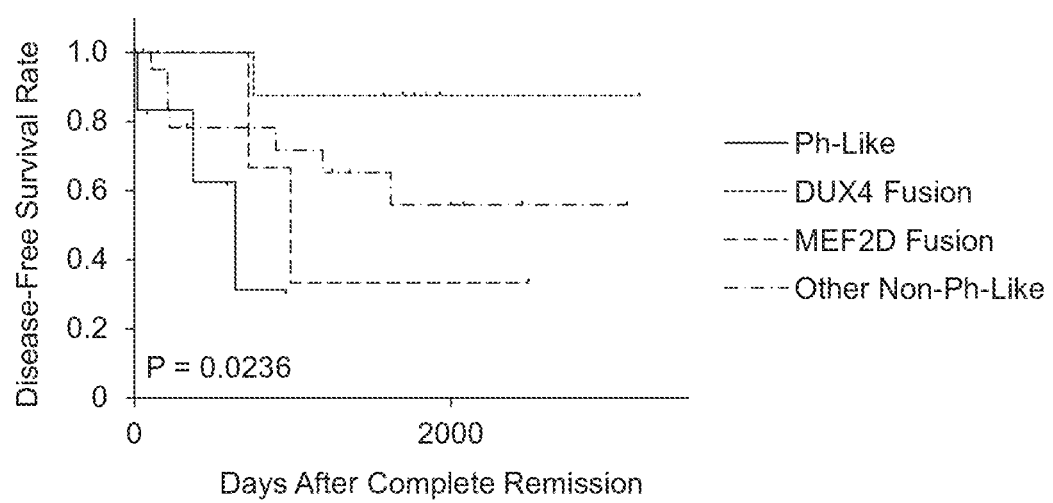
FIG. 1c shows the Kaplan-Meier analysis of the screening cohort in Example 1. The patients were grouped into patients having Ph-like expression profiles, DUX4-fusion genes, MEF2D-fusion genes, or other non-Ph-like profiles. The P value was determined by the Logrank test.

Based on the gene expression profiling, B-cell ALL can be classified into Ph-like or non-Ph-like and the tyrosine kinase pathway is often activated in Ph-like B-cell ALL. The clustering analysis with no objective variable of the screening cohort including cases of Ph-positive ALL was conducted using RNA-seq data and it was revealed that 7 patients with Ph-negative ALL as well as 3 patients with Ph-positive ALL were classified into Ph-like ALL. The clinical result (data not shown) of genetic mutation profiling of the screening cohort has indicated that the gene fusions are mutually exclusive. The DUX4- and MEF2D-fusions were all classified into the non-Ph-like group. However, the effects of these mutations on prognosis of patients are different. Whereas long disease-free survival after complete remission is predicted with ALL having DUX4-gene fusions, the prognosis of the patients having MEF2D-gene fusions was bad similarly to the prognosis of Ph-like ALL (FIG. 1c).

The D4Z4 repeat, in which the DUX4 gene locates, was found to be mainly translocated to the IGH locus in chromosome 14 in the AYA-ALL subset (FIG. 2a). Since the NGS data analysis in the study of the present inventors was an analysis with a mean sequence read length of 104 nucleotides, it was difficult to determine the copy number of DUX4 inserted into the IGH locus. However, the sudden decrease in the number of reads mapped on the DUX4 locus across the fusion point as illustrated in FIG. 2b suggests that several copies of the DUX4 gene were translocated. In fact, the whole translocated part of DUX4 was able to be amplified by PCR from genomic DNA in some cases, where it was determined that the copy number of DUX4 was 1 or 2 (FIG. 2a). Moreover, the absence of DUX4-IGH in the pair specimens at complete remission (data not shown) suggests that such chromosome translocations are mutations that occurred in leukemia cells a posteriori.

Figure 2C:
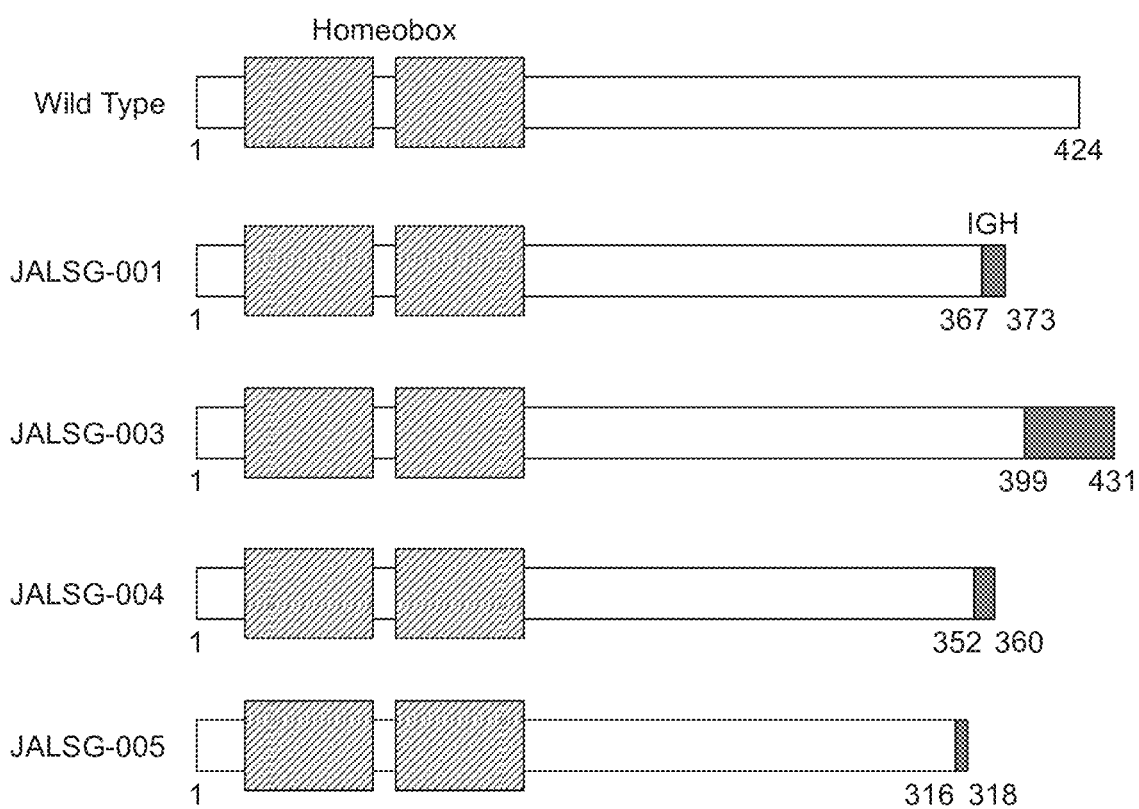
FIG. 2c shows exemplary structures of fusion proteins of DUX4 and DUX4-IGH. The carboxy terminals of the DUX4-IGH fusion proteins found in the patients, # JALSG-001, # JALSG-003, # JALSG-004, or # JALSG-005 were fused with peptides encoded by genomic fragments of IGH. The number of amino acids is indicated under the schematic view of the structures of the proteins.
Figure 2D:
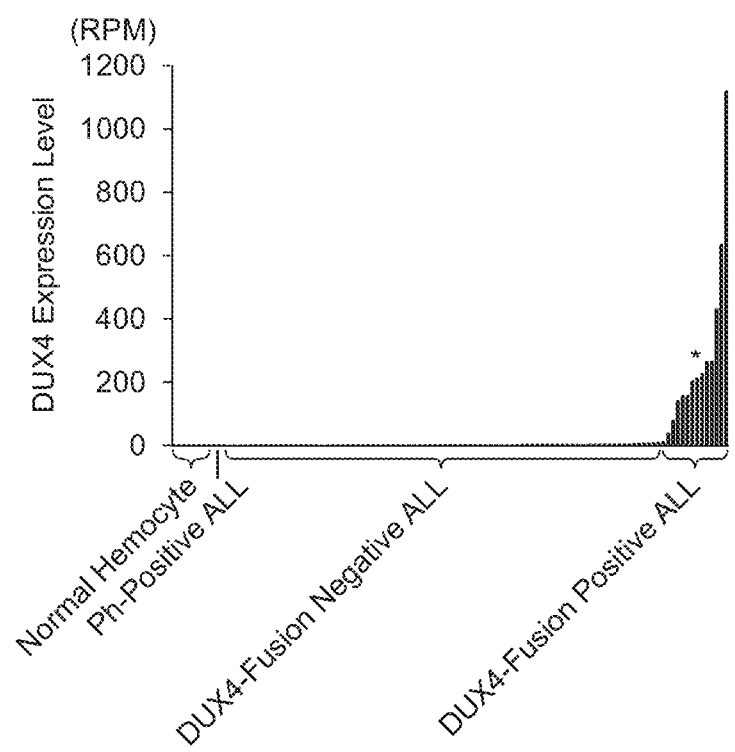
FIG. 2d shows the numbers of reads mapped onto DUX4 cDNA (NM_001293798) calculated from the RNA-seq data of the children and AYA cohorts in Example 1 and expressed as the numbers of mapped reads per total 1,000,000 RefSeq entries (RPM). Normal hemocytes (three T cells and three $CD19^+$ B-cell fractions in the peripheral blood and one $CD10^+$ and $CD34^+$ fraction in the bone marrow) and three $Ph^+$ ALL specimens were analyzed similarly. The presence/absence of Ph or the DUX4 fusion gene is indicated below. The asterisk indicates the NALM6 cell line.

In all cases where DUX4 was translocated, the 3' terminal of the coding region of DUX4 was substituted with an IGH fragment or the like, resulting in DUX4 proteins having a mutant carboxy terminal (FIG. 2c). Moreover, the data of RNA-seq of DUX4 revealed that DUX4 is very strongly expressed only in fusion-positive cases (FIG. 2d).

Example 2: In Vitro Functional Analysis of Fusion Genes

<Materials and Method>

To identify the 3' terminal of DUX4-IGH mRNA, rapid amplification of cDNA ends (RACE) was performed by SMARTer RACE 5'/3' kit (Takara Bio) according to the instructions of the manufacturer. Full length cDNAs encoding DUX4-IGH, MEF2D-BCL9, or MEF2D-HNRNPUL1 were amplified by PCR from specimens from patients and confirmed by Sanger sequencing. They were then ligated with the retroviral vector pMXS (Cell Biolabs), the expression vector pcDNA3.1 (Thermofisher), or the vector pMSCV-ires-GFP and the cDNAs and GFP were expressed simultaneously. To express the wildtype DUX4, the vector pMSCV-GFP-ires, with which the translation of DUX4 is controlled by the ires fragment, was used (Tsuzuki, S. & Seto, M., Stem Cells 31, 236-247 (2013)).

The MEF2 reporter plasmid was purchased from Qiagen. A human MMP7 promoter region (Corveleyn, A. et al., J. Cell. Biochem. 94, 1112-1125 (2005)) was amplified by PCR from human genomic DNA and ligated to the luciferase vector pGL3 (Promega). 100 ng of the reporter plasmid, 200 ng of the expression vector, and 4 ng of pGL-TK (Promega) were transfected into HEK293T cells using Lipofectamine LTX reagent (Thermofisher). 48 hours later, the cells were lysed and the luciferase activity was measured. The reporter activity based on the firefly luciferase was standardized with the activity of *Renilla* luciferase.

For the focus formation assay, recombinant retroviruses were produced by introducing a pMXS- or pMSCV-based expression vector and ecotropic packaging plasmid (Takara Bio) into HEK293T cells. 3T3 cells were infected with the recombinant retroviruses and the cells were then cultured for 2 weeks in DMEM-F12 (Thermofisher) supplemented with 5% bovine serum (Thermofisher).

Expression vectors for various cDNAs were transiently transduced into HEK293T cells using Lipofectamine LTX and the cells were lysed 2 days later. The immunoblot analysis was performed using antibodies to DUX4 (ab124699) or MEF2D (ab93257) (both from Abcam). The cell lysates were also analyzed by immunoblotting with an antibody to ACTB (#4967, Cell Signaling Technology).

A shRNA expression vector was constructed using the vector pLMN (Transomic). The sequence of shRNA to DUX4-IGH is 5'-ACCCUGUGUGUCUCAGUUCAUA-3' (SEQ ID NO: 40) and this targets an IGH region in the transcript of a DUX4-IGH fusion gene in NALM6.

<Result>

Figure 3A:
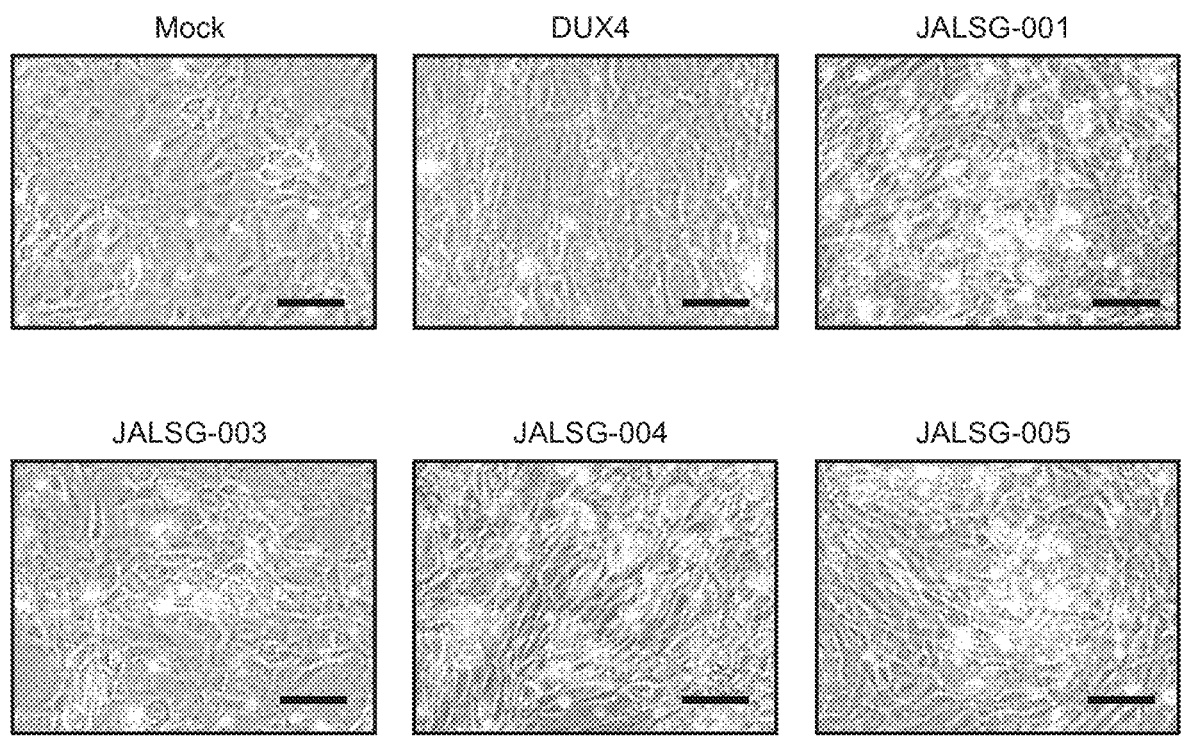
FIG. 3a shows the transformation ability of DUX4-IGH. Using recombinant retroviruses, 3T3 cells were transformed with DUX4 or DUX4-IGH genes identified in the patient # JALSG-001, # JALSG-003, # JALSG-004, or # JALSG-005 and these cells were subsequently cultured in 5% bovine serum for 12 days. Cells infected with retrovirus expressing no DUX4-IGH (Mock) were similarly analyzed. The scale bar is 100 μm.

To examine the relation of DUX4-IGH fusion genes with cancer, the wildtype DUX4 or DUX4 fusion genes were expressed in murine 3T3 fibroblasts and the focus formation assay was performed. As illustrated in FIG. 3a, all the fibroblasts into which DUX4-fusion genes were introduced were transformed to exhibit the oncogenic activity, but the fibroblasts into which the wild type DUX4 was introduced did not exhibit the oncogenic activity.

Figure 3B:
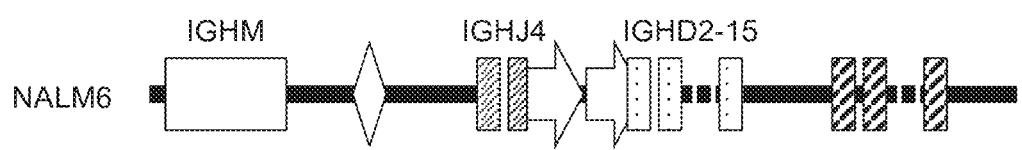
FIG. 3b A shows that 2 copies of DUX4 were transferred to a position between IGHJ4 and IGHD2-15 in the genome of the NALM6 cell. B shows a protein encoded by DUX4-IGH fusion gene. In this protein, carboxy terminal of the DUX4 protein was substituted with 25 amino acids encoded by IGH. C shows the result of immunoblotting whole cell lysates of NALM6 transiently expressing DUX4-IGH or wild type DUX4 or HEK293 with an antibody to DUX4 or ACTB.
Figure 3B:
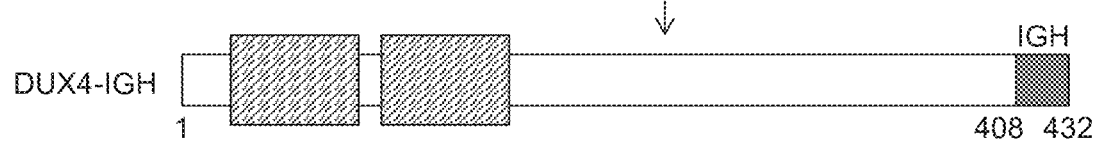
Figure 3B:
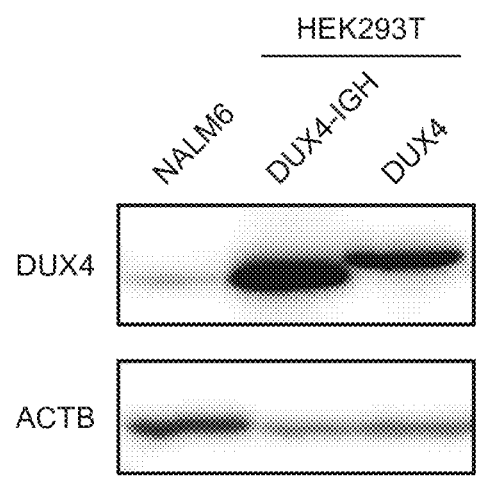
Figure 3C:
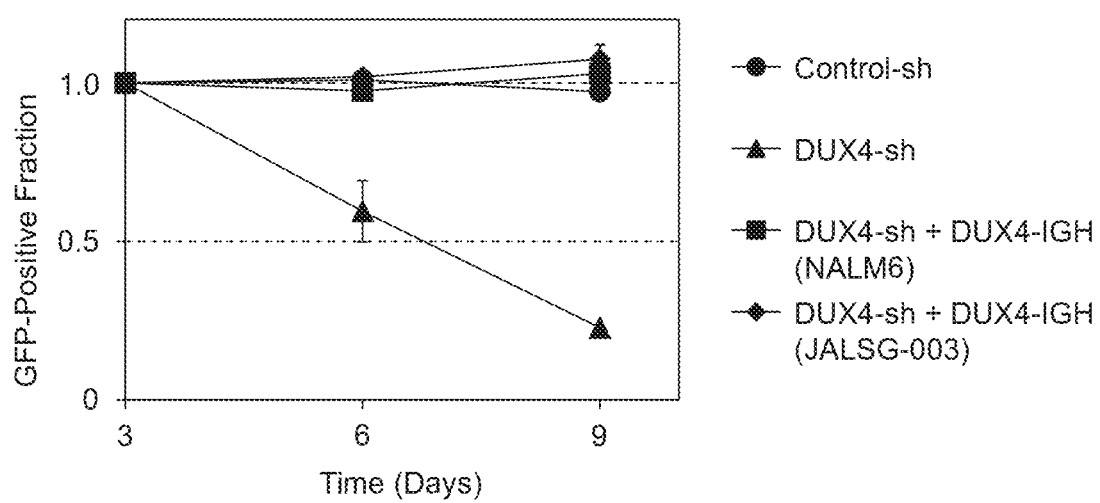
FIG. 3c NALM6 cells were infected with the recombinant retroviruses that express GFP with a control shRNA (control-sh) or DUX4-IGH shRNA (DUX4-sh) together with a virus that expresses DUX4-IGH identified in NALM6 or the patient # JALSG-003 (DUX4-sh+DUX-IGH (NALM6) or DUX4-sh+DUX-IGH (JALSG-003), respectively). The ratio of the $GFP^+$ fraction was tested by flow cytometry and standardized by the ratio on Day 3. The data are the mean±SD in a triplicate test.

RNA-seq of total 5 cell lines with B-cell ALL revealed high expression of DUX4 in NALM6 established from a male aged 19 years (FIG. 2d). Screening for fusion genes confirmed that the NALM6 cell line actually had DUX4-IGH (FIG. 3b). Similar to the clinical specimens, the fusion with IGH resulted in a DUX4 protein having a mutant carboxy terminal and the expression thereof was confirmed by the immunoblotting analysis. This rearrangement locates the polyadenylation signal in IGHD2-15 in the vicinity of the DUX4 protein-coding region. The knockdown of the DUX4 fusion with short hair pin RNA (shRNA) suppressed the proliferation of the NALM6 cells ($P=1.22\times10^{-7}$, Welch's t test), but such an effect was not found when shRNA-resistant DUX4-IGH was co-expressed, which indicates that DUX4 can be a therapy target (FIG. 3c). Moreover, the proliferation suppression by the DUX4-IGH-shRNA was not found in the fusion-negative B-cell line CCRF-SB (data not shown).

Figure 4A:
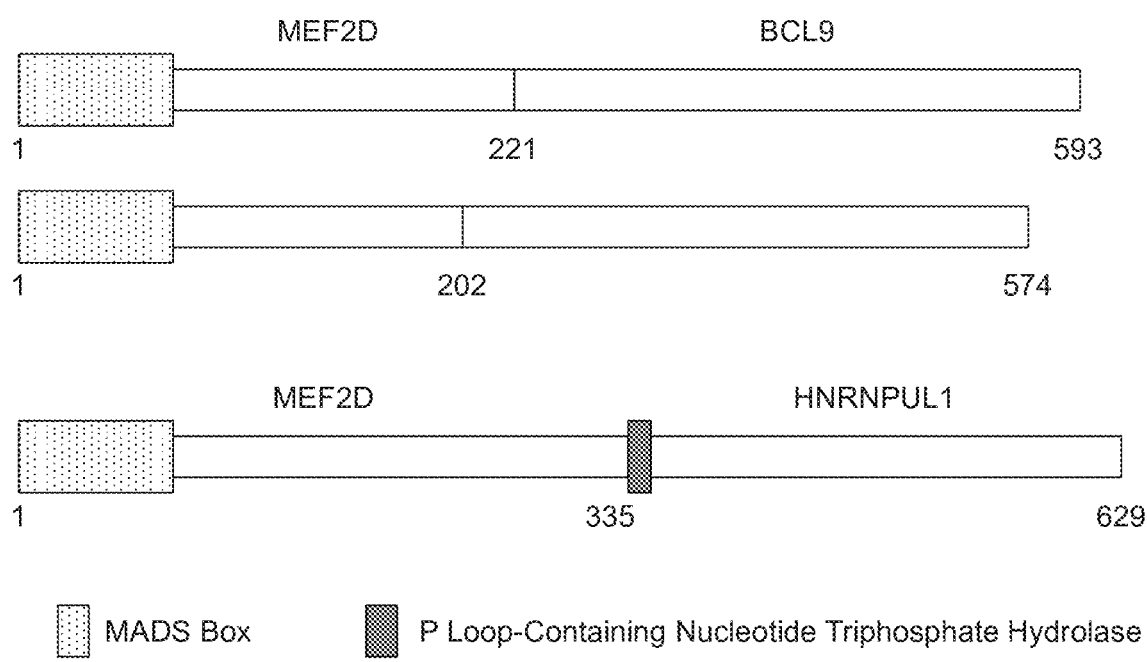
FIG. 4a shows examples of MEF2D fusion detected in the cohort in Example 1. The number of amino acids is indicated under the schematic view of the structure of proteins.

MEF2D-BCL9 and MEF2D-HNRNPUL1 were found in 2 individuals and 3 individuals respectively in the AYA-ALL cohort of the present invention (FIG. 4a). Moreover, it was proved that MEF2D-BCL9 fusion genes derived from the rearrangement of the somatic cell genome (data not shown).

Figure 4B:
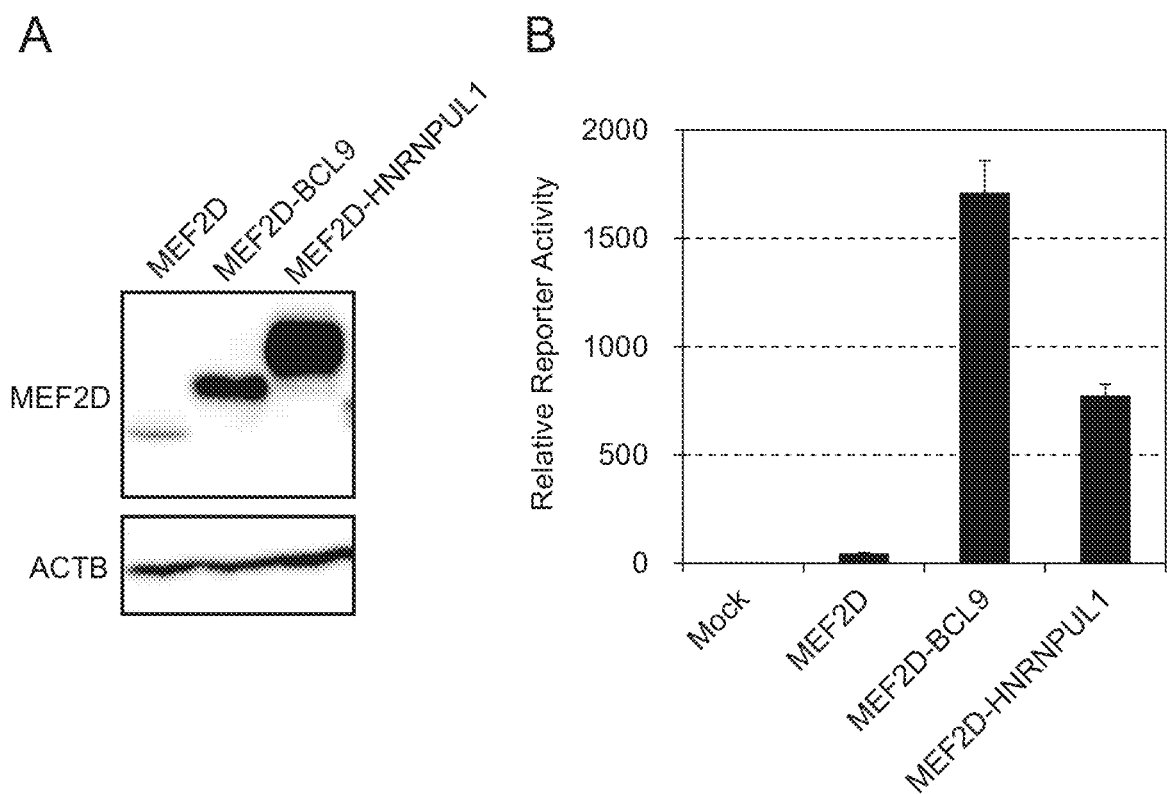
FIG. 4b shows that an MED2D fusion is a gain of function mutation. Whole cell lysates prepared from HEK293 cells transfected with expression vectors of the wildtype MEF2D, MEF2D-BCL9, or MEF2D-HNRNPUL1 were subjected to the immunoblotting analysis with an antibody to MEF2D (upper panel) or ACTB (lower panel) (A). A reporter plasmid of MEF2D was transiently introduced into HEK293 cells with the control pGL-TK and a Mock plasmid or an expression vector of the wild type MEF2D, MEF2D-BCL9, or MEF2D-HNRNPUL1. The reporter activity was measured 2 days after transfection. The firefly luciferase activity was standardized with the *Renilla* luciferase activity. The value is mean±SD.
Figure 4C:
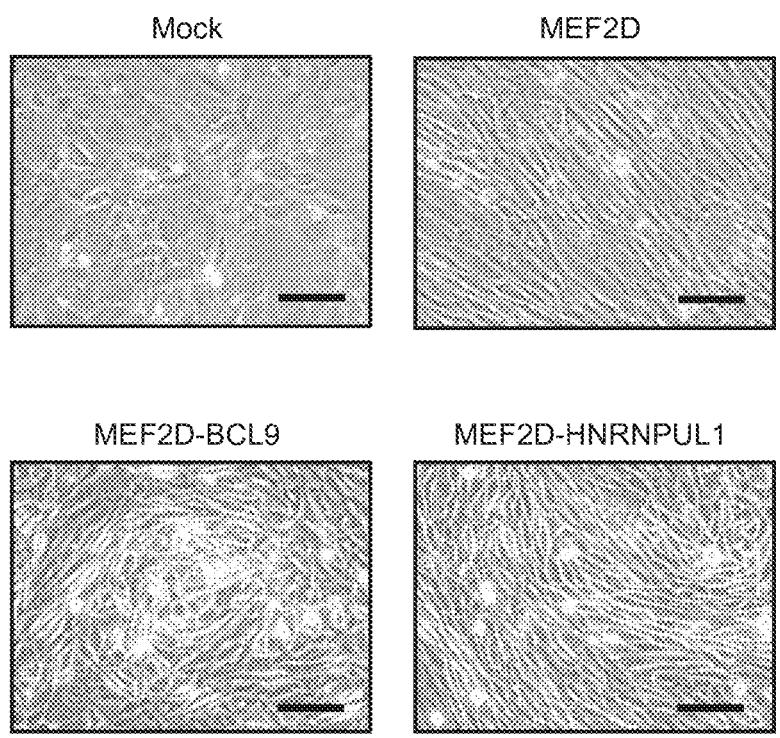
FIG. 4c shows the transformation ability of MEF2D fusion proteins. Murine 3T3 fibroblasts were infected with a Mock virus (Mock) or a recombinant retrovirus expressing the wild type MEF2D, MEF2D-BCL9, or MEF2D-HNRN-PUL1, cultured in the presence of 5% bovine serum for 12 days and observed. The scale bar is 100 μm.

Both MEF2D-BCL9 and MEF2D-HNRNPUL1 proteins had high transcriptional activity relative to the corresponding wild type protein (FIG. 4b). In the test of the oncogenic ability thereof in 3T3 cells, the cells expressing the fusion proteins exhibited a plurality of abnormal focuses, but no abnormal focuses were found with those expressing the wildtype protein (FIG. 4c).

Example 3: In Vivo Functional Analysis of Fusion Genes

<Materials and Methods>

As described before (Tsuzuki, S. et al., Stem Cells, 2013, 31, 236-247), B220+c-kit+pro-B cells were induced from fetus hepatocytes cultured on OP9 cells in Iscove's modification Dulbecco medium (Thermofisher) supplemented with 15% FBS, Stem cell factor, flt3 ligand, interleukin-7, and 2-mercaptoethanol.

These cells were infected with the recombinant retroviruses that express a fusion gene and improved GFP. The obtained GFP-positive cells were inoculated with NSG mice (Jackson Laboratory) exposed to a sublethal dose (2 grays) of radiation. 28 days after the transplant, the expression of CD19, CD43, c-kit, CD25, IL7Ra, or IgM on the cell surface of B220$^+$ GFP$^+$ cells among the (primary) bone marrow cells was evaluated with a flow cytometer. For the flow cytometry analysis, the following antibodies: anti-B220 (RA3-6B2), anti-CD19 (1d3), anti-c-kit (2B8), anti-CD43 (S7), anti-CD25 (PC61.5), and anti-IgM (II/41) antibodies were used. All antibodies except S7, which was purchased from BD Biosciences, were obtained from eBioscience. All animal experiments were conducted following the approved protocols by Institutional Animal Care and Use Committee at Aichi Cancer Center and Nagoya University.

<Result>

Figure 5A:
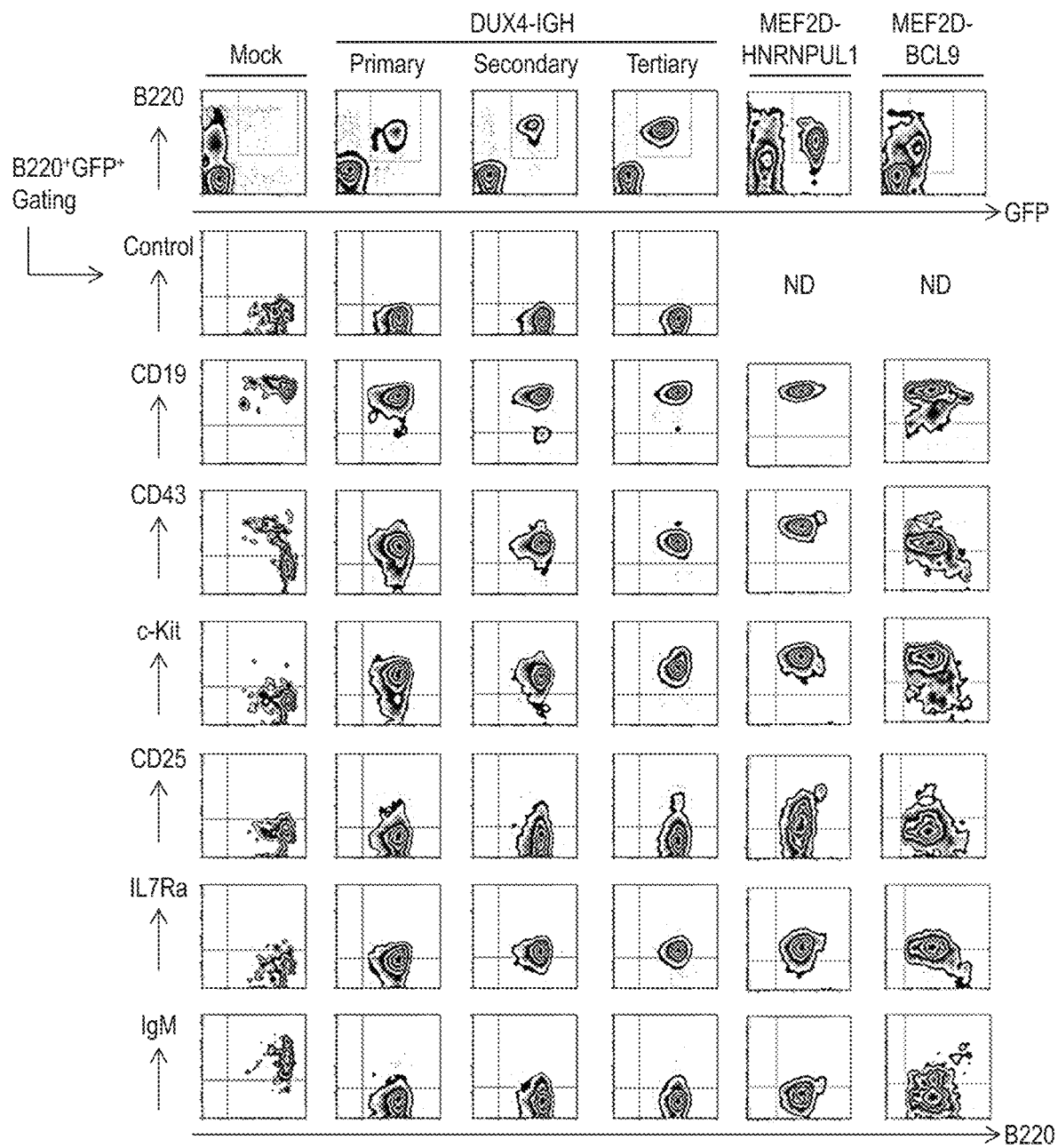
FIG. 5a shows the leukemogenesis activity of fusion oncogenes. Murine pro-B cells were infected with a Mock retrovirus or a recombinant virus expressing DUX4-IGH, MEF2D-HNRNPUL1, or MEF2D-BCL9 and transplanted into immunodeficiency mice exposed to radiation. 28 days after the transplant, expression of CD19, CD43, c-kit, CD25, IL7Ra, or IgM on the cell surface of B220$^+$ GFP$^+$ cells among (primary) bone marrow cells was evaluated with a flow cytometer. The B220$^+$ GFP$^+$ gating in the figure means that B220$^+$ GFP$^+$ cells were used for the analysis and the abscissa axis indicates the expression intensity of B220 and the ordinate axis indicates the expression intensity of each protein indicated on the left edge. The same experiment was performed with secondary or tertiary transplant mice. ND means not determined.

DUX4-IGH fusion cDNA was introduced into murine pro-B cells with retrovirus and the cells were injected into immunodeficiency mice. As a result, the DUX4-IGH expression pro-B cells were proliferated in vivo, but maintained at an immature stage (CD19+CD43+c-kit+ CD25− IL7Ra+ IgM−) (FIG. 5a, FIG. 5c). These cells can be transplanted successively into secondary and tertiary recipients, which indicates that they have self-renewal activity. In contrast, when the wildtype DUX4 is introduced using the same retrovirus vector, the murine pro-B cells caused apoptosis. Therefore, the murine transplant assay was conducted again with sorted B cells that were infected with a modified recombinant retrovirus to express a small amount of DUX4 under control of an internal ribosome entry site (ires) fragment. As a result, the wild type DUX4 did not exhibit significant effect on proliferation, but suppressed differentiation (data not shown).

When MEF2D-BCL9-expressing B cells were grown in vivo using the same transplant assay, MEF2D-BCL9 does not provide the in vivo proliferation superiority to the pro-B cells, but both MEF2D-BCL9 and MEF2D-HNRNPUL1 prevented the differentiation of the B cell at the stage of the pro-B cell in 4 of 17 mice (FIG. 5a).

Figure 5B:
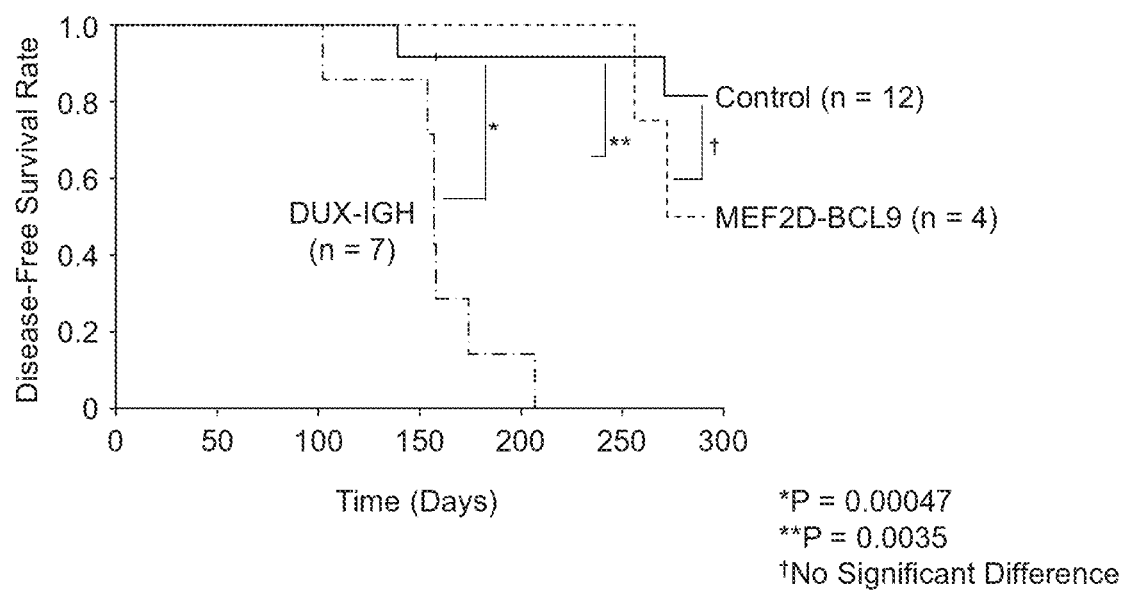
FIG. 5b shows Kaplan Mayer analysis of the primary transplant mice in Example 3. The disease-free intervals of each group were compared by Logrank with Bonferroni correction.
Figure 5C:
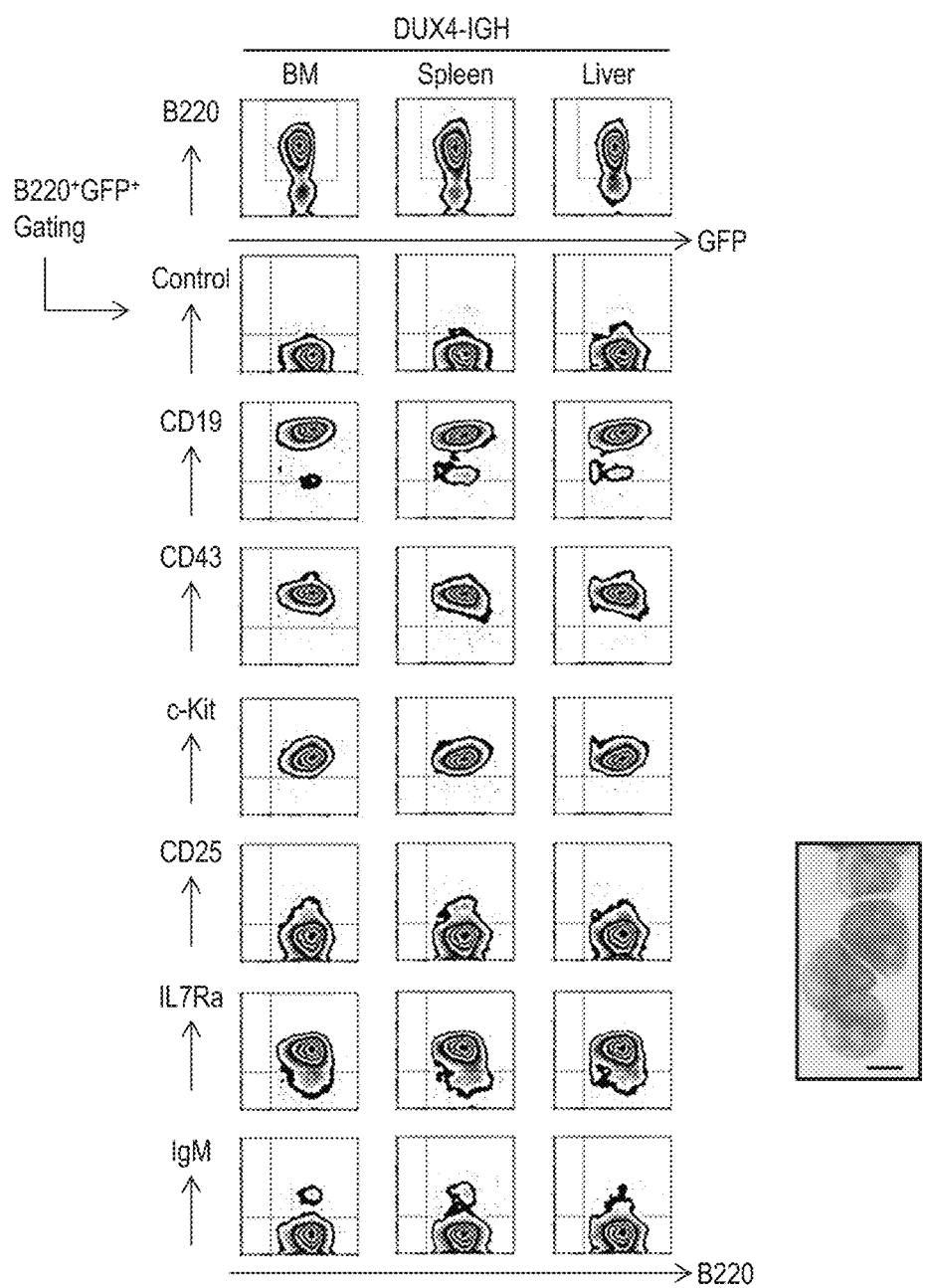
FIG. 5c shows that the mice in which the DUX4-IGH expressing pro-B cells were transplanted develop leukemia. Cells were obtained from the bone marrow (BM), the spleen, or the liver in the aforementioned mice and tested for the expression of the differentiation marker proteins. The B220$^+$ GFP$^+$ gating in the figure means that B220$^+$ GFP$^+$ cells were used for the analysis and the abscissa axis indicates the expression intensity of B220 and the ordinate axis indicates the expression intensity of each protein indicated on the left edge. The lower right photograph shows the bone marrow smear-stained with the Wright-Giemsa solution. The scale bar is 5 μm.

As a result of the DUX-IGH expression injection experiment, the mice finally developed leukemia with a median incubation period of 157 days (FIG. 5b). MEF2D-BCL9 has a lower penetrance, but also induces leukemia (up to 50% in an observation period of 290 days).

Example 4: Immunostaining Using Polyclonal Antibody

Anti-DUX antibodies were produced using 1 to 13 amino acid residues (MALPTPSDSTLPA: SEQ ID NO: 41) of the human DUX4 protein according to a conventional method in a rabbit and an anti-DUX4 polyclonal antibody was affinity purified with the aforementioned peptide. Subsequently, the obtained antibody (1.2 µg/ml) was contacted with bone marrow cells derived from leukemia patients for 32 minutes at room temperature and then detection was made by Bench-Mark XT system (Ventana Medical Systems Inc) according to instructions of the manufacturer.

Figure 8:
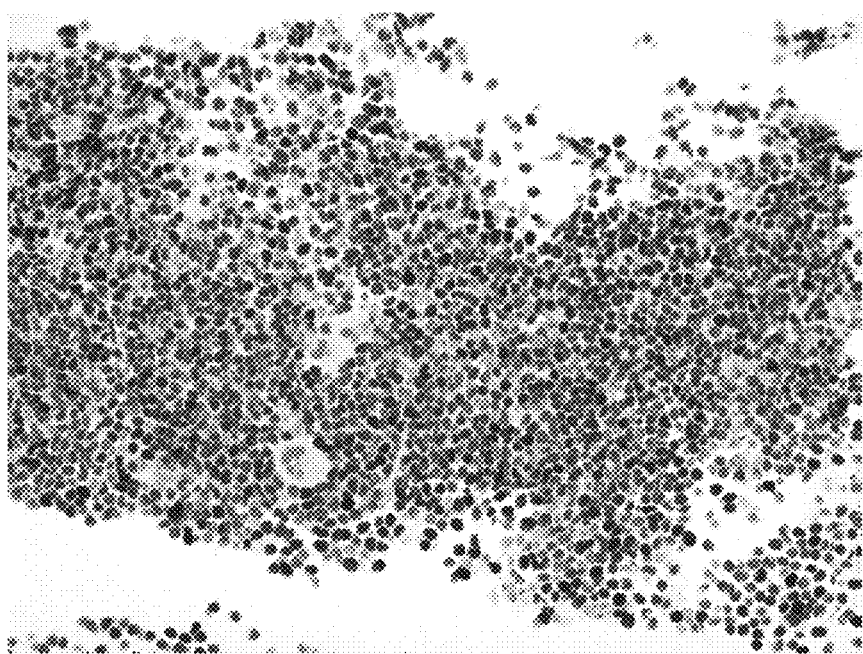
FIG. 8 shows the result of immunostaining of a bone marrow cell sample derived from a leukemia patient using an anti-DUX4 polyclonal antibody.

As a result, the bone marrow cell samples derived from leukemia patients were strongly stained with the anti-DUX4 polyclonal antibody (FIG. 8). This suggests that an anti-DUX4 polyclonal antibody can be used for the detection of leukemia.

All publications, patents and patent applications cited herein shall be entirely incorporated herein by reference.

The invention claimed is:

1. A method for determining whether a subject suffers from, or is likely to suffer from, malignant lymphoma or leukemia, the method comprising:
   detecting at least one of: a fusion mutation of a DUX4 gene and an immunoglobulin heavy chain or immunoglobulin light chain gene; and an overexpression of a DUX4 gene in a sample obtained from the subject;
   determining that the subject suffers from or is likely to suffer from malignant lymphoma or leukemia when at least one of the fusion mutations or the overexpression is detected; and
   performing a diagnostic procedure on the subject, wherein the diagnostic procedure comprises X-ray radiography or endoscopy, and
   wherein the DUX4 gene encodes a polypeptide consisting of the amino acid sequence set forth in SEQ ID NO: 2 and
   the fusion mutation of a DUX4 gene and an immunoglobulin heavy chain or immunoglobulin light chain gene is a mutation that forms a fusion gene comprising a part of the DUX4 gene on the 5' terminal side and a part of the immunoglobulin heavy chain or immunoglobulin light chain gene on the 3' terminal side.

2. The method according to claim 1, wherein the polypeptide encoded by the fusion gene of a DUX4 gene and an immunoglobulin heavy chain or immunoglobulin light chain gene comprises a member of the group consisting of:
   (i) an amino acid sequence comprising: an amino acid sequence comprising amino acids at positions 1 to 300 and lacking amino acids at positions 410 to 424 in the amino acid sequence set forth in SEQ ID NO: 2 on the N-terminal side; and 2 to 100 amino acids derived from an immunoglobulin heavy chain or immunoglobulin light chain gene on the C-terminal side;
   (ii) an amino acid sequence having an identity of 90% or more to the amino acid sequence of (i); and
   (iii) an amino acid sequence modified from the amino acid sequence of (i) by addition, deletion, and/or substitution of one or more amino acids.

3. The method according to claim 1, wherein the gene encoding the amino acid sequence set forth in SEQ ID NO: 2 comprises the nucleotide sequence set forth in SEQ ID NO: 1.

4. A method for determining whether a subject suffers from, or is likely to suffer from, malignant lymphoma or leukemia, the method comprising:
   detecting a fusion mutation of an MEF2D gene in a sample obtained from the subject;
   determining that the subject suffers from or is likely to suffer from malignant lymphoma or leukemia when the fusion mutation is detected; and
   performing a diagnostic procedure on the subject, wherein the diagnostic procedure comprises X-ray radiography or endoscopy, and
   wherein the fusion mutation of an MEF2D gene is a mutation that forms a fusion gene comprising a part of the MEF2D gene on the 5' terminal side and a part of a BCL9 gene on the 3' terminal side; and
   the polypeptide encoded by the fusion gene of an MEF2D gene and a BCL9 gene comprises a member of the group consisting of:
   (i) an amino acid sequence comprising amino acids at positions 1 to 200 in the amino acid sequence set forth in SEQ ID NO: 4 encoded by the MEF2D gene on the N-terminal side and amino acids at positions 1100 to 1426 in the amino acid sequence set forth in SEQ ID NO: 6 encoded by the BCL9 gene on the C-terminal side;
   (ii) an amino acid sequence having an identity of 90% or more to the amino acid sequence of (i); and
   (iii) an amino acid sequence modified from the amino acid sequence of (i) by addition, deletion, and/or substitution of one or more amino acids.

5. A method for determining whether a subject suffers from, or is likely to suffer from, malignant lymphoma or leukemia, the method comprising:
   detecting a fusion mutation of an MEF2D gene in a sample obtained from the subject;

determining that the subject suffers from or is likely to suffer from malignant lymphoma or leukemia when the fusion mutation is detected; and performing a diagnostic procedure on the subject, wherein the diagnostic procedure comprises X-ray radiography or endoscopy, and wherein the fusion mutation of an MEF2D gene is a mutation that forms a fusion gene comprising a part of the MEF2D gene on the 5' terminal side and a part of the HNRNPUL1 gene on the 3' terminal side; and a polypeptide encoded by the fusion gene of an MEF2D gene and an HNRNPUL1 gene comprises a member of the group consisting of:

(i) an amino acid sequence comprising amino acids at positions 1 to 335 in the amino acid sequence set forth in SEQ ID NO: 4 encoded by the MEF2D gene on the N-terminal side and amino acids at positions 563 to 856 in the amino acid sequence set forth in SEQ ID NO: 8 encoded by the HNRNPUL1 gene on the C-terminal side;

(ii) an amino acid sequence having an identity of 90% or more to the amino acid sequence of (i); and (iii) an amino acid sequence modified from the amino acid sequence of (i) by addition, deletion, and/or substitution of one or more amino acids.

6. The method according to claim 1, wherein the leukemia is acute lymphoblastic leukemia.

7. The method according to claim 6, wherein the acute lymphoblastic leukemia is adolescent and young adult acute lymphoblastic leukemia.

* * * * *